(12) United States Patent
Rosenbaum

(10) Patent No.: US 6,210,899 B1
(45) Date of Patent: Apr. 3, 2001

(54) USE OF A BMP PROTEIN RECEPTOR COMPLEX FOR SCREENING BONE METABOLISM ACTIVES AND CELLS CO-TRANSFECTED WITH A TYPE II BMP RECEPTOR AND TYPE I BMP RECEPTOR

(75) Inventor: Jan Susan Rosenbaum, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/462,467

(22) Filed: Jun. 5, 1995

Related U.S. Application Data

(63) Continuation-in-part of application No. 08/334,178, filed on Nov. 4, 1994, now abandoned.

(51) Int. Cl.$^7$ .................. G01N 33/53; G01N 33/566; A61K 38/00; C07K 1/00
(52) U.S. Cl. .................. 435/7.1; 435/7.2; 435/7.93; 436/501; 530/350
(58) Field of Search .................. 435/7.1, 7.8, 7.95, 435/967, 7.2, 7.93; 530/300, 840, 350; 436/501, 504

(56) References Cited

U.S. PATENT DOCUMENTS

| 5,141,905 | 8/1992 | Rosen et al. | 435/69.1 |
|---|---|---|---|
| 5,216,126 | 6/1993 | Cox et al. | 530/350 |

FOREIGN PATENT DOCUMENTS

| 0 369 861 | 5/1990 | (EP) | C07K/15/12 |
|---|---|---|---|
| 92/20793 | 11/1992 | (WO) | C12N/15/12 |
| 93/09228 | 5/1993 | (WO) | C12N/15/12 |
| 93/19177 | 9/1993 | (WO) | C12N/15/12 |
| 94/11502 | 5/1994 | (WO) | C12N/15/12 |
| 95/14778 | 1/1995 | (WO) | C12N/15/12 |
| 95/07982 | 3/1995 | (WO) | C12N/15/12 |

OTHER PUBLICATIONS

Hoodless, P. A., Haerry, T. Abdollah, S., Stapleton, M., O'Connor, M.B., Attisano, L., and Wrana, J.L. (May 17, 1996). "MADR1, a MAD–related protein that functions in BMP–2 signaling pathways", Cell 85: 489–500.

Liu, F., Hata A., Baker, J.C., Doody, J., Cárcamo, J., Harland, R.M., and Massagué, J. (Jun. 13, 1996). "A human Mad protein acting as a BMP–regulated transcriptional activator", Nature 381:620–623.

Bergonzoni, L., Caccia, P., Cletini, O., Sarmientos, P., & Isacchi, A. (Nov. 15, 1992) "Characterization of a Biologically Active Extracellular Domain of Fibroblast Growth Factor Receptor 1 Expressed in *Escherichia coli*", Eur. J. Biochem., 210, 823–829.

Fernandez–Botran, R. (Aug. 1991) "Soluble Cytokine Receptors: Their Role in Immunoregulation", FASEB J., 5, 2567–2574.

Kawabata, M., Chytil, A. & Moses, H. (Mar. 10, 1995) "Cloning of a Novel Type II Serine/Threonine Kinase Receptor through Interaction with the Type I Transforming Growth Factor–β Receptor", J. Biol. Chem., 270, 5625–5630.

Lev, S., Yarden, Y., & Givol, D. (May 25, 1992) "A Recombinant Ectodomain of the Receptor for the Stem Cell Factor (SCF) Retains Ligand–induced Receptor Dimerization and Antagonizes SCF–stimulated Cellular Responses", J. Biol. Chem. 267, 10866–10873.

Lin, H., Moustakas, A., Knaus, P., Wells, R., Henis, Y. & Lodish, H. (Feb. 10, 1995) "The Soluble Exoplasmic Domain of the Type II Transforming Growth Factor (TGF)–β Receptor", J. Biol. Chem. 270, 2747–2754.

Liu, F., Ventura, F., Doody, J., & Massagué, J. (Jul. 1995) "Human Type II Receptor for Bone Morphogenic Proteins (BMPs): Extension of the Two–Kinase Receptor Model to the BMPs", Mol. Cell. Biol. 15, 3479–3486.

Nohno, T., Ishikawa, T., Saito, T., Hosokawa, K., Noji, S., Wolsing, D., & Rosenbaum, J. (Sep. 22, 1995) "Identification of a Human Type II Receptor for Bone Morphogenetic Protein–4 That Forms Differential Heteromeric Complexes with Bone Morphogenetic Protein Type I Receptors", J. Biol. Chem. 270, 22522–22526.

Pennica, D., Kohr, W., Fendly, B., Shire,S., Raab, H., Borchardt, P., Lewis, M. & Goeddel, D. (Jan. 1992) "Characterization of a Recombinant Extracellular Domain of the Type 1 Tumor Necrosis Factor Receptor: Evidence for Tumor Necrosis Factor–α Induced Receptor Aggregation", Biochemistry 31, 1134–1141.

Rosenzweig B. L., Imamura, T., Okadome, T., Cox, G., Yamashita, H., Ten Dijke, P., Heldin, C. & Miyazono, K. (Aug. 1995) "Cloning and Characterization of a Human Type II Receptor for Bone Morphogenetic Proteins", Proc. Natl. Acad. Sci. 92, 7632–7636.

(List continued on next page.)

Primary Examiner—Jyothsna Venkat
Assistant Examiner—P. Ponnaluri
(74) Attorney, Agent, or Firm—Kelly McDow-Dunham; Brahn Corstanje; Carl Roof

(57) ABSTRACT

The present invention relates to a method for determining whether a compound is capable of binding to a BMP receptor kinase protein complex. The invention further relates to a method for determining the concentration of a BMP receptor ligand in a clinical sample. The invention also relates to a host cell co-transfected with an expression vector comprising a DNA sequence that codes for the BMP receptor kinase protein BRK-3 and an expression vector comprising a DNA sequence that codes for a BMP type I receptor kinase protein. The invention further relates to a host cell co-transfected with an expression vector comprising a DNA sequence that codes for a soluble or incomplete BMP type I receptor kinase protein and a soluble or incomplete BMP receptor kinase protein BRK-3. The invention further relates to a method for determining whether a test compound produces a signal upon binding to a BMP receptor protein complex.

7 Claims, 15 Drawing Sheets

OTHER PUBLICATIONS

Attisano, L., J. Cárcamo, F. Ventura, F. M. B. Weis, J. Massagué and J. L. Wrana, "Identification of Human Activin and TGFβ Type I Receptors That Form Heteromeric Kinase Complexes with Type II Receptors", Cell, Vol. 75, pp. 671–680 (Nov. 19, 1993).

Attisano, L., J. L. Wrana, S. Cheifetz and J. Massagué, "Novel Activin Receptors: Distinct Genes and Alternative mRNA Splicing Generate a Repertoire of Serine/Threonine Kinase Receptors", Cell, vol. 68, pp. 97–108 (Jan. 10, 1992).

Attisano, L., J. L. Wrana, F. López–Casillas and J. Massagué, "TGF–β Receptors and Actions", Biochimica et Biophysica Acta, vol. 1222, No. 1, pp. 71–80 (May 26, 1994).

Baarends, W. M., M. J. L. van Helmond, M. Post, P. J. C. M. van der Schoot, J. W. Hoogerbrugge, J. P. de Winter, J. T. J. Uilenbroek, B. Karels, L. G. Wilming, J. H. C. Meijers, A. P. N. Themmen and J. A. Grootegoed, "A Novel Member of the Transmembrane Serine/threonine Kinase Receptor Family Is Specifically Expressed in the Gonads and in Mesenchymal Cells Adjacent to the Müllerian Duct", Development, vol. 120, pp. 189–197 (no month identified 1994).

Basler, K., T. Edlund, T. M. Jessell and T. Yamada, "Control of Cell Pattern in the Neural Tube: Regulation of Cell Differentiation by dorsalin–1, a Novel TGFβ Family Member", Cell, vol. 73, pp. 687–702 (May 1993).

Bassing, C. H., J. M. Yingling, D. J. Howe, T. Wang, W. W. He, M. L. Gustafson, P. Shah, P. K. Donahoe and X. F. Wang, "A Transforming Growth Factor β Type I Receptor That Signals to Activate Gene Expression", Science, vol. 263, pp. 87–89 (Jan. 7, 1994).

Blessing, M., L. B. Nanney, L. E. King, C. M. Jones and B. L. Hogan, "Transgenic Mice as a Model to Study the Role of TGF–β–related molecules in Hair Follicles", Genes Dev., vol. 7, No. 2, pp. 204–215 (Feb. 1993).

Brummel, T.J., V. Twombly, G. Marqués, J.L. Wrana, S.J. Newfeld, L. Attisano, J. Massagué, M.B. O'Connor and W.M. Gelbart, "Characterization and Relationship of dpp Receptors Encoded by the Saxaphone and Thick Veins genes in Drosphilia", Cell, vol. 78, pp. 251–261 (Jul. 29, 1994).

Cárcamo, J., F. M. B. Weis, F. Ventura, R. Wieser, J. L. Wrana, L. Attisano and J. Massagué, "Type I Receptors Specify Growth–Inhibitory and Transcriptional Responses to Transforming Growth Factor β and Activin", Molecular and Cellular Biology, vol. 14, No. 6, pp. 3810–3821 (Jun. 1994).

Chen, R–H. and R. Derynck, "Homomeric Interactions Between Type II Transforming Growth Factor β Receptors", J. Biol. Chem., vol. 269, No. 36, pp. 22868–22874 (Sep. 9, 1994).

Cunningham, N. S., V. Paralkar and A. H. Reddi, "Osteogenin and Recombinant Bone Morphogenetic Protein 2B Are Chemotactic for Human Monocytes and Stimulate Transforming Growth Factor $β_1$ mRNA Expression", Proc. Natl. Acad. Sci. USA, vol. 89, pp. 11740–11744 (Dec. 1992).

Drozdoff, V., N. A. Wall and W. J. Pledger, "Expression and Growth Inhibitory Effect of Decapentaplegic Vg–related protein 6: Evidence for a Regulatory Role in Keratinocyte Differentiation", Proc. Natl. Acad. Sci. USA, vol. 91, pp. 5528–5532 (Jun. 1994).

Ebner, R., R.–H. Chen, S. Lawler, T. Zioncheck and R. Derynck, "Determination of Type I Receptor Specificity by the Type II Receptors for TGF–β or Activin", Science, vol. 262, pp. 900–902 (Nov. 5, 1993).

Estevez, M., L. Attisano, J. L. Wrana, P. S. Albert, J. Massagué and D. L. Riddle, "The daf–4 Gene Encodes A Bone Morphogenetic Protein Receptor Controlling C. elegans Dauer Larva Development", Nature, vol. 365, pp. 644–649 (Oct. 14, 1993).

Franzén, P., P. ten Dijke, H. Ichijo, H. Yamashita, P. Schulz, C. H. Heldin and K. Miyazono, Cloning of a TGFβ Type I Receptor That Forms a Heteromeric Complex with the TGFβ Type II Receptor, Cell, vol. 75, pp. 681–692 (Nov. 19, 1993).

Garrison, J.C., "Study of Protein Phosphorylation in Intact Cells", B:Protein Phosphorylation, A Practical Approach, Hardie, D.G. (ed), Chapter 1, pp. 1–29, (no month identified 1993).

Georgi, L. L., P. S. Albert and D. L. Riddle, "daf–1, a C. elegans Gene Controlling Dauer Larva Development, Encodes a Novel Receptor Protein Kinase", Cell, vol. 61, pp. 635–645 (May 18, 1990).

He, W. W., M. L. Gustafson, S. Hirobe and P. K. Donahoe, "Developmental Expression of Four Novel Serine Threonine Kinase Receptors Homologous to the Activin Transforming Growth Factor–β Type II Receptor Family", Developmental Dynamics, vol. 196, pp. 133–142 (no month identified 1993).

Inagaki, M., A. Moustakas, H.Y. Lin, H.F. Lodish and B.I. Carr, "Growth Inhibition By Transforming Growth Factor β (TGF–β) Type I is Restored in TGF–β Resistant Hepatoma Cells After Expression of TGF–β Receptor Type II cDNA", Proc. Nat'l. Acad. Sci. USA, vol. 90, pp. 5359–5363 (Jun. 1993).

Keonig, B.B., J. S. Cook, D. H. Wolsing, J. Ting, J. P. Tiesman, P. E. Correa, C. A. Olson, A. L. Pecquet, F. Ventura, R. A. Grant, G. X. Chen, J. L. Wrana, J. Massagué, and J. S. Rosenbaum, "Characterization and Cloning Of A Receptor For BMP–2 and BMP–4 From NIH3T3 Cells," Molecular and Cellular Biology, vol. 14, No. 9, pp. 5961–5974 (Sep. 1994).

Lin, H. Y., X. F. Wang, E. Ng–Eaton, R. A. Weinberg and H. F. Lodish, "Expression Cloning of the TGF–β Type II Receptor, a Functional Transmembrane Serine/Threonine Kinase", Cell, vol. 68, pp. 775–785 (Feb. 21, 1992).

Lin, H.Y. and A. Moustakas, "TGF–β Receptors: Structure and Function", Cellular and Molecular Biology, vol. 40, No. 3, pp. 337–349 (Mar. 1994).

Lyons, K. M., C. M. Jones and B. L. M. Hogan, "The DVR Gene Family in Embryonic Development", Trends in Genetics, vol. 7, No. 11–12, pp. 408–412 (Nov./Dec. 1991).

Luyten, F. P., P. Chen, V. Paralkar and A. H. Reddi, "Recombinant Bone Morphogenetic Protein–4, Transforming Growth Factor–$β_1$, and Activin A Enhance the Cartilage Phenotype of Articular Chondrocytes in Vitro," Experimental Cell Research, vol. 210, pp. 224–229 (no month identified 1994).

Mathews, L. S., "Activin Receptors and Cellular Signaling by the Receptor Serine Kinase Family", Endocrine Reviews, vol. 15, No. 3, pp. 310–325 (Jun. 1994).

Mathews, L. S. and W. W. Vale, "Expressing Cloning of an Activin Receptor, a Predicted Transmembrane Serine Kinase", Cell, vol. 65, pp. 973–982 (Jun. 14, 1991).

Mathews, L. S., W. W. Vale and C. R. Kintner, "Cloning of a Second Type of Activin Receptor and Functional Characterization in Xenopus Embyros", Science, vol. 255, pp. 1702–1705 (Mar. 27, 1992).

Nellen, D., M. Affolter and K. Basler, "Receptor Serine/threonine Kinases Implicated in the Control of Drosophila Body Pattern by Decapentaplegic", Cell, vol. 78, pp. 225–237 (Jul. 29, 1994).

Nohno, T., S. Sumitomo, T. Ishikawa, C. Ando, S. Nishida, S. Noji and T. Saito, "Nucleotide Sequence of a cDNA Encoding the Chicken Receptor Protein Kinase of the TGF–β Receptor Family", J. DNA Sequencing and Mapping, vol. 3, No. 6, pp. 393–396 (no month identified 1993).

Okano, H., S. Yoshikawa, A. Suzuki, N. Ueno, M. Kaizu, O. Masataka, T. Takahashi, M. Matsumoto, K. Sawamoto and K. Mikoshiba, "Cloning of a *Drosophila melanogaster* Homologue of the Mouse Type I Bone Morphogenetic Proteins–2/–4 Receptor: A Potential Decapentaplegic Receptor", Gene, vol. 148, pp. 203–209 (no month identified 1994).

Özjkaynak, E., P.N.H, Schnegelsberg, D.F. Jin, G.M, Clifford, F. D. Warren, E. A. Drier and H. Oppermann, "A New Member of the Transforming Growth Factor–β Superfamily Expressed Early in Embryogenesis", *J. Biol. Chem.*, vol. 267, No. 35, pp. 25220–25227 (Dec. 1992).

Paralkar, V. M., R. G. Hammonds and A. H. Reddi, "Identification and Characterization of Cellular Binding Proteins (Receptors) for Recombinant Human Bone Morphogenetic Protein 2B, and Initiator of Bone Differentiation Cascade", Proc. Natl. Acad. Sci. USA, vol. 88, pp. 3397–3401 (Apr. 1991).

Penton, A., Y. Chen, K. Staehling–Hampton, J. L. Wrana, L. Attisano, J. Szidonya, A. Cassill, J. Massagué and F. M. Hoffmann, "Identification of Two Bone Morphogenetic Protein Type I Receptors, BRK25D and BRK43E, in Drosophila and Evidence That BRK25D is a decapentaplegic Receptor," Cell, vol. 78, pp. 239–250 (Jul. 29, 199).

Sumitomo, S., T. Saito and T. Nohno, "A New Receptor Protein Kinase from Chick Embryo Related to Type II Receptor for TGF–β", J. DNA Sequence, vol. 3, pp. 297–302 (no month identified 1993).

Suzuki, A., N. Shioda, T. Maeda, M. Tada and N. Ueno, "A Mouse TGF–β Type I Receptor or Ligand Binding", Biochem. Biophys. Res. Commun., vol. 198, No. 3, pp. 1063–1069 (Feb. 15, 1994).

Takeda, K., S. Oida, H. Ichiho, T. Iimura, Y. Maruoka, T. Amagasa and S. Sasaki, "Molecular Cloning of Rat Bone Morphogenetic Protein (BMP) Type IA Receptor and Its Expression During Ectopic Bone Formation Induced by MBP", Biochem. Biophys. Res. Commun., vol. 204, No. 1, pp. 203–209 (Oct. 14, 1994).

ten Dijke, P., H. Ichijo, P. Franzén, P. Schulz, J. Saras, H. Toyoshima, C. H. Heldin and K. Miyazono, "Activin Receptor–like Kinases: A Novel Subclass of Cell–surface Receptors with Predicted Serine/Threonine Kinase Activity", Oncogene, vol. 8, pp. 2879–2887 (no month identified 1993).

ten Dijke, H. Yamashita, H. Ichijo, P. Franzén, M. Laiho, K. Miyazono, C. H. Heldin, "Characterization of Type I Receptors for Transforming Growth Factor–β and Activin", Science, vol. 264, pp. 101–104 (Apr. 1, 1994).

ten Dijke, P., H. Yamashita, T. K. Sampath, A. H. Reddi, M. Estevez, D. L. Riddle, H. Ichijo, C. H. Heldin and K. Miyazono, "Identification of Type I Receptors for Osteogenic Protein–1 and Bone Morphogenetic Protein–4", J. Biological Chemistry, vol. 269, No. 25, pp. 16985–16988 ( Jun. 1994).

Wall, N.A., M. Blessing, V.V.E. Wright and B.L.M. Hogan, "Biosynthesis and In Vivo Localization of the Decapentaplegic–Vg–related Protein, DVR–6 (Bone Morphogenetic Protein–6)", J. Cell Biol., vol. 120, No. 2, pp. 493–502 (Jan. 1993).

Wozney, J. M., "The Bone Morphogenetic Protein Family", Molec. Reproduct. and Develop., vol. 32, No. 2, pp. 160–167 (Jun. 1992).

Wrana, J.L., L. Attisano, J. Cárcamo, A. Zentella, J. Doody, M. Laiho, X–F. Wang and J. Massagué, "TGF–β Signals Through a Heteromeric Protein Kinase Receptor Complex", Cell, vol. 71, pp. 1003–1014 (Dec. 11, 1992).

Wrana, J.L., L. Attisano, R. Wieser, F. Ventura and J. Massagué, "Mechanism of Activation of the TGF–β Receptor", Nature, vol. 370, pp. 341–347 (Aug. 4, 1994).

Xie, T., A. L. Finelli and R. W. Padgett, "The *Drosophila saxophone* Gene: A Serine–Threonine Kinase Receptor of the TGF–β Superfamily", Science, vol. 263, pp. 1756–1759 (Mar. 25, 1994).

Yamashita, H., P. ten Dijke, P. Franzén, K. Miyazono and C–H. Heldin, "Formation of Hetero–oligomeric Complexes of Type I and Type II Receptors for Transforming Growth Factor–β", J. Biol. Chem., vol. 269, No. 31, pp. 20172–20178 (Aug. 5, 1994).

Yamaji, N., R. S. Thies, A. J. Celeste and J. M. Wozney, "The Molecular Cloning of Bone Morphogenetic Protein Receptors", Abstract from Meeting of American Society for Bone and Mineral Research, (Sep. 22, 1993).

PCR PRIMERS USED IN ISOLATION OF HUMAN BRK-3

TSK-1: Sense derived form kinase domain II

```
                        A A
5' G A C G T N G C N G T N A A   T N T T 3'
                        G G
```

TSK-2: Antisense derived from kinase domain VIII

```
        T                 T A
5' G A C   T C N G G N G C N A A   T A 3'
        C                 G G
```

AVR-5: Sense derived form kinase domain IV

```
         A    T    A    T
5' A T G A A   C A   G A   A A   A T 3'
         G    C    G    C
```

TSK-4: Antisense derived form kinase domain VIB

USE OF A BMP PROTEIN RECEPTOR COMPLEX FOR SCREENING BONE METABOLISM ACTIVES AND CELLS CO-TRANSFECTED WITH A TYPE II BMP RECEPTOR AND TYPE I BMP RECEPTOR

This is a continuation-in-part of application Ser. No. 08/334,178, filed on Nov. 4, 1994, now abandoned.

TECHNICAL FIELD

The present invention relates to the field of bone formation and development. Specifically, the present invention relates to the use of a new bone morphogenetic protein type II receptor, together with a bone morphogenetic type I receptor, for screening bone metabolism actives. The invention further relates to cells co-transfected with DNA coding for this receptor and DNA coding for a type I bone morphogenetic protein receptor.

BACKGROUND

Humans and other warm-blooded animals can be afflicted by a number of bone-related disorders. Such disorders range from bone fractures, to debilitating diseases such as osteoporosis. While in healthy individuals bone growth generally proceeds normally and fractures heal without the need for pharmacological intervention, in certain instances bones may become weakened or may fail to heal properly. For example, healing may proceed slowly in the elderly and in patients undergoing treatment with corticosteroids (e.g., transplant patients). Osteoporosis is a condition in which bone hard tissue is lost disproportionately to the development of new hard tissue. Osteoporosis can generally be defined as the reduction in the quantity of bone, or the atrophy of skeletal tissue; marrow and bone spaces become larger, fibrous binding decreases, and compact bone becomes fragile. Another bone related disorder is osteoarthritis, which is a disorder of the movable joints characterized by deterioration and abrasion of articular cartilage, as well as by formation of new bone at the joint surface.

While a variety of treatments are available for such bone-related disorders, none of the treatments provide optimum results. One of the difficulties facing individuals who treat bone-related disorders is a lack of complete understanding of bone metabolism and of the bone-related disorders. A key to such understanding is identifying and characterizing each of the components involved in bone growth. Bone morphogenetic proteins (BMPs) have been demonstrated to play a role in bone formation and development (J. M. Wozney, *Molec. Reproduct. and Develop.*, 32: 160–167 (1992)).

Furthermore, the role of BMPs may not be limited to their role in bone. The finding that the BMPs are found at significant concentrations in other tissues such as brain, kidney, stratified squamous epithelia, and hair follicle (N. A. Wall, M. Blessing, C. V. E. Wright, and B. L. M. Hogan, *J. Cell Biol.*, 120: 493–502 (1993); E. Özkaynak, P. N. J. Schnegelsberg, D. F. Jin, G. M. Clifford, F. D. Warren, E. A. Drier, and H. Oppermann, *J. Biol. Chem.*, 267: 25220–25227 (1992); K. M. Lyons, C. M. Jones, and B. L. M. Hogan, *Trends in Genetics*, 7: 408–412 (1991); V. Drozdoff, N. A. Wall, and W. J. Pledger, *Proceedings of the National Academy of Sciences, U.S.A.*, 91: 5528–5532 (1994)) suggests that they may play additional roles in development and differentiation. In support of this, BMPs have recently been found to promote nerve cell differentiation and to affect hair follicle formation (K. Basler, T. Edlund, T. M. Jessell, and T. Yamada, *Cell*, 73: 687–702 (1993); V. M. Paralkar, B. S. Weeks, Y. M. Yu, H. K. Kleinman, and A. H. Reddi, *J. Cell Biol.*, 119: 1721–1728 (1992); M. Blessing, L. B. Nanney, L. E. King, C. M. Jones, and B. L. Hogan, *Genes Dev.*, 7: 204–215 (1993)).

A BMP initiates its biological effect on cells by binding to a specific BMP receptor expressed on the plasma membrane of a BMP-responsive cell. A receptor is a protein, usually spanning the cell membrane, which binds to a ligand from outside the cell, and as a result of that binding sends a signal to the inside of the cell which alters cellular function. In this case, the ligand is the protein BMP, and the signal induces the cellular differentiation.

Because of the ability of a BMP receptor to specifically bind BMPs, purified BMP receptor compositions are useful in diagnostic assays for BMPs, as well as in raising antibodies to the BMP receptor for use in diagnosis and therapy. In addition, purified BMP receptor compositions may be used directly in therapy to bind or scavenge BMPs, thereby providing a means for regulating the activities of BMPs in bone and other tissues. In order to study the structural and biological characteristics of BMP receptors and the role played by BMPs in the responses of various cell populations to BMPs during tissue growth/formation stimulation, or to use a BMP receptor effectively in therapy, diagnosis, or assay, purified compositions of BMP receptor are needed. Such compositions, however, are obtainable in practical yields only by cloning and expressing genes encoding the receptors using recombinant DNA technology. Efforts to purify BMP receptors for use in biochemical analysis or to clone and express mammalian genes encoding BMP receptors have been impeded by lack of a suitable source of receptor protein or mRNA. Prior to the present invention, few cell lines were known to express high levels of high affinity BMP receptors which precluded purification of the receptor for protein sequencing or construction of genetic libraries for direct expression cloning. Availability of the BMP receptor sequence will make it possible to generate cell lines with high levels of recombinant BMP receptor for biochemical analysis and use in screening experiments.

The BMPs are members of the TGF-β superfamily. Other members of the TGF-β superfamily include TGF-β, activins, inhibins, Müllerian Inhibiting Substance, and the Growth and Differentiation Factors (GDFs). As expected, the receptors for various members of the TGF-β superfamily share similar structural features. Receptors of the TGF-β ligand superfamily are typically classified into one of two subgroups, designated as type I and type II. The type I and type II receptors are classified as such based on amino acid sequence characteristics. Both the type I and type II receptors possess a relatively small extracellular ligand binding domain, a transmembrane region, and an intracellular protein kinase domain that is predicted to have serine/threonine kinase activity (Lin and Moustakas, *Cellular and Molecular Biology*, 40: 337–349 (1994); L. S. Mathews, *Endocrine Reviews*, 15: 310–325 (1994); L. Attisano, J. L. Wrana, F. L ópez-Casillas, , and J. Massagué, *Biochimica et Biophysica Acta*, 1222: 71–80 (1994)).

The type I receptors cloned to date belong to a distinct family whose kinase domains are highly related and share >85% sequence similarity (B. B. Koenig et al., *Molecular and Cellular Biology*, 14: 5961–5974 (1994)). The intracellular juxtamembrane region of the type I receptors is characterized by an SGSGSG motif 35–40 amino acids from the transmembrane region, and the carboxy terminus of these receptors is extremely short (B. B. Koenig et al.,

*Molecular and Cellular Biology*, 14: 5961–5974 (1994); L. Attisano, J. L. Wrana, F. López-Casillas, and J. Massagué, *Biochimica et Biophysica Acta*, 1222: 71–80 (1994)). The extracellular domain of the type I receptors contains a characteristic cluster of cysteine residues, termed the "cysteine box", located within 25–30 amino acids of the transmembrane region, and another cluster of cysteine residues, termed the "upstream cysteine box", located after the putative signal sequence (B. B. Koenig, et al., *Molecular and Cellular Biology*, 14: 5961–5974 (1994); L. Attisano, et al., *Biochimica et Biophysica Acta*, 1222: 71–80 (1994)).

In contrast to the type I receptors, the kinase domains of the type II receptors are only distantly related to one another. The SGSGSG motif found in type I receptors is not found in type II receptors. Also, the "upstream cysteine box" of type I receptors is not present in type II receptors. Furthermore, while all of the activin type II receptors contain a proline-rich sequence motif in the intracellular juxtamembrane region, there is no characteristic sequence motif that is common to all type II receptors (L. S. Mathews, *Endocrine Reviews*, 15: 310–325 (1994)). The length of the carboxy terminus of the type II receptors is considerably variable, with the longest known carboxy terminus being found in the BMP type II receptor, DAF-4 (M. Estevez, L. Attisano, J. L. Wrana, P. S. Albert, J. Massagué, and D. L. Riddle, *Nature*, 365: 644–49 (1993)), that was cloned from the nematode *C. elegans*. The extracellular domain of the type II receptors contains a single cysteine box located near the transmembrane region. Aside from the presence of the cysteine box, there is little sequence similarity amongst the extracellular domains of the type II receptors for TGF-β, activin, and BMPs.

Signaling by members of the TGF-β ligand superfamily requires the presence of both type I and type II receptors on the surface of the same cell (L. S. Mathews, *Endocrine Reviews*, 15: 310–325 (1994); L. Attisano, J. L. Wrana, F. López-Casillas, and J. Massagué, *Biochimica et Biophysica Acta*, 1222: 71–80 (1994)). The BMPs are members of the TGF-β ligand superfamily; given the high degree of structural similarity among these family members, it is expected that their receptors will be structurally and functionally related to the TGF-β and activin receptors. It is anticipated that, like the TGF-β and activin receptor systems (J. Massagué, L. Attisano, and J. L. Wrana, *Trends in Cell Biology*, 4: 172–178 (1994)), both a BMP type I receptor and a BMP type II receptor will be needed in order to transduce a BMP signal within a cell or tissue. Hence, there is a need for a mammalian type II BMP receptor kinase protein in addition to the type I receptors that have already been cloned.

Three distinct mammalian type I receptors have been reported for the BMPs: Bone Morphogenetic Protein Receptor Kinase-1 (herein referred to as "BRK-1") (see U.S. Ser. No. 08/158,735, filed Nov. 24, 1993 by J. S. Cook, et al.; and B. B. Koenig et al., *Molecular and Cellular Biology*, 14: 5961–5974 (1994)), ALK-2, and ALK-6. BRK-1 is the mouse homologue of ALK-3, which has also been demonstrated to bind BMP-4, as does ALK-6; ALK-2 binds BMP-7 (see P. ten Dijke, H. Yamashita, T. K. Sampath, A. H. Reddi, M. Estevez, D. L. Riddle, H. Ichijo, C.-H. Heldin, and K. Miyazono, *J. Biological Chemistry*, 269: 16985–16988 (1994)). It is also postulated that ALK-6 is the mouse homologue of the chicken receptor Bone Morphogenetic Protein Receptor Kinase-2 (herein referred to as "BRK-2") (also referred to as RPK-1) (S. Sumitomo, T. Saito, and T. Nohno, *DNA Sequence*, 3: 297–302 (1993)). The rat homologue of BRK-1 has also been cloned, as BMPR-Ia (K. Takeda, S. Oida, H. Ichijo, T. Iimura, Y. Marnoka, T. Amagasa and S. Sasaki, *Biochemical and Biophysical Research Communications*, 204: 203–209 (1994)).

In co-pending application U.S. Ser. No. 08/334,179, filed Nov. 4, 1994 by Rosenbaum and Nohno, a novel mammalian BMP type II receptor (referred to as "BRK-3") is described and claimed. Prior to the cloning of the BRK-3 receptor, the only type II receptor for BMP-2 and BMP-4, named DAF-4, was cloned from the nematode *C. elegans* (M. Estevez, L. Attisano, J. L. Wrana, P. S. Albert, J. Massagué, and D. L. Riddle, *Nature*, 365: 644–9 (1993)). Because of the large evolutionary distance between the nematode and mammals, it has not been possible to use the DAF-4 cDNA as a probe with which to clone the mammalian DAF-4 homologue. This implies that the DNA sequence of the mammalian type II receptor for BMPs is substantially divergent from that of DAF-4, and it was therefore necessary to clone a mammalian type II receptor for the BMPs.

The BMP receptor kinase protein BRK-3 of the co-pending application provides a mammalian type II receptor which enables the formation of a complex with a BMP type I receptor. This complex, which is described in detail below, is capable of binding BMPs with high affinity, and is therefore useful for identifying compounds having BMP receptor affinity. The complex of the present invention will also enable the formation of a high affinity complex that is competent for signaling a response to BMPs in concert with the mammalian type I receptor(s) for BMPs. The mammalian BMP receptor complex is therefore more relevant for the identification of novel compounds which interact with the BMP receptor, and which will be useful as therapeutic agents in humans and other mammals, than is a receptor complex that is composed of the nematode type II receptor and the mammalian type I receptor.

OBJECTS OF THE PRESENT INVENTION

It is an object of the present invention to provide a method for identifying compounds capable of binding to a BMP receptor kinase protein complex.

It is also an object of the present invention to provide a method for determining the amount of a compound capable of binding a BMP receptor kinase protein complex in a sample.

It is also an object of the present invention to provide a host cell comprising a recombinant expression vector encoding a BMP type II receptor kinase protein and a recombinant expression vector encoding a BMP type I receptor kinase protein comprising said BMP receptor kinase protein complex.

It is also an object of the present invention to provide a method for determining whether a test compound produces a signal upon binding to a BMP receptor protein complex.

SUMMARY

The present invention relates to a method for determining whether a compound is capable of binding to a BMP receptor kinase protein complex, the method comprising introducing a sample comprising the compound to the BMP receptor kinase protein complex and allowing the compound to bind to the BMP receptor kinase protein complex, wherein the BMP receptor kinase protein complex is comprised of a BMP type I receptor kinase protein and the BMP receptor kinase protein BRK-3.

The invention further relates to a method for determining the concentration of a BMP receptor ligand in a clinical sample, the method comprising introducing the sample comprising the ligand to a BMP receptor kinase protein complex and allowing the ligand to bind to the BMP receptor kinase protein complex, wherein the BMP receptor kinase protein complex is comprised of a BMP type I receptor kinase protein and BMP receptor kinase protein BRK-3.

The invention further relates to a host cell co-transfected with an expression vector comprising a DNA sequence that codes for the BMP receptor kinase protein BRK-3 and an expression vector comprising a DNA sequence that codes for a BMP type I receptor kinase protein.

The invention further relates to a host cell co-transfected with an expression vector comprising a DNA sequence that codes for a soluble BMP type I receptor kinase protein and a soluble BMP receptor kinase protein BRK-3.

The invention further relates to a host cell co-transfected with an expression vector comprising a DNA sequence that codes for an incomplete BMP type I receptor kinase protein and an incomplete BMP receptor kinase protein BRK-3.

The invention further relates to a method for determining a test compound produces a signal upon binding to a BMP receptor protein complex, the method comprising: (a) labeling BMP receptor protein complex expressing cells with $^{32}P$, wherein the cells have been transfected with a DNA sequence coding for BMP receptor kinase protein BRK-3 and a DNA sequence coding for a BMP type I receptor kinase protein; (b) culturing (i) a first set of the cells in the presence of the test compound, and (ii) a second set of the cells in the absence of the test compound; (c) quantitating via autoradiography any phosphorylated proteins produced from step (b); and (d) comparing the amount of phosphorylated proteins quantitated in step (c) from the first set of cells to the amount of phosphorylated proteins quantitated in step (c) for the second set of cells.

BRIEF DESCRIPTION OF THE DRAWINGS

FIG. 1 shows the DNA sequence of the degenerate oligonucleotide primers used in the PCR amplification of t-BRK-3. The nucleotide bases adenine, thymine, cytosine, and guanine are represented by A, T, C and G respectively. The letter N represents the presence of an equal mixture of A, T, C, and G at that site. The primers are derived from the sequence of the TGF-β type II receptor (H. Y. Lin, X. F. Wang, E. Ng-Eaton, R. A. Weinberg, and H. F. Lodish, *Cell*, 68: 775–785 (1992)).

Figure 13:
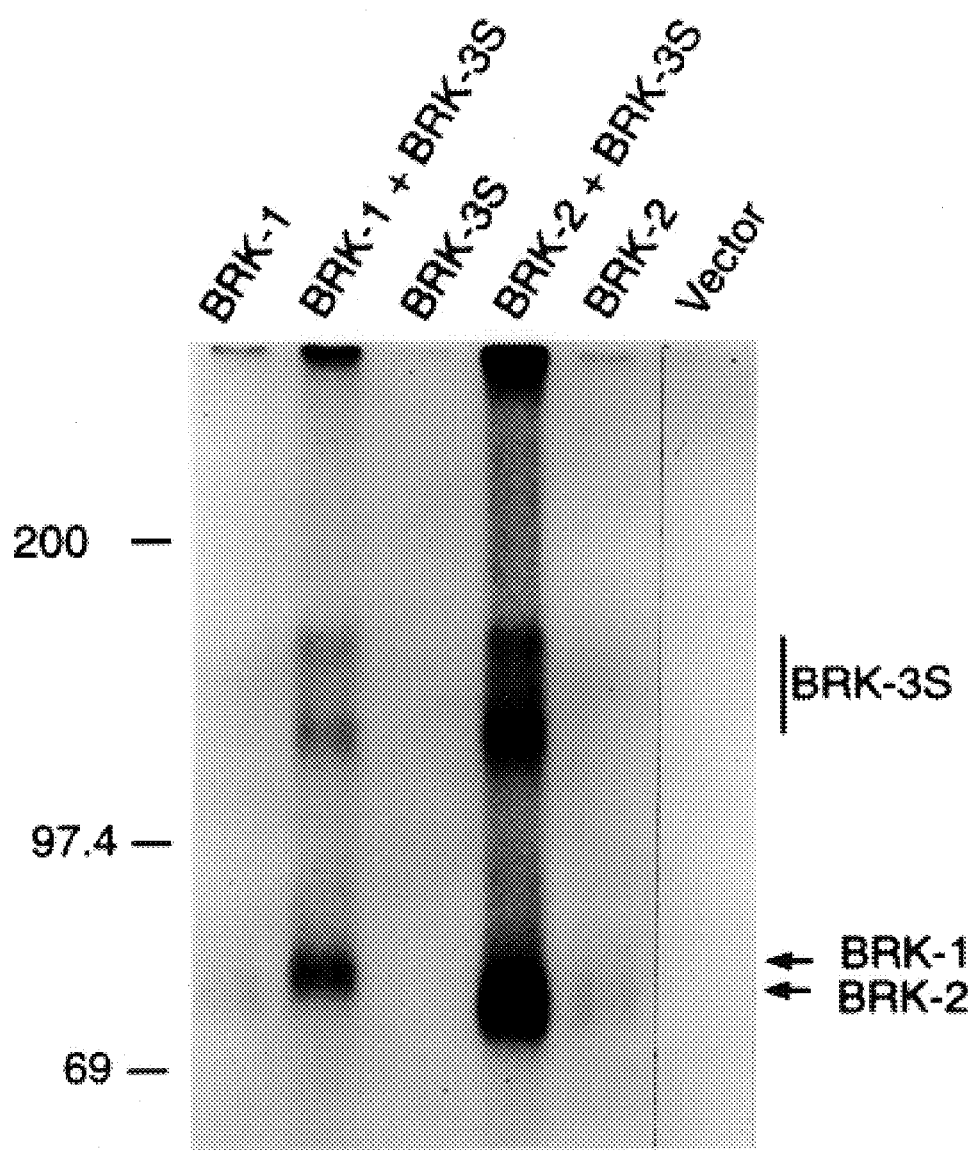

FIG. 13 shows crosslinking of [$^{125}$I]-BMP-4 to m-BRK-3 in the presence and absence of type I BMP receptors. COS-1 cells are transfected with the cDNA for BRK-3 using the construct pJT6-mBRK-3S, and/or with cDNAs for BRK-1 (using pJT4-J159F) or BRK-2 (using pJT3-BRK-2). The cells are then allowed to bind [$^{125}$I]-BMP-4, crosslinked with disuccinimidyl suberate, and subjected to SDS gel electrophoresis. Position of molecular weight standards is indicated on the left. Left to right: COS-1 cells transfected with BRK-1 alone; BRK-1 plus m-BRK-3; m-BRK-3 alone; BRK-2 plus m-BRK-3; BRK-2 alone; and vector alone. Bands identified with BRK-1, BRK-2, and BRK-3 are indicated on the right.

Figure 14:
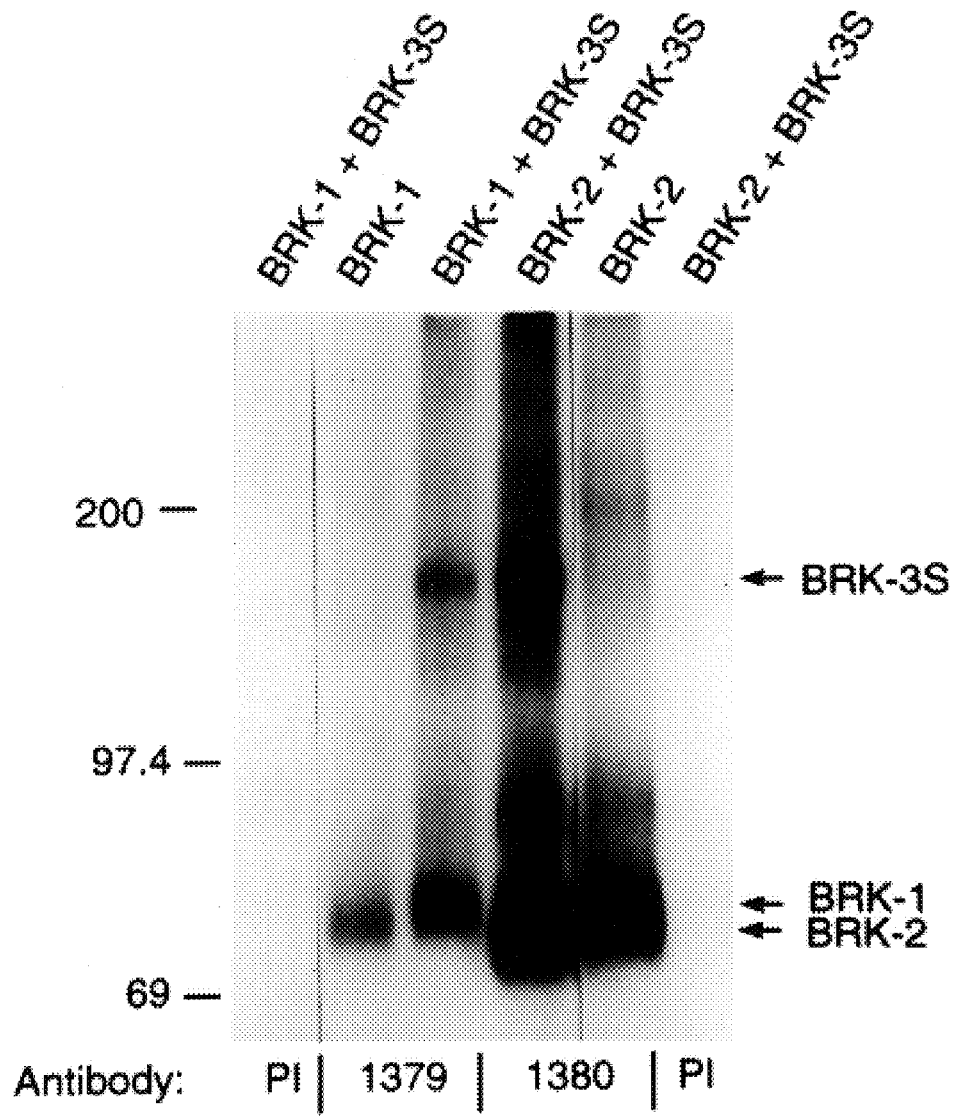

FIG. 14 shows immunoprecipitation of m-BRK-3 in the presence and absence of type I BMP receptors. COS-1 cells are transfected with the cDNA for m-BRK-3 using the construct pJT6-mBRK-3S, and/or with cDNAs for BRK-1 (using pJT4-J159F) or BRK-2 (using pJT3-BRK-2). The cells are then allowed to bind [$^{125}$I]-BMP-4, crosslinked with disuccinimidyl suberate, immunoprecipitated with antibodies to BRK-1 or BRK-2, and subjected to SDS gel electrophoresis. Antisera used are indicated below the lanes: PI, preimmune; 1379, for cells transfected with cDNA for BRK-1; 1380, for cells transfected with cDNA for BRK-2. Position of molecular weight standards is indicated on the left. Left to right, COS-1 cells transfected with BRK-1 plus m-BRK-3 (preimmune serum); BRK-1 alone; BRK-1 plus m-BRK-3; BRK-2 plus m-BRK-3; BRK-2 alone; and BRK-2 plus m-BRK-3 (preimmune serum).

Figure 15:
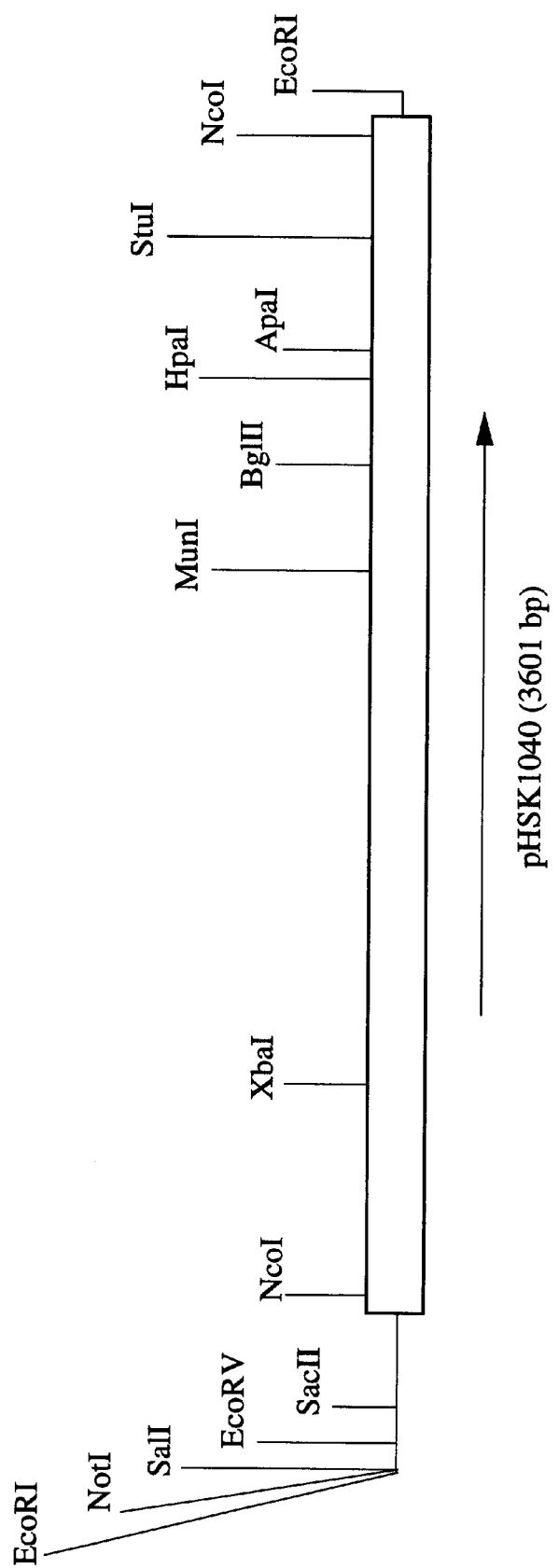

FIG. 15 shows a map of the insert of pHSK1040. This construct contains the complete coding region of human BRK-3 in BLUESCRIPT II SK (−).

DESCRIPTION

The present invention answers the need for a method for determining whether a compound has BMP receptor affinity. The method comprises introducing a sample comprising a test compound to a BMP receptor kinase protein complex and allowing the compound to bind to the BMP receptor kinase protein complex, wherein the receptor complex comprises a BMP type I receptor kinase protein and the BMP type II receptor kinase protein designated herein as "BRK-3". The invention also answers the need for a host cell that is co-transfected with an expression vector comprising a DNA sequence that codes for BMP receptor kinase protein BRK-3 and an expression vector comprising a DNA sequence that codes for a BMP type I receptor kinase protein. Also provided is a method for determining the concentration of a BMP receptor ligand in a clinical sample, the method comprising introducing the sample comprising the ligand to a BMP receptor kinase protein complex and allowing the ligand to bind to the receptor complex, wherein the receptor complex is comprised of a BMP type I receptor kinase protein and BMP receptor kinase protein BRK-3. The invention also answers the need for a host cell that is co-transfected with an expression vector comprising a DNA sequence that codes for a soluble BMP receptor kinase proten BRK-3 and an expression vector comprising a DNA sequence that codes for a soluble BMP type I receptor kinase protein. The invention also answers the need for a host cell that is co-transfected with an expression vector comprising a DNA sequence that codes for an incomplete BMP receptor kinase proten BRK-3 and an expression vector comprising a DNA sequence that codes for an incomplete BMP type I receptor kinase protein.

As used herein, "human BMP receptor kinase protein-3" or "h-BRK-3" means a protein having the amino acid sequence SEQ ID NO:2, as well as proteins having amino acid sequences substantially similar to SEQ ID NO:2, and which are biologically active in that they are capable of binding a BMP molecule (including, but not limited to BMP-2, DR-BMP-2, BMP-4, and/or BMP-7), or transducing a biological signal initiated by a BMP molecule binding to a cell, or crossreacting with antibodies raised against h-BRK-3 protein, or peptides derived from the protein sequence of h-BRK-3 or m-BRK-3 (see below), or forming a complex with a BMP type I receptor, or co-immunoprecipitating with a BMP type I receptor when antibodies specific for either h-BRK-3 or a BMP type I receptor are used.

As used herein, "truncated human BMP receptor kinase protein" or "t-BRK-3" means a protein having amino acid sequence SEQ ID NO:4, or a sequence having the properties described above for BRK-3.

As used herein, "mouse BMP receptor kinase protein" or "m-BRK-3" means a protein having amino acid sequence SEQ ID NO:8, or a sequence having the properties described above for BRK-3.

As used herein, "BMP receptor kinase protein BRK-3" or "BRK-3" refers individually and collectively to the receptor proteins h-BRK-3, t-BRK-3, and m-BRK-3 (and soluble and incomplete fragments thereof), described above, as well as BMP receptor kinase proteins substantially similar to h-BRK-3, t-BRK-3, and m-BRK-3 (and soluble and incomplete fragments thereof). Such receptor proteins, DNA sequences coding for the proteins, and recombinant expression vectors comprising said DNA are described and claimed in U.S. Ser. No. 08/334,179, filed on Nov. 4, 1994, by Rosenbaum and Nohno.

As used herein, a "BMP Type I Receptor Kinase" is a protein capable of binding BMP-2, BMP-4 and/or other known BMPs, and bears sequence characteristics of a type I receptor including, but not limited to, an extracellular ligand binding domain containing a cysteine box and an upstream cysteine box, an SGSGSG motif, designated the GS domain, in the intracellular juxtamembrane region, an intracellular kinase domain that is greater than about 85% similar to other type I receptors for other ligands in the TGF-β superfamily, and/or a relatively short carboxy terminus. As used herein, "BMP Type I Receptor Kinase" also includes receptor proteins having the characteristics of a BMP type I receptor as described in the literature, such as in: B. B. Koenig et al., *Molecular and Cellular Biology*, 14: 5961–5974 (1994); L. Attisano, et al., *Biochimica et Biophysica Acta*, 1222: 71–80 (1994); J. Massagué, L. Attisano, and J. L. Wrana, *Trends in Cell Biology*, 4: 172–178 (1994); and ten Dijke, et al., *J. Biological Chemistry*, 269: 16985–16988 (1994).

Examples of BMP type I receptors include, but are not limited to: BRK-1 (B. B. Koenig et al., *Molecular and Cellular Biology*, 14: 5961–5974 (1994), the rat homologue of which is BMPR-Ia (K. Takeda, S. Oida, H. Ichijo, T. Iimura, Y. Maruoka, T. Amagasa, and S. Sasaki, *Biochem. Biophys. Res. Communica.*, 204: 203–209 (1994)); BRK-2, also referred to as RPK-1 (S. Sumitomo, T. Saito, and T. Nohno, *DNA Sequence*, 3: 297–302 (1993), and postulated to be the chicken homologue of ALK-6 (P. ten Dijke, H. Yamashita, H. Ichijo, P. Franzén, M. Laiho, K. Miyazono, and C.-H. Heldin, *Science,* 264: 101–104 (1994)); ALK-2, which has been shown to be a receptor for BMP-7 (ten Dijke et al., *J. Biological Chemistry,* 269: 16985–16988 (1994)); the Xenopus BMP type I receptor that binds BMP-2 and BMP-4 and which is involved in mesoderm induction (J. M. Graff, R. S. Thies, J. J. Song, A. J. Celeste, and D. A. Melton, *Cell,* 79: 169–179 (1994)); and type I receptors from Drosophila that bind the decapentaplegic peptide, which is the Drosophila homologue of BMP-2 and BMP-4. These Drosophila receptors are designated 25D1, 25D2, and 43E (T. Xie, A. L. Finelli, and R. W. Padgett, *Science,* 263: 1756–1759 (1994); A. Penton, Y. Chen, K. Staehling-Hampton, J. L. Wrana, L. Attisano, J. Szidonya, J. A. Cassill, J. Massagué, and F. M. Hoffmann, *Cell,* 78: 239–250 (1994); and T. J. Brummel, V. Twombly, G. Marqués, J. L. Wrana, S. J. Newfeld, L. Attisano, J. Massagué, M. B. O'Connor, and W. M. Gelbart, *Cell,* 78: 251–261 (1994)). Preferred BMP type I receptors useful in the present invention include, but are not limited to, polypeptides having the amino acid sequences substantially similar to SEQ ID NO:12 (BRK-1), SEQ ID NO: 16 (soluble BRK-1); SEQ ID NO:20 (incomplete BRK-1); SEQ ID NO:14 (BRK-2); SEQ ID NO:18 (soluble BRK-2); and SEQ ID NO:22 (incomplete BRK-2).

As used herein, "soluble fragment" refers to an amino acid sequence corresponding to the extracellular region of BRK-1, BRK-2, or BRK-3 which is capable of binding BMPs. Soluble fragments include truncated proteins wherein regions of the receptor molecule not required for BMP binding have been deleted. Examples of such soluble fragments for BRK-3 include, but are not limited to, polypeptides having the amino acid sequences substantially similar to SEQ ID NO:6; SEQ ID NO:10; amino acid residues 1-150 depicted in SEQ ID NO:2; amino acid residues 1–150 depicted in SEQ ID NO:8; or polypeptides encoded by nucleic acid residues substantially similar to SEQ ID NO:5; SEQ ID NO:9; nucleic acid residues 409–858 depicted in SEQ ID NO:1, or nucleic acid residues 17–466 depicted in SEQ ID NO:7.

Examples of soluble fragments for BRK-1 include, but are not limited to, polypeptides having the amino acid sequences substantially similar to SEQ ID NO:16; amino acid residues 1–152 in SEQ ID NO:12; polypeptides encoded by nucleic acid residues substantially similar to SEQ ID NO:15; or polypeptides encoded by nucleic acid residues substantially similar to 11–466 in SEQ ID NO:11.

Examples of soluble fragments for BRK-2 include, but are not limited to, polypeptides having the amino acid sequences substantially similar to SEQ ID NO:18; amino acid residues 1–126 in SEQ ID NO:14; polypeptides encoded by nucleic acid residues substantially similar to SEQ ID NO: 17; or polypeptides encoded by nucleic acid residues substantially similar to 355–732 in SEQ ID NO:13.

As used herein, "incomplete receptor kinase fragment" refers to an amino acid sequence corresponding to the extracellular, transmembrane, and intracellular juxtamembrane region of BRK-1, BRK-2, or BRK-3 which is capable of binding BMPs in a manner similar to the full-length receptor, but which is incapable of signalling due to deletion of the intracelllular kinase domain. Examples of such incomplete receptor fragments for BRK-3 include, but are not limited to, polypeptides having the amino acid sequences substantially similar to SEQ ID NO: 24; SEQ ID NO:26; amino acids 1–200 in SEQ ID NO:2; amino acids 1–200 in SEQ ID NO:8; polypeptides encoded by nucleic acid residues substantially similar to SEQ ID NO: 23; polypeptides encoded by nucleic acid residues substantially similar to SEQ ID NO: 25; polypeptides encoded by nucleic acid residues substantially similar to 409–1008 in SEQ ID NO:1; or polypeptides encoded by nucleic acid residues substantially similar to 17–616 in SEQ ID NO:7.

Examples of incomplete receptor fragments for BRK-1 include, but are not limited to, polypeptides having the amino acid sequences substantially similar to SEQ ID NO:20; amino acid residues 1–231 in SEQ ID NO:12; polypeptides encoded by nucleic acid residues substantially similar to SEQ ID NO:19; or polypeptides encoded by nucleic acid residues substantially similar to 11–703 in SEQ ID NO:11.

Examples of incomplete receptor fragments for BRK-2 include, but are not limited to, polypeptides having the amino acid sequences substantially similar to SEQ ID NO:22; amino acid residues 1–201 in SEQ ID NO:14; polypeptides encoded by nucleic acid residues substantially similar to SEQ ID NO: 21; or polypeptides encoded by nucleic acid residues substantially similar to 355–957 in SEQ ID NO:13.

As used herein, a "BMP receptor kinase protein complex" is the combination of a BMP type I receptor and BMP receptor kinase protein BRK-3. The combination of the type I and BRK-3 receptors includes, but is not limited to, a combination of the type I and BRK-3 receptors in solution (e.g., as soluble fragments); a combination of the receptors (e.g., as soluble fragments) attached to a solid support; or a combination of the receptors (e.g., as full-length or incomplete fragments) within a cell membrane of transfected cells.

As used herein, "digit-removed BMP-2" and "DR-BMP-2" refer to a fragment of BMP-2 protein wherein the amino terminus of mature BMP-2 has been removed by mild trypsin digestion (B. B. Koenig et al., *Molecular and Cellular Biolog,* 14: 5961–5974 (1994)).

As used herein, "isolated", in reference to the receptor protein of the present invention or DNA sequences encoding said protein, means that the protein or DNA sequence is removed from the complex cellular milieu in which it naturally occurs, and said protein is expressible from said DNA sequence in a cell that does not naturally express it when operably linked to the appropriate regulatory sequences.

As used herein, "substantially similar" when used to define either amino acid or nucleic acid sequences, means that a particular subject sequence, for example, a sequence altered by mutagenesis, varies from a reference sequence by one or more substitutions, deletions, or additions, the net effect of which is to retain biological activity of the BRK-3 protein. Alternatively, nucleic acid sequences and analogs are "substantially similar" to the specific DNA sequence disclosed herein if the DNA sequences, as a result of degeneracy in the genetic code, encode an amino acid sequence substantially similar to the reference amino acid sequence. In addition, "substantially similar" means a receptor protein that will react with antibodies generated against the BRK-3 protein or peptides derived from the protein sequence of BRK-3.

As used herein, "biologically active" means that a particular molecule shares sufficient amino acid sequence similarity with the embodiments of the present invention disclosed herein to be capable of binding detectable quantities of BMP-2 or BMP-4, or transmitting a BMP-2 or BMP-4 stimulus to a cell, for example, as a component of a hybrid receptor construct. Preferably, a biologically active BRK-3 receptor complex within the scope of the present invention means the receptor protein kinase complex is capable of binding [$^{125}$I]-BMP-4 with nanomolar or subnanomolar affinity ($K_d$ approximately equal to $10^{-9}$M). Preferably, the affinity is from about $1\times10^{-12}$M to $1\times10^{-9}$M, with a proportion of binding sites exhibiting a $K_d$ less than $10^{-12}$M.

As used herein, "operably linked" refers to a condition in which portions of a linear DNA sequence are capable of influencing the activity of other portions of the same linear DNA sequence. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous in reading frame.

As used herein, "ATCC" means American Type Culture Collection, Rockville, Md.

As used herein, "bone morphogenetic protein 2" or "BMP-2" means a peptide encoded by a DNA sequence contained in ATCC No. 40345 (see ATCC/NIH REPOSITORY CATALOGUE OF HUMAN AND MOUSE DNA PROBES AND LIBRARIES, sixth Edition, 1992, p. 57, hereinafter "ATCC/NIH REPOSITORY CATALOGUE"). Isolation of BMP-2 is disclosed in U.S. Pat. No. 5,013,649, Wang, Wozney and Rosen, issued May 7, 1991; U.S. Pat. No. 5,166,058, Wang, Wozney and Rosen, issued Nov. 24, 1992; and U.S. Pat. No. 5,168,050, Hammonds and Mason, issued Dec. 1, 1992; each of which is incorporated herein by reference.

As used herein, "bone morphogenetic protein 4" or "BMP-4" means a peptide encoded by a DNA sequence contained in ATCC No. 40342 (see ATCC/NIH REPOSITORY CATALOGUE). Isolation of BMP-4 is disclosed in U.S. Pat. No. 5,013,649, Wang, Wozney and Rosen, issued May 7, 1991, incorporated herein by reference.

As used herein, "bone morphogenetic protein 7" or "BMP-7" means a peptide encoded by a DNA sequence contained in ATCC No. 68020 and ATT 68182 (see ATCC/NIH Repository Catalogue), where the cDNA in ATCC 68182 is claimed to contain all of the nucleotide sequences necessary to encode BMP-7 proteins. Isolation of BMP-7 is disclosed in U.S. Pat. No. 5,141,905, issued Aug. 25, 1992, to Rosen, et al., which is incorporated herein by reference.

As used herein, "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences (introns) which are typically present in eukaryotic genes. Genomic DNA containing the relevant sequences could also be used. Sequences of non-translated DNA may be present 5' or 3' from the open reading frame, where the same do not interfere with manipulation or expression of the coding regions. DNA sequences encoding the proteins provided by this invention can be assembled from cDNA fragments and short oligonucleotide linkers, or from a series of oligonucleotides, to provide a synthetic gene which is capable of being expressed in a recombinant transcriptional unit.

As used herein, "recombinants" means that a protein is derived from a DNA sequence which has been manipulated in vitro and introduced into a host organism.

As used herein, "microbial" refers to recombinant proteins made in bacterial, fungal (e.g., yeast), or insect expression systems.

As used herein, "recombinant expression vector" refers to a DNA construct used to express DNA which encodes a desired protein (for example, BRK-3) and which includes a transcriptional subunit comprising an assembly of 1) genetic elements having a regulatory role in gene expression, for example, promoters and enhancers, 2) a structural or coding sequence which is transcribed into mRNA and translated into protein, and 3) appropriate transcription and translation initiation and termination sequences. Using methodology well known in the art, recombinant expression vectors of the present invention can be constructed. Possible vectors for use in the present invention include, but are not limited to: for mammalian cells, pJT4 (discussed further below), pcDNA-1 (Invitrogen, San Diego, Calif.) and pSV-SPORT 1 (Gibco-BRL, Gaithersburg, Md.); for insect cells, pBlueBac III or pBlueBacHis baculovirus vectors (Invitrogen, San Diego, Calif.); and for bacterial cells, pET-3 (Novagen, Madison, Wis.). The DNA sequence coding for a BRK-3 protein receptor kinase of the present invention can be present in the vector operably linked to regulatory elements.

The present invention relates to a host cell co-transfected with an expression vector comprising a DNA sequence that codes for BMP receptor kinase protein BRK-3 and an expression vector comprising a DNA sequence that codes for a BMP type I receptor kinase protein. In one embodiment, the expression vector for the BRK-3 protein comprises a DNA sequence coding for the h-BRK-3 receptor protein, or a soluble or incomplete fragment thereof. (The DNA can be genomic or cDNA.) Preferably the h-BRK-3 protein is coded for by the nucleic acid sequence SEQ ID NO: 1; the soluble fragment thereof is preferably coded for by the nucleic acid sequence SEQ ID NO: 5, the incomplete receptor fragment is preferably coded for by nucleic acid SEQ ID NO:23. In another embodiment, the expression vector for the BRK-3 protein comprises a DNA sequence coding for the t-BRK-3 protein. (The DNA sequence can be genomic DNA or cDNA.) Preferably the DNA sequence is SEQ ID NO:3. In another embodiment, the expression vector for the BRK-3 protein comprises a DNA sequence coding for the m-BRK-3 protein, or a soluble or incomplete fragment thereof. (The DNA sequence can be genomic DNA or cDNA.) Preferably the m-BRK-3 protein is coded for by the DNA sequence SEQ ID NO:7; the soluble fragment is preferably coded for by the DNA sequence SEQ ID NO:9; the incomplete fragment is preferably coded for by the DNA SEQ ID NO:25.

In a preferred embodiment of the present invention, the host cells of the present invention are co-transfected with the plasmid construct pJT6-mBRK-3L and the plasmid construct pJT4-J159F [BRK-1] or plasmid construct pJT3-BRK-2 [BRK-2], thereby resulting in co-expression of m-BRK-3 and BRK-1, or m-BRK-3 and BRK-2, respectively. In another preferred embodiment, the host cells of the present invention are co-transfected with the plasmid construct pJT6-mBRK-3S and the plasmid construct pJT4-J159F [BRK-1] or plasmid construct pJT3-BRK-2 [BRK-2], thereby resulting in co-expression of m-BRK-3 and BRK-1, or m-BRK-3 and BRK-2, respectively. In another preferred embodiment, mammalian host cells are co-transfected with the plasmid construct, pJT4-hBRK3T and the plasmid construct pJT6-J159F [BRK-1] or plasmid construct pJT3-BRK-2 [BRK-2], thereby resulting in co-expression of t-BRK-3 and BRK-1, or t-BRK-3 and BRK-2, respectively. Transfection with the recombinant molecules can be effected using methods well known in the art.

As used herein, "host cell" means a cell comprising a recombinant expression vector described herein. Host cells may be stably transfected or transiently transfected within a recombinant expression plasmid or infected by a recombinant virus vector. The host cells include prokaryotic cells, such as *Escherichia coli,* fungal systems such as *Saccharomyces cerevisiae,* permanent cell lines derived from insects such as Sf-9 and Sf-21, and permanent mammalian cell lines such as Chinese hamster ovary (CHO) and SV40-transformed African green monkey kidney cells (COS).

In one embodiment, the present invention relates to a method that is useful for identifying compounds capable of binding to a BMP receptor kinase protein. In another embodiment, the invention relates to a method that is useful for determining the concentration of a BMP receptor ligand (e.g., BMP-2, BMP-4, or BMP-7, or another as yet identified BMP receptor ligand) in a clinical sample. In each of these methods, a sample comprising a putative ligand or a known ligand is introduced to a BMP receptor kinase protein complex, wherein the receptor complex is comprised of a BMP type I receptor kinase protein and BMP receptor kinase protein BRK-3. Preferably, the BRK-3 receptor kinase protein is h-BRK-3, having an amino acid sequence SEQ ID NO:2, or the soluble fragment thereof having an amino acid sequence SEQ ID NO:6 or the incomplete fragment thereof having an amino acid sequence SEQ ID NO:24. Also preferred is the receptor protein m-BRK-3 having an amino acid sequence SEQ ID NO:8, or the soluble fragment thereof having an amino acid sequence SEQ ID NO:10 or the incomplete fragment thereof having an amino acid sequence SEQ ID NO:26. Also preferred is the receptor protein t-BRK-3 having an amino acid sequence SEQ ID NO:4.

For example, BMP concentration in a sample can be determined by radioreceptor assay, in which unlabeled BMP in the sample competes with labeled BMP for binding to the BRK-3 receptor complex. As the amount of BMP in the sample increases, it reduces the amount of labeled BMP which is able to bind to the receptor protein complex comprising BRK-3 and the type I receptor. Comparison with a standard curve prepared with known concentrations of unlabeled BMP allows accurate quantitation of BMP concentration in the sample. Labeling of BMP is preferably done by iodination with [$^{125}$I]NaI. BRK-3 can be expressed in the outer membrane of a stable cell line which also expresses the BMP type I receptor kinase, or supplied as a soluble fragment in solution with a soluble type I receptor fragment, or as a soluble fragment covalently attached to a solid support in conjunction with a type I receptor covalently attached to a solid support. To perform the assay, unlabeled BMP from the sample and labeled BMP compete for binding to the receptor until equilibrium is reached. The receptor-BMP complex is then isolated from free ligand, for example by washing (in the case of an adherent cell line), rapid filtration or centrifugation (in the case of a nonadherent cell line or receptor bound to a solid support), or precipitation of the receptor-ligand complex with antibodies, polyethylene glycol, or other precipitating agent followed by filtration or centrifugation (in the case of a soluble receptor). The amount of labeled BMP in the complex is then quantitated, typically by gamma counting, and compared to known standards. These methods have been described in the literature using other receptors (M. Williams, *Med. Res. Rev.,* 11: 147–184 (1991); M. Higuchi and B. B. Aggarwal, *Anal Biochem.,* 204: 53–58 (1992); M. J. Cain, R. K. Garlick and P. M. Sweetman, *J. Cardiovasc. Pharm.,* 17: S150–S151 (1991); each of which are incorporated herein by reference), and are readily adapted to the present BRK-3 receptor/BMP system. Such a radioreceptor assay can be used for diagnostic purposes for quantitation of BMP in clinical samples, where such quantitation is necessary.

The methods of the present invention is also useful in high-throughput screens to identify compounds capable of binding to BRK-3, or a homologous receptor protein, that is complexed to a BMP type I receptor kinase protein. In such a method, the higher the affinity of the compound for the BRK-3/type I complex, the more efficiently it will compete with the tracer for binding to the complex, and the lower the counts in the receptor-ligand complex. In this case, one compares a series of compounds within the same concentration range to see which competed for receptor binding with the highest affinity.

This invention is useful for determining whether a ligand, such as a known or putative drug, is capable of binding to and/or activating the receptors encoded by the DNA molecules of the present invention. Transfection of said DNA sequence into the cell systems described herein provides an assay system for the ability of ligands to bind to and/or activate the receptor complex encoded by the isolated DNA molecules. Recombinant cell lines, such as those described herein, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Soluble receptors derived from the ligand binding domain of the receptor can also be employed in high-throughput screening of drug candidates. Functional assays of intracellular signaling can act as assays for binding affinity and efficacy in the activation of receptor function. In addition, the recombinant cell lines may be modified to include a reporter gene operably linked to a response element such that a signal sent by the receptor turns on the reporter gene. Such a system is especially useful in high throughput screens directed at identification of receptor agonists. These recombinant cell lines constitute "drug discovery systems", useful for the identification of natural or synthetic compounds with potential for drug development. Such identified compounds could be further modified or used directly as therapeutic compounds to activate or inhibit the natural functions of the receptor encoded by the isolated DNA molecule.

The soluble receptor protein complex of the present invention can be administered in a clinical setting using methods such as by intraperitoneal, intramuscular, intravenous, or subcutaneous injection, implant or transdermal modes of administration, and the like. Such administration can be expected to provide therapeutic alteration of the activity of the BMPs.

The nucleotide sequences disclosed herein, SEQ ID NO:3 and SEQ ID NO:1, represent the sequence of the DNA that codes for t-BRK-3 and h-BRK-3, respectively, isolated from human skin fibroblasts. SEQ ID NO:7 represents the DNA sequence coding for m-BRK-3 receptor protein from mouse NIH3T3 cells. These sequences could be readily used to obtain the cDNA for BRK-3 from other species, including, but not limited to, rat, rabbit, Drosophila, and Xenopus. These sequences could also readily be used to obtain the cDNA for other BMP type II receptors from mouse and other species listed above which are capable of binding BNIs in a complex with the type I receptors. These cDNA sequences can also be readily used to isolate the genomic DNA for BRK-3. This would permit analysis of the regulatory elements controlling receptor gene expression, which may offer new opportunities for therapeutic intervention and disease diagnosis. The nucleotide sequences are also useful to determine the distribution of the BRK-3 receptor in normal tissues and in disease states, which allows an assessment of its physiological role in vivo.

The present invention further relates to a method for determining whether a test compound produces a signal upon binding to a BMP receptor protein complex. Such a method comprises employing the BMP receptor protein complex in a protein phosphorylation assay. Protein phosphorylation assays are generally known in theart. Hardie, D. G., "Protein Phosphorylation A Practical Approach", IRL Press: Oxford, N.Y., Tokyo, (1993), incorporated herein by reference, provides a general overview phosphorylation assays. The method for determining whether a test compound produces signal upon binding to the BMP receptor protien complex comprises (a) labeling BMP receptor protein complex expressing cells with $^{32}p$, wherein the cells have been transformed with a DNA sequence coding for BMP receptor kinase protein BRK-3 and a DNA sequence coding for a BMP type I receptor kinase protein; (b) culturing (i) a first set of the cells in the presence of the test compound, and (ii) a second set of the cells in the absence of the test compound; (c) quantitating via autoradiography any phosphorylated proteins produced from step (b); and (d) comparing the amount of phosphorylated proteins quantitated in step (c) from the first set of cells to the amount of phosphorylated proteins quantitated in step (c) for the second set of cells.

For purposes of illustrating a preferred embodiment of the present invention, the following non-limiting examples are discussed in detail.

EXAMPLE 1

Generation of PCR Fragments

In order to generate a PCR fragment of type II receptors related to the TGF-β type II receptor, primers shown in FIG. 1 are designed from the kinase domains of the TGF-β type II receptor. For the first round of PCR, the primers are TSK-1, derived from kinase domain II, and TSK-2, derived from kinase domain VIII. The template DNA consists of cDNA prepared from mRNA isolated from human skin fibroblasts from a 9 month old male. The PCR reaction, carried out in a total volume of 50 μl, contains approximately 0.2 μg of this cDNA, primers TSK-1 and TSK-2 at a concentration of 15 μM, stocks of all four deoxynucleotides at a concentration of 0.2 mM each, 1.5 unit of DNA polymerase from *Thermus thermophilus* (hereafter, Tth polymerase) (Toyobo, Osaka, Japan) and reaction buffer for the Tth polymerase (Toyobo, Osaka, Japan). After an initial melting period of 1 min at 94° C., the temperature cycle is carried out as follows for 35 cycles: melting, 92° C. for 40 sec; annealing, 48° C. for 40 sec; extension, 75° C. for 90 sec. After the 35th cycle, the reaction is held at 75° C. for an additional 5 min to complete the extension.

Several bands are amplified, including some in the area of 470 base pairs (bp) corresponding to the predicted sequence length of a type I receptor homologous to the TGF-β type II receptor. Accordingly, fragments in this size range are recovered from an agarose gel using QIAEX (Qiagen, Chatsworth, Calif.; a kit for gel purification of DNA fragments, including activated silica spheres and buffers) according to the manufacturer's instructions, then resuspended in 10 mM Tris, pH 8.0, 1 mM EDTA (TE) in a volume of 20 μl.

To reduce the background from fragments amplified from cDNAs not related to the TGF-β type II receptor, a second round of PCR is carried out using "nested" primers based on conserved regions of the TGF-β type II receptor located within the 470 bp region amplified in the first round. The nested primers are AVR-5, derived from kinase domain IV of the TGF-β type II receptor, and TSK-4, derived from kinase domain VIB (FIG. 1). The template consists of an aliquot (0.5 μl) of the PCR fragments isolated from the first round of PCR. To this is added the primers AVR-5 (5 μM) and TSK-4 (15 μM), all four deoxynucleotides (0.2 mM each), 1.5 units of Tth DNA polymerase, and reaction buffer for the Tth DNA polymerase, in a total volume of 50 μl. The temperature cycle program is executed exactly as described above for the first round of PCR. Agarose gel electrophoresis of the PCR reaction products shows amplification of a band in the range of 300 bp, as expected. This fragment is isolated using QIAEX.

In order to subclone the PCR product of the second PCR reaction, the purified fragment is phosphorylated using polynucleotide kinase and ligated to the cloning vector pGEM7Zf (+) (Promega, Madison, Wis.) which has previously been cut with Sma I and dephosphorylated. The ligation mix is used to transform *E. coli* XL1-Blue (Stratagene, La. Jolla, Calif.). When the transformation mix is plated on agar containing isopropyl-β-D-thiogalactoside (IPTG) and 5-bromo-4-chloro-3-indolyl-β-D-galactoside (X-gal), colonies are obtained which lack blue color, indicating the presence of an insert. Plasmid DNA is prepared from a selection of these colonies. Three of the candidate plasmids, designated HSK7-1, HSK7-2, and HSK7-4 are found to have inserts of the expected size (300 bp). Upon sequencing of the inserts, the 300 bp insert from HSK7-2 is found to encode a portion of a novel kinase that is predicted to be a novel member of the TGF-β receptor superfamily. Accordingly, the HSK7-2 PCR fragment is used as a probe to isolate the full-length receptor clone.

EXAMPLE 2

Isolation of Human t-BRK-3 cDNA

In order to locate the cDNA corresponding to the 300 bp insert in HSK7-2, a cDNA library is constructed from the same mRNA used to isolate the PCR fragment. This is accomplished using the SUPERSCRIPT Choice System (Life Technologies, Gaithersburg, Md.; a kit for cDNA synthesis, including primers, adapters, SUPERSCRIPT II RNAse H⁻ Reverse Transcriptase (Life Technologies, Gaithersburg Md.; a modified form of reverse transcriptase from Moloney murine leukemia virus), enzymes, nucleotides, buffers, and gel filtration columns) according to the manufacturer's instructions, except that 180 units of RNase inhibitor (Takara, Kyoto, Japan) is added to the first strand synthesis. The template is mRNA (4 μg) from human skin fibroblasts from a 9 month old male. A total of 4 μg of cDNA is obtained after first and second strand synthesis. This is followed by the addition of Eco RI adapters (supplied with the kit) which contain internal Not I and Sal I sites. The Eco RI-adapted cDNA is then phosphorylated and subjected to size fractionation according to the manufacturer's instructions, using gel filtration columns provided with the kit.

The size fractionated cDNA is ligated into the Eco RI site of the phage λgt10, and packaged in vitro with GIGAPACK II Gold Packaging Extract (Stratagene, La Jolla, Calif.; a restriction-minus in vitro packaging extract for high-efficiency construction of cDNA libraries in λ phage)

according to the manufacturer's instructions. A total of 8.1×10⁵ phages are obtained.

The library is screened on ten HYBOND Nylon membranes (Amersham, Arlington Heights, Ill.; nylon membranes optimized for immobilization of nucleic acids), at a density of 1×10⁵ plaques/filter. The insert from HSK7-2 is labeled with the MULTIPRIME DNA Labeling System (Amersham, Arlington Heights, Ill.; a kit for random primer labeling of DNA, including Klenow DNA polymerase, primers, and buffers) according to the manufacturer's instructions. The labeled probe is allowed to hybridize to the library filters in 50% formamide, 6× SSPE (1×SSPE=0.14 M NaCl, 8 mM sodium phosphate, 0.08 mM EDTA, pH 7.7), 5× Denhardt's solution (1×Denhardt's=0.02% Ficoll type 400, 0.02% polyvinylpyrrolidone, 0.02% BSA), 0.5% sodium dodecyl sulfate (SDS), and 100 µg/ml denatured salmon sperm DNA at 42° C. for 12 hr. The blot is then washed in 2×SSPE, 0.1% SDS three times at room temperature (15 minutes each), followed by a 1 hr wash at 42° C.

After three rounds of screening, 3 independent clones are obtained. One of the clones, designated HSK723, is found to encode the same sequence as the HSK7-2 insert. Complete DNA sequence is obtained for this clone. The cDNA from this clone is designated t-BRK-3.

EXAMPLE 3 t-BRK-3 Sequence Analysis

The DNA sequence of this t-BRK-3 clone is shown in SEQ ID NO:3, and the deduced protein sequence of t-BRK-3 in SEQ ID NO:4. The t-BRK-3 open reading frame derived from clone HSK723 encodes a protein of at least 583 amino acids. No stop codon is observed to be located in-frame in the 3' region of the HSK723 cDNA, indicating that this clone is incomplete at the 3' end. It is thus designated t-BRK-3.

The deduced protein sequence of t-BRK-3 shown in SEQ ID NO:4 is searched against all translated protein sequences in GenBank Release 84.0, dated Aug. 15, 1994, using a standard Needleman-Wunsch algorithm (S. B. Needleman and C. D. Wunsch, *J. Mol. Biol.* 48: 443–453 (1970)), and is found to represent a novel sequence.

Analysis of the predicted protein sequence reveals a predicted structure of a TGF-β type II superfamily member transmembrane serine/threonine kinase. The predicted single transmembrane region encompasses residues 151–172 in SEQ ID NO:4. Three potential N-linked glycosylation sites are located at amino acid residues 55, 110, and 126 in the predicted extracellular domain. Amino acids 116–123 in SEQ ID NO:4 contain the cluster of cysteine residues called the "cysteine box" that is a characteristic of receptors for ligands of the TGF-β superfamily. The cysteine box of t-BRK-3 is identical in 6 of 8 amino acid residues to the cysteine box of the DAF-4 type II receptor for BMP-2 and BMP-4. However, the overall sequence identity of t-BRK-3 to DAF-4 in the extracellular domain is only 7.1%.

Amino acids 200–504 (in SEQ ID NO: 4) in the predicted cytoplasmic region of t-BRK-3 contains all of the consensus sequences that characterize a protein kinase domain with predicted specificity for serine/threonine residues (S. K. Hanks, A. M. Quinn, and T. Hunter, *Science*, 241: 42–52 (1988)).

EXAMPLE 4

Construction of Expression Vectors for t-BRK-3, BRK-1, BRK-2, and DAF-4

In order to express t-BRK-3 in mammalian cells, it is subcloned into the vector pJT4, designed for transient expression. The pJT4 vector, optimized for transient expression in COS cells, includes the cytomegalovirus early promoter and enhancer, which gives very efficient transcription of message; an "R" element from the long terminal repeat of the human T-cell leukemia virus-1, which has been shown to increase expression levels further; an intron splice site from SV40, which is believed to enhance message stability; a multiple cloning site; a polyadenylation signal derived from SV40, which directs the addition of a poly A tail to the message, as is required for most eukaryotic mRNA; and the SV40 origin of replication, which permits the replication of the plasmid to extremely high copy number in cells which contain the SV40 large T antigen, such as COS cells. In addition, for manipulation and amplification of the vector in bacteria, the vector contains an *E. coli* origin of replication and an ampicillin resistance gene. Insertion of the truncated human BRK-3 cDNA into pJT4 is accomplished as follows.

Since no stop codon had been identified in the 3' region of the kinase domain, PCR is performed to insert a stop codon to permit translation of the protein. Accordingly, a PCR primer is designed to insert two stop codons after nucleotide 2028 in SEQ ID NO:3, thus terminating the kinase after Ile 540 in SEQ ID NO: 4. This is chosen to correspond to the length of the activin type II receptor (L. S. Mathews and W. V. Vale, *Cell*, 65: 973–982 (1991)), so that it should be sufficient for proper folding of the kinase domain. The stop codons are followed by a Kpn I site. The complete sequence of the primer (which includes the reverse complement of nucleotides 2013–2028 in SEQ ID NO:3) is 5' ACG CGG TAC CTC ACT AAA TTT TTG GCA CAC GC 3'. A second primer is designed as an exact match to the t-BRK-3 sequence in the area of the Afl III site (nucleotides 1618–1637 in SEQ ID NO:3), having the sequence 5' GTA GAC ATG TAT GCT CTT GG 3'. The template for the reaction is clone HSK723, described in example 2, which contains the cDNA for t-BRK-3 in BLUESCRIPT II SK (+) (Stratagene, La Jolla, Calif.; a 2.96 kb colony-producing phagemid derived from pUC 19).

PCR is carried out using the GENE AMP PCR Kit with AMPLITAQ DNA Polymerase (Perkin Elmer, Norwalk, Conn.; a kit containing components necessary for amplification of DNA using the polymerase chain reaction, including AMPLITAQ, a recombinant modified form of the DNA polymerase from *Thermus aquaticus* (Perkin-Elmer, Norwalk Conn.), nucleotides, and buffers), according to the manufacturer's instructions, using a GENE AMP PCR System 9600 Thermocycler (Perkin Elmer, Norwalk, Conn.). An initial melting at 95° C. for 5 min is followed by 20 cycles of the following program: melting at 95° C. for 1 min, annealing at 50° C. for 1 min, and extension at 72° C. for 1 min. After the last cycle, the temperature is held at 72° C. for an additional 2 min to complete extension.

Figure 2:
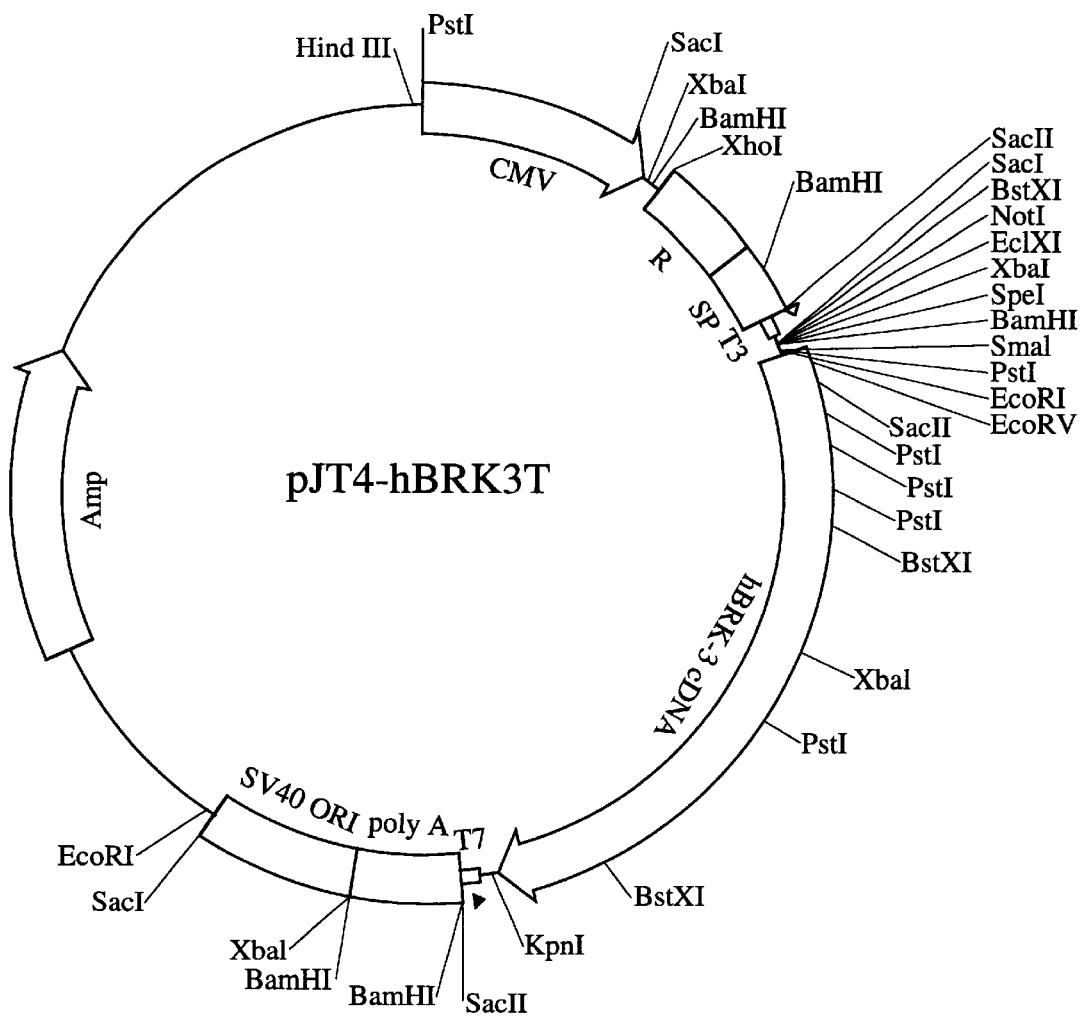
FIG. 2 shows the construct pJT4-hBRK3T, used for transient mammalian expression of t-BRK-3. CMV, cytomegalovirus early promoter/enhancer; R, the "R" element from the long terminal repeat of human T-cell leukemia virus-1; SP, an intron splice site from the SV40 virus; T3, promoter region from the T3 bacteriophage; T7, promoter region from the T7 bacteriophage; poly A, region from the SV40 virus directing polyadenylation of the message; SV40 ORI, origin of replication from the SV40 virus; Amp, ampicillin resistance gene for selection in *E. coli*.

The resulting amplified band, at the expected size of 400 bp, is isolated from an agarose gel and digested with Afl III and Kpn I. Meanwhile, the cDNA for t-BRK-3 is digested with Eco RV and Afl III, and the vector pJT4 is digested with Eco RV and Kpn I. These three isolated fragments are ligated in a single step to give the construct pJT4-hBRK3T, shown in FIG. 2. To confirm that no errors are introduced during PCR, the region from the Afl III site to the KpnI site at the 3' end is sequenced using the TAQ DYE DEOXY Terminator Cycle Sequencing Kit (Applied Biosystems, Foster, Calif.; kit containing components for automated DNA sequencing using the dideoxy terminator method, including AMPLITAQ, nucleotide mix, dye-labeled dideoxy nucleotide terminators, and buffers) and an Applied Biosystems Model 373A Automated DNA Sequencer. No errors are found.

To determine the effects of co-expression of t-BRK-3 with type I BMP receptors, it is necessary to co-express the cDNA for t-BRK-3 with the cDNA for BRK-1 or the cDNA for BRK-2. The DNA sequence for mouse BRK-1 is shown in SEQ ID NO: 11, and the deduced amino acid sequence for mouse BRK-1 is shown in SEQ ID NO: 12. The DNA sequence for chicken BRK-2 is shown in SEQ ID NO: 13, and the deduced protein sequence shown for chicken BRK-2 is shown in SEQ ID NO: 14.

Figure 3:
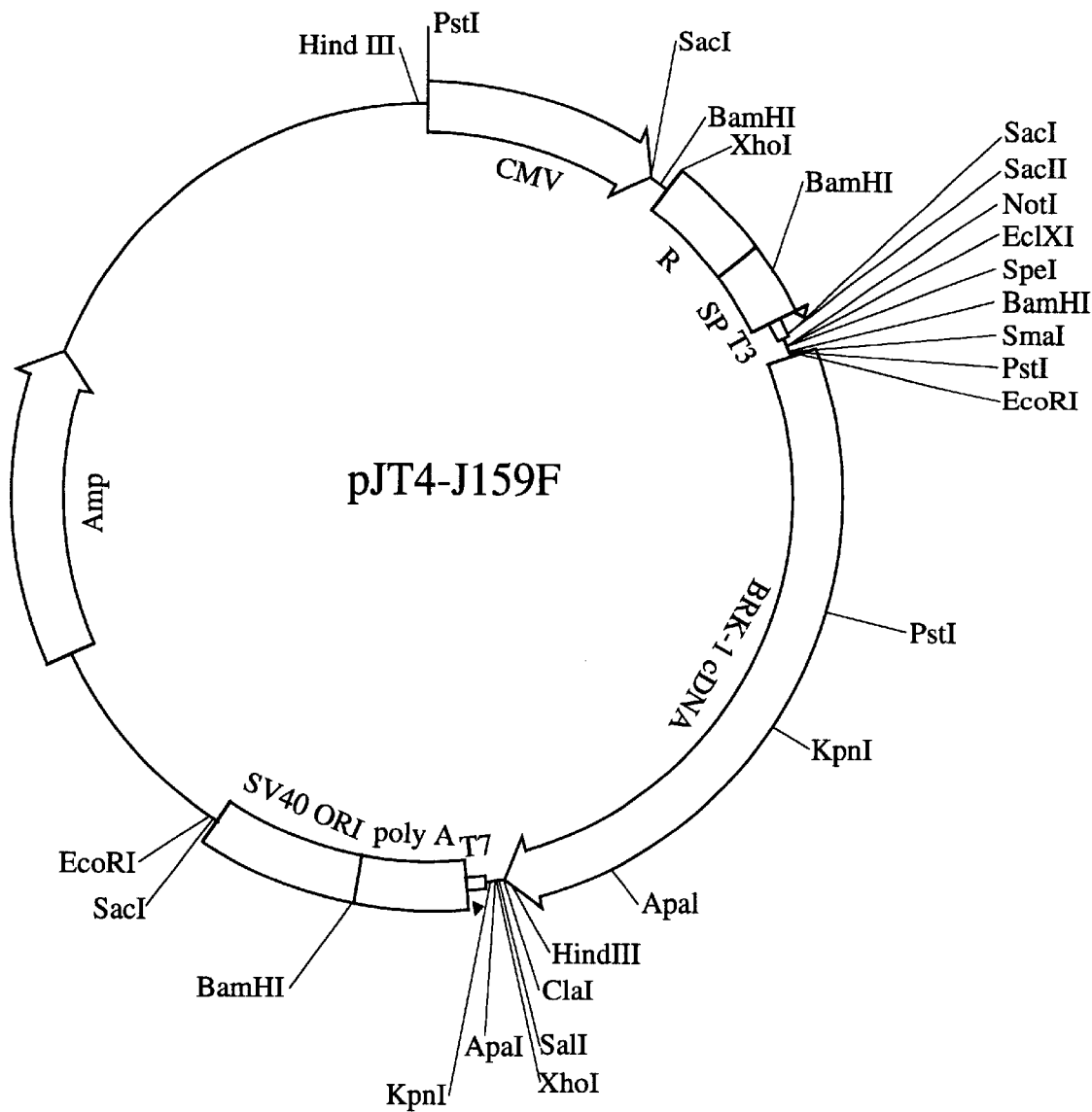
FIG. 3 shows the construct pJT4-J159F, used for transient mammalian expression of BRK-1. Abbreviations are the same as those in FIG. 2.

For mammalian expression of BRK-1, the plasmid pJT4-J159F is used. Construction of this plasmid is described in U.S. Ser. No. 08/158,735, filed Nov. 24, 1993 by Cook, et al. and B. B. Koenig et al., *Molecular and Cellular Biology* 14: 5961–5974 (1994); ATCC 69457. Briefly, the construct containing the BRK-1 cDNA subcloned in BLUESCRIPT SK (−) is linearized with the restriction endonuclease Alf III, and the overhanging end filled in using DNA Polymerase I Klenow fragment. The linearized plasmid is then digested with Not I, liberating the insert from the plasmid. The insert is then subcloned into the pJT4 expression vector at the Not I and EcoRV sites. The blunt end generated by the Klenow reaction is compatible with the EcoRV site, which is also a blunt end; ligation eliminates the Eco RV site. The construct pJT4-J159F is shown in FIG. 3.

Figure 4:
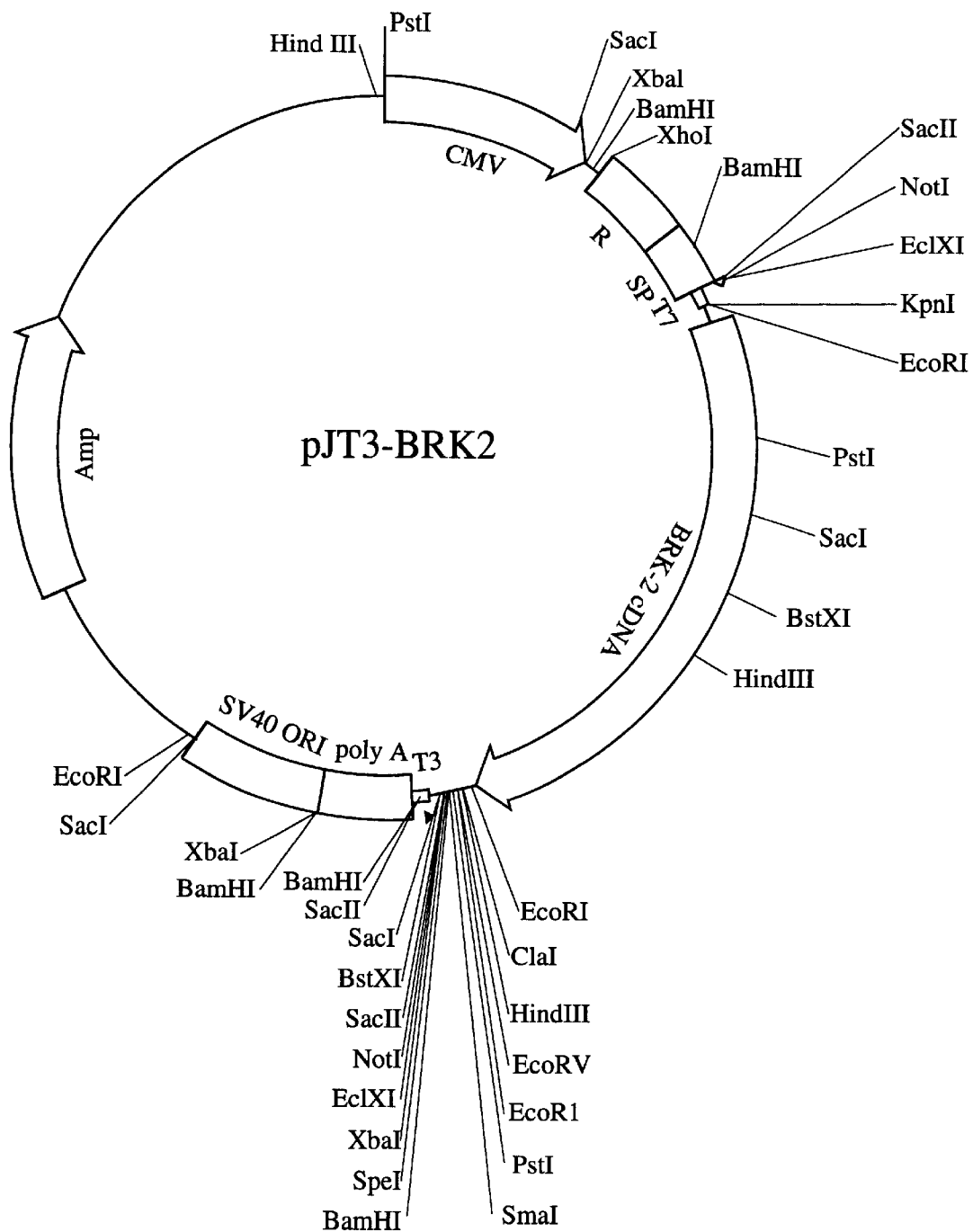
FIG. 4 shows the construct pJT3-BRK2, used for transient mammalian expression of BRK2. Abbreviations are the same as those in FIG. 2.

For mammalian expression of BRK-2, its cDNA is subcloned into the vector pJT3. This vector is identical to pJT4, described in this example, except that the multiple cloning site is in the opposite orientation, and an additional Not I site is present at the 5' end of the multiple cloning site. The cDNA for BRK-2 (see S. Sumitomo, et al., *DNA Sequence* 3: 297–302 (1993)), originally obtained in the vector pRc/CMV (Invitrogen, San Diego, Calif.; a mammalian expression vector), is excised by digestion with Kpn I and Xho I. It is subcloned into pJT3 at the Kpn I and Sal I sites. This regenerates a Kpn I site at the 5' end of BRK-2, while the Xho I and Sal I sites are destroyed. The resulting construct is designated pJT3-BRK-2 and is shown in FIG. 4.

Figure 5:
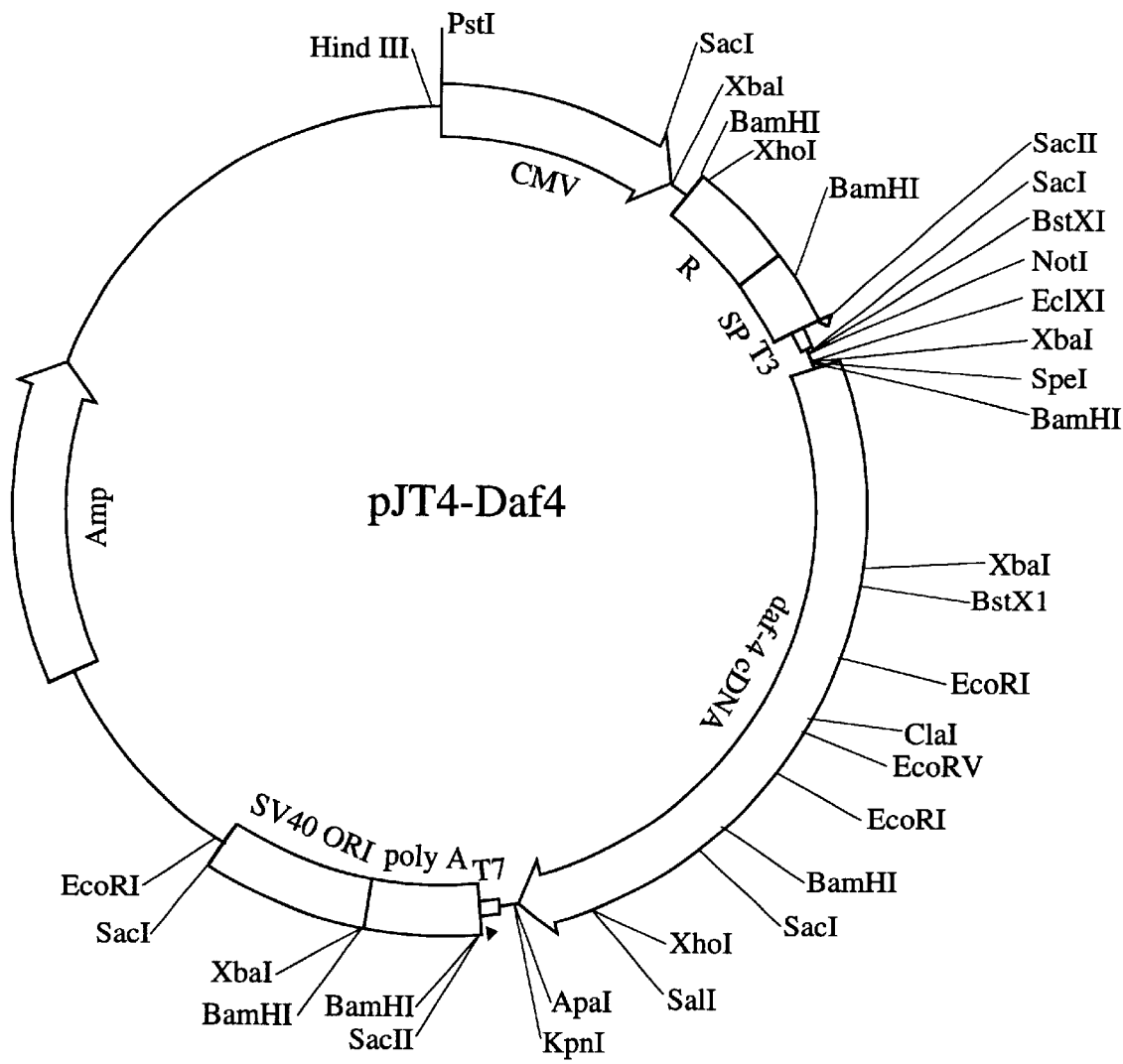
FIG. 5 shows the construct pJT4-Daf4, used for transient mammalian expression of the *C. elegans* receptor DAF-4. Abbreviations are the same as those in FIG. 2.

For mammalian expression of DAF-4, the type II BMP receptor from *Caenorhabditis elegans* (M. Estevez, L. Attisano, J. L. Wrana, P. S. Albert, J. Massagué, and D. L. Riddle, *Nature,* 365: 644–9 (1993), the cDNA is obtained in BLUESCRIPT II and subcloned into pJT4 as follows. A 2.4 kb fragment containing the daf-4 cDNA is excised by digestion with Dra I and Apa I. This fragment is subcloned into pJT4 at the Sma I and Apa I site. The Apa I site is regenerated, while the Dra I and Sma I sites are destroyed. This construct is designated pJT4-Daf4, and is shown in FIG. 5.

For mammalian expression of m-BRK-3, see Example 10, below.

EXAMPLE 5

Mammalian Expression of t-BRK-3, BRK-1, BRK-2, and DAF-4

Transient expression of BRK-3 in mammalian cells using pJT4-hBRK3T is carried out in COS-7 cells (ATCC CRL 1651) using electroporation or COS-1 cells (ATCC CRL 1650) using DEAE Dextran (Pharmacia Biotech, Piscataway, N.J.).

COS-7 cells are grown to confluence in Dulbecco's Modified Eagle (DME) high glucose media supplemented with 10% fetal bovine serum (Hyclone, Logan, Utah), nonessential amino acids (GIBCO, Gaithersburg, Md.), and glutamine, then trypsinized to release cells from the plate. The detached COS-7 cells are pelleted in a tabletop centrifuge, then resuspended in fresh media at a concentration of $6.25 \times 10^6$ cells/ml. The cell suspension ($5 \times 10^6$ cells, 0.8 ml) is transferred to the cuvette of a BioRad GENE PULSER electroporation system (BioRad, Hercules, Calif.). The purified plasmid containing the receptor DNA of interest (10 μg for pJT4-J159F and pJT3-BRK2 and/or 20 μg for pJT4-hBRK3T) is added to the cuvette, and the cells subjected to electoporation at 4.0 kV/cm, with a capacitance of 25 μFd. Cells are then plated (400,000 cells per well for 12 well plates and $5 \times 10^6$ cells for 100 mm plates) and allowed to recover. Fresh media is supplied after 24 hr. At 48 hr, cells are ready to be tested for binding of BMP-4.

For transient expression of BMP receptors in COS-1 cells, the cells are grown to approximately 50%–80% confluence in DME high glucose media supplemented with 10% fetal bovine serum (HyClone, Logan, Utah), nonessential amino acids, and glutamine in 100 mm plates. The cells are washed twice with 37° C. serum-free DME media, after which 4 ml of DNA mixture is added to each 100 mm plate. The DNA mixture contains DME, 10% Nu-Serum (Collaborative-Biomedical Products, Bedford, Mass.), 400 μg/ml DEAE-Dextran (Pharmacia, Piscataway, N.J.), 0.1 mM chloroquine (Sigma, St. Louis, Mo.), and the cDNAs of interest: for t-BRK-3, 16 μg pJT4-hBRK3T; for BRK-1, 8 μg pJT4-J159F; for BRK-2, 8 μg pJT3-BRK2; for DAF-4, 16 μg pJT4-Daf4. The cells are then incubated at 37° C. with the DNA mixture for 3 hr. The solution is aspirated and the cells are incubated with 4 ml of a solution containing 10% dimethylsulfoxide (DMSO) in Dulbecco's phosphate buffered saline without calcium or magnesium (PBS; Life Technologies, Gaithersburg, Md.). After 2 min, the DMSO solution is aspirated, the cells are washed with the growth media described above, and fresh media is returned to the plates. The transfected cells are split into 12 well plates 24 hr post transfection for whole cell binding or cross linking. After 48 to 68 hr the cells are suitable for binding analysis.

EXAMPLE 6

Generation of the Radiolabeled BMP-4 Ligand

[$^{125}$I]-BMP-4 is prepared using IODOBEADS (Pierce, Rockford, Ill.; immobilized chloramine-T on nonporous polystyrene beads). Lyophilized BMP-4 (2 μg) is taken up in 50 μl of 10 mM acetic acid and added to 450 μl of phosphate-buffered saline (PBS) (Sigma, St. Louis, Mo.) on ice. To the tube is added 500 μCurie of $^{125}$I (Amersham, Arlington Heights, Ill.) (2200 Ci/mmol) in 5 μl, and one IODOBEAD. The reaction is incubated on ice for 10 min with occasional shaking. The reaction is then terminated by removal of the reaction from the IODOBEAD. To remove unreacted $^{125}$I, the mixture is applied to a PD-10 gel filtration column (Pharmacia, Piscataway, N.J.) previously equilibrated in 10 mM acetic acid, 0.1 M NaCl, 0.25% gelatin. The resulting labeled protein is >95% precipitable by trichloroacetic acid, indicating that all $^{125}$I is protein bound, and has a typical specific activity of 4000 to 9000 Ci/mmol.

Alternatively, BMP-4 is labeled with $^{125}$I by the chloramine-T method (C. A. Frolik, L. M. Wakefield, D. M. Smith, and M. B. Sporn, *J. Biol. Chem.,* 259: 10995–11000 (1984)). BMP-4 (2 μg) is taken up in 5 μl of 30% acetonitrile, 0.1% trifluoracetic acid (TFA) plus an additional 5 μl of 1.5 M sodium phosphate, pH 7.4. Carrier free $^{125}$I (1 mCi, 9 μl) is added, together with 2 μl of a chloramine T solution (100 μg/ml). An additional 2 μl of the chloramine T solution is added at 2.0 min and at 3.5 min. After 4.5 minutes, the reaction is stopped by the addition of 10 μl of 50 mM N-acetyl tyrosine, 100 μl of 60 mM potassium iodide, and 100 μl of 11M urea, 1 M acetic acid. After a 3.5 minute incubation, unreacted iodine is removed on a PD-10 gel filtration column (Pharmacia, Piscataway, N.J.) run in 4 mM HCl, 75 mM NaCl, 1 mg/ml bovine serum albumin (BSA). The resulting labeled protein is >95% precipitable by trichloroacetic acid, indicating that all $^{125}$I is protein bound, and has a typical specific activity of 3000–8000 Ci/mmol.

EXAMPLE 7

Characterization of BMP-4 Binding to t-BRK-3

Binding of BMP-4 to t-BRK-3 can be demonstrated by whole cell binding of radiolabeled BMP-4, and by covalent crosslinking of radiolabeled BMP-4 to the receptor. These two methods are described in detail below.

a. Whole Cell Binding

COS-7 or COS-1 cells are transfected with pJT4-hBRK3T as described in example 5. After transfection, cells are seeded into 12 well plates and the binding experiments are carried out at 48 to 68 hr. At that time, cells are washed once with binding buffer (50 mM HEPES, pH 7.4, 128 mM NaCl, 5 mM KCl, 5 MM MgSO$_4$, 1.2 mM CaCl$_2$, 2 mg/ml BSA), then equilibrated in the same buffer at 4° C. for 30–60 min with gentle shaking. The buffer is then aspirated, and to each well is added 500 μl of binding buffer (4° C.), containing [$^{125}$I]-BMP-4 tracer (100–400 pM), as well as varying concentrations of unlabeled BMP-2, BMP-4, or other unlabeled ligand, depending on the assay. For determination of nonspecific binding, BMP-4 is added to the binding buffer at a final concentration of 10 to 50 nM. To prevent degradation of ligand during the incubation, a protease inhibitor cocktail is also added, to give a final concentration of 10 μg/ml leupeptin, 10 μg/ml antipain, 50 μg/ml aprotinin, 100 μg/ml benzamidine, 100 μg/ml soybean trypsin inhibitor, 10 μg/ml bestatin, 10 μ/ml pepstatin, and 300 μM phenylmethylsulfonyl fluoride (PMSF). The cells are incubated for 4 hr at 4° C. with gentle shaking. At the end of the incubation period, the buffer is aspirated, and the cells are rinsed 4 times with 1 ml washing buffer (50 mM HEPES, pH 7.4, 128 mM NaCl, 5 mM KCl, 5 mM MgSO4, 1.2 mM CaCl2, 0.5 mg/ml BSA). After the final wash is aspirated, 200 μl of solubilization buffer (10 mM Tris Cl, pH 7.4, 1 mM EDTA, 1% (v/v) Triton X-100) is added to each well and incubated at room temperature for 15–30 min. The solubilized cells are then transferred to fresh tubes and counted in a Packard Model 5005 COBRA Gamma Counter (Packard Instruments, Meriden, Conn.).

Figure 6:
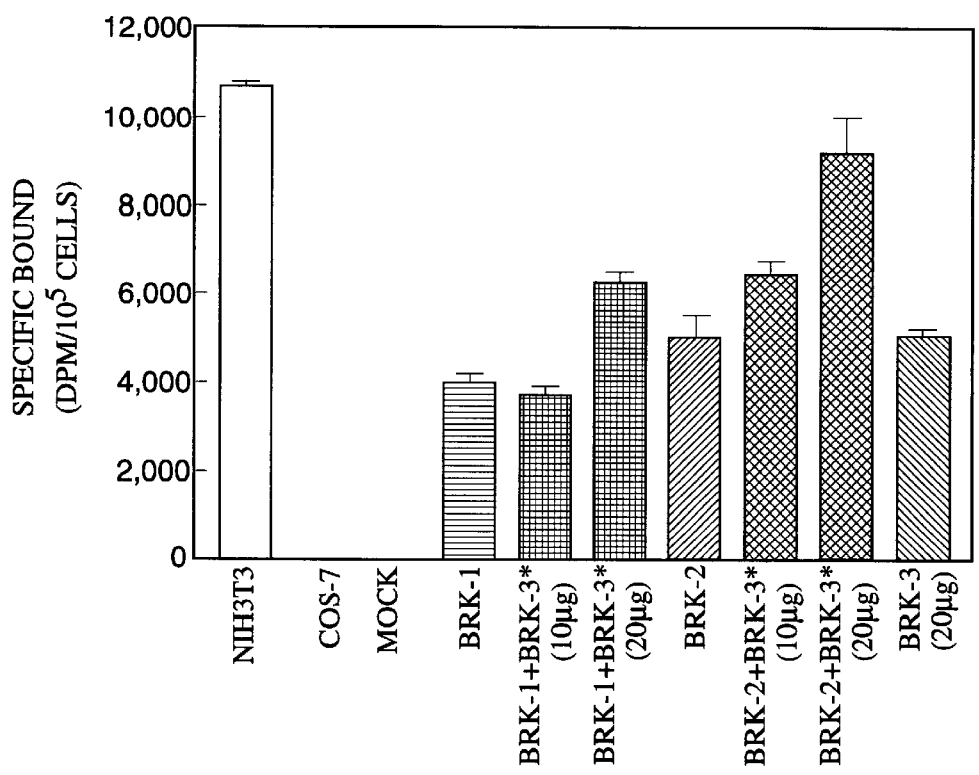
FIG. 6 shows whole cell binding of $[^{125}I]$-BMP-4 to t-BRK-3 expressed in COS-7 cells, in the presence or absence of the type I receptors BRK-1 and BRK2. Bars represent specific binding of $[^{125}I]$-BMP-4, normalized to cell number. Left to right, NIH3T3 embryonic fibroblasts; COS-7 cells; COS-7 cells transfected with the vector pJT-4 alone (designated "mock"); COS-7 cells transfected with BRK-1 alone, BRK-1 plus 10 or 20 μg of t-BRK-3, BRK-2 alone, BRK-2 plus 10 or 20 μg of t-BRK-3, and t-BRK-3 alone (20 μg).

Results are shown in FIG. 6, which shows specific binding of [$^{125}$I]-BMP-4 to NIH3T3 cells (ATCC CRL 1658), which display significant endogenous binding of BMP-4, and COS 7 cells transfected with the cDNA for t-BRK-3 in the presence and absence of BRK-1 and BRK-2. t-BRK-3 is capable of binding [$^{125}$I]-BMP-4 when expressed alone (bar on far right), at a level similar to that seen for BRK-1 and BRK-2 expressed alone. Binding of [$^{125}$I]-BMP-4 is increased by co-expression of t-BRK-3 with BRK-1, and to a greater extent by co-expression of t-BRK-3 with BRK-2.

b. Covalent Crosslinking

Bifunctional crosslinking reagent disuccinimidyl glutarate (DSG) (Pierce, Rockford, Ill.) is used to covalently crosslink bound radiolabeled ligand to its receptor by reaction with free amino groups on lysine residues in the two proteins. Following the crosslinking, cellular proteins are separated by gel electrophoresis, and radioactive bands visualized. The labeled bands represent the receptor selectively "tagged" with the radiolabeled ligand. In this procedure, cells are transfected with the cDNA for BRK-3, and/or BRK-1 or BRK-2, as described in example 5, then seeded into 12 well plates. At 48–68 hr after transfection, the cells are washed, equilibrated, and incubated with [$^{125}$I]-BMP-4 and competing unlabeled ligands as described in this example for whole cell binding studies. After completion of the 4 hr incubation with ligand, the cells are washed two to three times at 4° C. with 2 ml of binding buffer having the same composition as described above, except that no BSA is added. To each well is then added 1 ml of fresh BSA-free binding buffer, followed by freshly prepared DSG to a final concentration of 135 μM. After swirling gently to mix the DSG, the plates are incubated for exactly 15 minutes at 4° C. with gentle shaking. At this point the media is aspirated and the cells washed with 3 ml detachment buffer (10 mM Tris base, 0.25 M sucrose, 1 mM EDTA, 0.3 mM PMSF) or PBS. Solubilization buffer (50 μl) is then added to each well and the cells are allowed to solubilise for 30–45 minutes at 4° C. with shaking. An aliquot of the sample (20 μl) is transferred to a fresh tube and 5 μl of 5× sample loading buffer (0.25 M TrisCl, pH 6.8, 10% SDS, 0.5 M DTT, 0.5% bromophenol blue, 50% glycerol; purchased from Five Prime Three Prime, Boulder, Colo.) is added. The samples are boiled for 5 min and centrifuged (13,0000×g, 5 min). The supernatants are loaded onto 7.5% SDS-polyacrylamide gels (Integrated Separation Systems, Natick, Mass.) and subjected to electrophoresis. The gels are stained in 0.12% Coomassie Blue R250, 5% methanol, 7.5% acetic acid; destained in 5% methanol, 7.5% acetic acid; then dried. Radioactivity on the dried gel is visualized and quantitated on a PHOSPHORIMAGER (Molecular Devices, Sunnyvale, Calif., a device for quantitation of radioactivity using stable phosphor screens), or subjected to autoradiography using Kodak X-OMAT AR autoradiography film (Kodak, Rochester, N.Y.).

Figure 7:
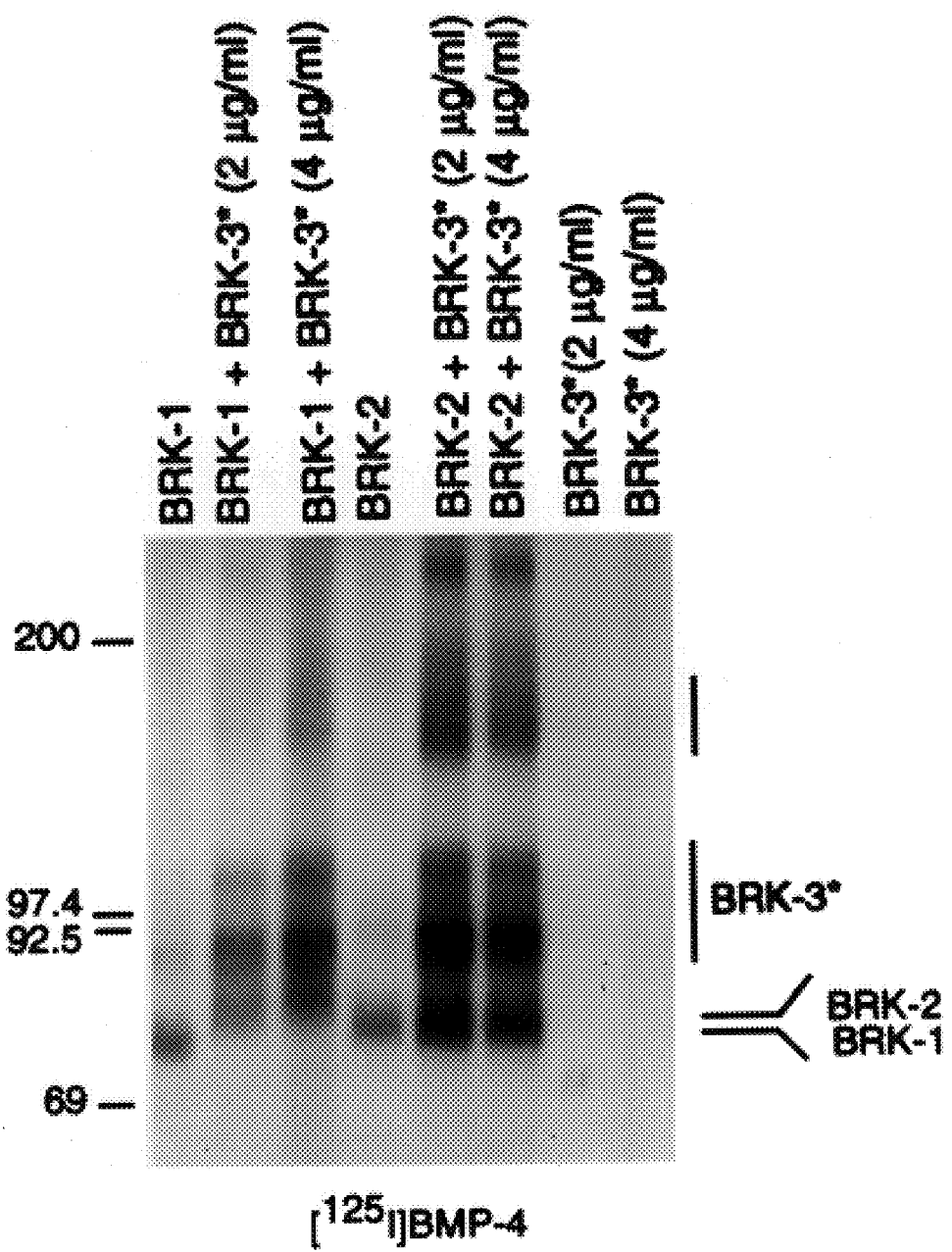
FIG. 7 shows crosslinking of $[^{125}I]$-BMP-4 to COS-1 cells transfected with t-BRK-3, in the presence or absence of the type I receptors BRK-1 and BRK-2. Molecular weight standards are shown on the left. Labels on the right indicate the bands which migrate at the predicted molecular weights of t-BRK-3, BRK-1, and BRK-2 crosslinked to $[^{125}I]$-BMP-4. Left to right, the lanes represent COS-1 cells transfected with BRK-1 alone; BRK-1 plus 2 μg/ml t-BRK-3; BRK-1 plus 4 μg/ml t-BRK-3; BRK-2 alone; BRK-2 plus 2 μg/ml t-BRK-3; BRK-2 plus 4 μg/ml t-BRK-3; t-BRK-3 alone at 2 μg/ml; and t-BRK alone at 4 μg/ml. Volume of DNA mixture is 4 ml. In this figure, "BRK-3*" is t-BRK-3.

Results are shown in FIG. 7. When t-BRK-3 is expressed alone in COS-1 cells, no crosslinked band is seen. Expression of BRK-1 alone results in a crosslinked band at a molecular weight of 78 kD, corresponding to the predicted molecular weight of BRK-1 plus the monomer molecular weight of BMP-4. Co-expression of t-BRK-3 and BRK-1 results in the appearance of a band of similar size to that for BRK-1, as well as a new crosslinked band at 94 kD, corresponding to the predicted molecular weight of t-BRK-3 plus the monomer molecular weight of crosslinked BMP-4. Similarly, expression of BRK-2 alone yields a single crosslinked band at 75 kD, corresponding to the predicted molecular weight of BRK-2 plus the crosslinked BMP-4 monomer. Co-expression of t-BRK- 3 with BRK-2 yields a crosslinked band corresponding to that seen for BRK-2 alone, as well as a new crosslinked band at 94 kD, again corresponding to the predicted molecular weight of t-BRK-3 plus the monomer molecular weight of crosslinked BMP-4. Thus, crosslinking of [$^{125}$I]-BMP-4 to t-BRK-3 is observed only in the presence of a co-expressed type I BMP receptor.

EXAMPLE 8

Demonstration of Complex Formation with Type I BMP Receptors

Receptors of the TGF-β receptor family have been shown to form complexes involving a type I and a type II receptor (L. Attisano, J. L. Wrana, F. Lopez-Casillas, and J. Massagué, *J. Biochim Biophys. Acta*, 1222: 71–80 (1994)). In order to demonstrate that the type II BMP receptor t-BRK-3 can form a complex with the type I BMP receptors BRK-1 and BRK-2, COS-1 cells are co-transfected with the cDNA for t-BRK-3 and BRK-1, or t-BRK-3 and BRK-2, as described in Example 5. The receptors are crosslinked to [$^{125}$I]-BMP-4, then subjected to immunoprecipitation with antibodies specific for the type I receptors BRK-1 and BRK-2. If antibodies specific for a type I receptor precipitate not only the type I receptor crosslinked to [$^{125}$I]-BMP-4, but also BRK-3 crosslinked to [$^{125}$I]-BMP-4, this indicates that the two receptors must be forming a complex, as expected for type I and type II receptors having the same ligand-binding specificity.

Antibodies specific for the type I receptors BRK-1 and BRK-2 are generated using as antigen the peptide LNTRVGTKRYMAPEVLDESLNKNC (SEQ ID NO:27) (B. B. Koenig, et al., *Molec. Cell. Biol.,* 14: 5961–5974 (1994)). This peptide is based on the amino acid sequence of BRK-1 in the intracellular kinase domain, amino acids 398–420 in SEQ ID NO: 12, with the addition of a cysteine at the C terminus to permit conjugation of the peptide. Comparison of the amino acid sequence of the kinase domain of BRK-1 with the kinase domain of the Raf protein suggests that this region of BRK-1 corresponds to a region of the Raf kinase which was used to make highly specific antibodies (W. Kolch, E. Weissinger, H. Mischak, J. Troppmair, S. D. Showalter, P. Lloyd, G. Heidecker, and U. R. Rapp, *Oncogene,* 5: 713–720 (1990)). This peptide is conjugated by standard methods to keyhole limpet hemocynanin, and used to immunize three New Zealand White rabbits (Hazleton Washington, Vienna, Va.). The resulting antisera are evaluated for their ability to recognize the original peptide coated on plastic, using an antibody capture ELISA. The antisera are designated 1378, 1379, and 1380. These antibodies are shown to immunoprecipitate BRK-1 from COS-7 cells transfected with the cDNA for BRK-1, using the procedure detailed in this example (B. B. Koenig, et al., *Mol. Cell. Biol.,* 14: 5961–5974 (1994)). Because the sequence of BRK-2 is nearly identical to that of BRK-1 in this region, these antibodies are subsequently tested for their ability to immunoprecipitate BRK-2 as well, and are found to be effective for this purpose. Antibody 1379 gives superior results for immunoprecipitation of BRK-1, and antibody 1380 is preferred for immunoprecipitation of BRK-2.

In the immunoprecipitation procedure, COS-7 or COS-1 cells are transfected with the cDNA for t-BRK-3 and/or BRK-1, BRK-2, or DAF-4 as described in Example 5, and plated into 100 mm dishes. They are then crosslinked to [$^{125}$I]-BMP-4 as described in example 7, except that the incubation with [$^{125}$I]-BMP-4 and unlabeled ligand is carried out in a total of 4 ml, instead of 500 μl, and all other volumes are increased accordingly. Following the crosslinking, cells are washed three times with ice-cold PBS, then lysed with 1 ml of RIP buffer (20 mM TrisCl, pH 8.0, 100 mM NaCl, 1 mM Na$_2$EDTA, 0.5% Nonidet P-40, 0.5% sodium deoxycholate, 10 mM sodium iodide, and 1% bovine serum albumin) for 10 min. The lysate is centrifuged in a microcentrifuge at 13,000 rpm for 10 min at 4° C. The supernatant is transferred to a fresh tube and made 0.1% in SDS. To remove any existing antibody present in the lysate, 50 μl of PANSORBIN (Calbiochem, La Jolla, Calif.; a 10% solution of *Staphylococcus aureus*) is added. After a 30 minute incubation at 4° C., the lysate is centrifuged as before, and the supernatant again transferred to a fresh tube.

The primary antibody—1379 when cells are transfected with t-BRK-3 and BRK-1; 1380 when cells are transfected with t-BRK-3 and BRK-2—is then added to the tube at a final dilution of 1:100, and incubated for 2 hr on ice or overnight at 40° C. To precipitate the complex of antigen:primary antibody, 25–50 μl of PANSORBIN is then added and incubated 30 min on ice. The complex is pelleted at 13,000 rpm for 10 min in a microcentrifuge and the supernatant discarded. The pellet is washed twice in RIP buffer containing 0.1% SDS, and once in TNEN buffer (20 mM Tris, pH 8.0, 100 mM NaCl, 1 mM EDTA, 0.5% NP-40). The pellet is resuspended in 25 μl of 1× sample loading buffer. (Alternatively, the pellet may be washed twice with TNEN buffer, with similar results.) The sample is boiled for 5 min, centrifuged for 5 min, and subjected to gel electrophoresis after loading of the samples onto a 7.5% SDS-polyacrylamide gel.

Figure 8:
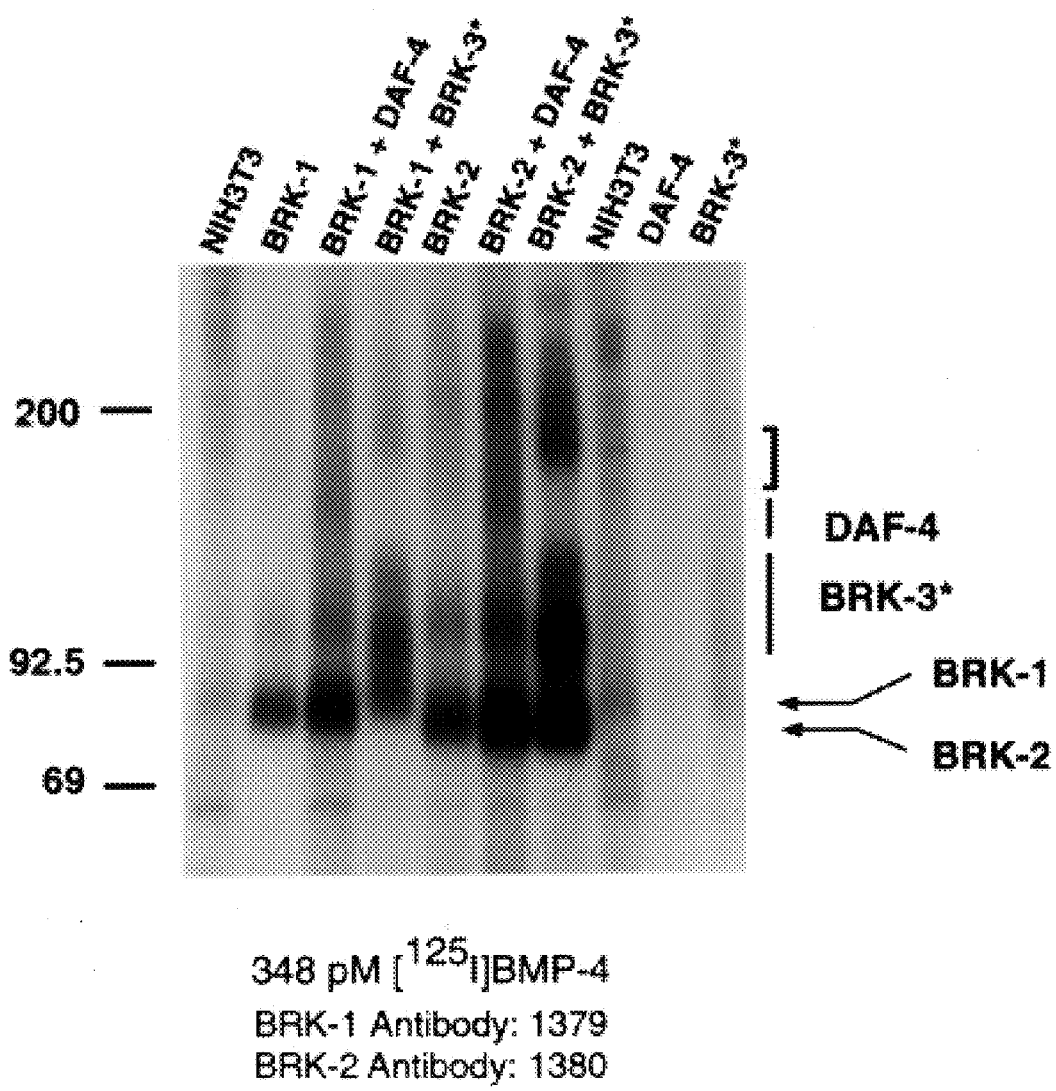
FIG. 8 shows an immunoprecipitation of t-BRK-3 and the *C. elegans* type II receptor DAF-4 expressed in COS-1 cells and crosslinked to $[^{125}I]$-BMP-4 in the presence or absence of the type I receptors BRK-1 or BRK-2. Molecular weight standards are shown on the left; areas shown at the right indicate labeled protein bands migrating at the predicted molecular weight of DAF-4, t-BRK-3, BRK-1, or BRK-2 crosslinked to $[^{125}I]$-BMP-4. Antiserum 1379 was used for COS-1 cells transfected with BRK-1 in the presence or absence of type II receptors, and antiserum 1380 for COS-1 cells transfected with BRK-2 in the presence or absence of type II receptors. For all others, antiserum is listed in parentheses. Left to right, NIH3T3 embryonic fibroblasts (1379), followed by COS-1 cells transfected with BRK-1 alone; BRK-1 plus DAF-4; BRK-1 plus t-BRK-3; BRK-2 alone; BPK-2 plus DAF-4; BRK-2 plus t-BRK-3. This is followed by NIH3T3 cells (1380), followed by COS-1 cells transfected with DAF-4 alone (1379), and t-BRK-3 alone (1380). In this figure, "BRK-3*" is t-BRK-3.

Results of this experiment are shown in FIG. 8, which shows the results of immunoprecipitations on COS-1 cells transfected with t-BRK-3 in the presence or absence of BRK-1 or BRK-2. Cells transfected with t-BRK-3 alone, crosslinked to [$^{125}$I]-BMP-4, and immunoprecipitated with antibody 1380 show no radiolabel in the immunoprecipitate, as expected since t-BRK-3 does not crossreact with this antibody. Cells transfected with BRK-1, crosslinked, and immunoprecipitated with antibody 1379 show a single labeled band at 78 kD, consistent with the predicted molecular weight of BRK-1 plus the cross-linked monomer of BMP-4. Immunoprecipitation of cells co-transfected with BRK-1 and t-BRK-3 yields the same band seen with BRK-1 alone, plus an additional labeled band at 94 kD, consistent with the predicted molecular weight of t-BRK-3 plus the crosslinked BMP-4 monomer. (A less intense band at 120 kD is also observed.) The fact that antibodies to BRK-1 precipitate not only BRK-1, but t-BRK-3 as well in these cells indicates complex formation between BRK-1 and t-BRK-3. Similarly, cells transfected with BRK-2, crosslinked to [$^{125}$I]-BMP-4, and subjected to immunoprecipitation with antibody 1380 show a labeled band at 75 kD, consistent with the predicted molecular weight of BRK-2 plus the crosslinked monomer of BMP-4. Immunoprecipitation of cells co-transfected with BRK-2 and t-BRK-3 yields the same band seen with BRK-2 alone, plus a strongly labeled band at 94 kD, consistent with the predicted molecular weight of t-BRK-3 plus the crosslinked monomer of BMP-4. As expected, this band co-migrates with the larger labeled band in cells co-transfected with BRK-1 and t-BRK-3. (A less intense band at 120 kD is also observed.) Again, the fact that an antibody to BRK-2 precipitates not only BRK-2 but t-BRK-3 as well in these cells strongly indicates that BRK-2 and t-BRK-3 form a complex. Thus, t-BRK-3 forms a complex with two different type I BMP receptors, as expected for a type II BMP receptor.

A second immunoprecipitation experiment is carried out to test the ligand specificity of the t-BRK-3 receptor complex for BMP-2, BMP-4, and TGF-β$_1$. A derivative of BMP-2 designated "digit-removed" BMP-2 (DR-BMP-2) is also tested; DR-BMP-2 is prepared by mild trypsin digestion of BMP-2 to remove the amino terminus, and shows significantly reduced nonspecific binding to whole cells (B. B. Koenig, et al., *Molec. Cell. Biol.,* 14: 5961–5974 (1994)).

Figure 9:
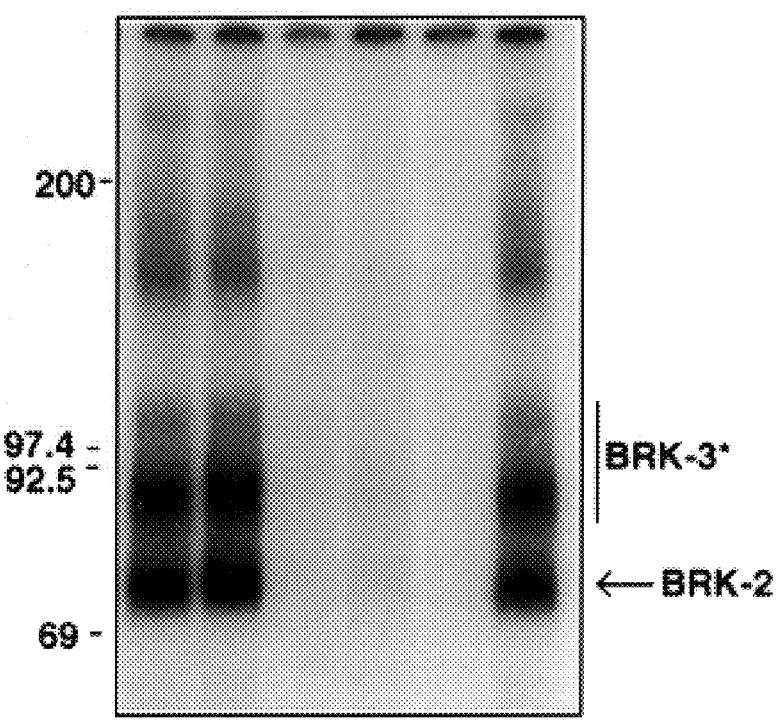
FIG. 9 shows an immunoprecipitation of COS-1 cells transfected with BRK-2 and t-BRK-3 and crosslinked to $[^{125}I]$-BMP-4 at a concentration of 210 pM, in the presence or absence of excess unlabeled competitors as indicated. Antiserum 1380 is used. Duplicate lanes at left show no unlabeled competitor added, followed by addition of (left to right) 10 nM BMP-4; 10 nM BMP-2; 10 nM DR-BRMP-2; and 50 nM TGF-$β_1$. In this figure, "BRK-3*" is t-BRK-3.

COS-1 cells are co-transfected with the cDNA for BRK-2 and t-BRK-3 as described in Example 5, crosslinked to [$^{125}$I]-BMP-4, and subjected to immunoprecipitation with antibody 1380 as described in this example, except that an excess of unlabeled ligand (10 nM BMP-4, 10 nM BMP-2, 10 nM DR-BMP-2, or 50 nM TGF-β$_1$) is added to the incubation at the same time as the [$^{125}$I]-BMP-4. The results are shown in FIG. 9. When no competing unlabeled ligands are present, two labeled bands are observed, at 75 kD and 94 kD, consistent with crosslinked BRK-2 and BRK-3 respectively, as seen in FIG. 8. In the presence of excess unlabeled BMP-4, BMP-2, or DR-BMP-2, however, these bands are completely abolished, demonstrating that these ligands compete effectively with [$^{125}$I]-BMP-4 to bind to the complex, and that all these ligands show specific binding to the BRK-2 and BRK-3 receptor complex. However, the presence of 50 nM TGF-$\beta_1$ has no effect on the labeled bands, indicating that TGF-$\beta_1$ does not bind to the same site as [$^{125}$I]-BMP-4. This shows that the BRK-2/t-BRK-3 complex binds specifically to BMP-2 and BMP-4 and does not bind TGF-$\beta$.

EXAMPLE 9

Isolation of Mouse BRK-3

In order to isolate the full-length mouse homologue of BRK-3, a cDNA library is constructed from NIH3T3 mouse embryonic fibroblasts (ATCC CRL 1658). Total RNA (1.26 mg) is isolated from the cells using a Total RNA Separator Kit (Clontech, Palo Alto, Calif.). Messenger RNA (81 μg) is isolated from this total RNA (1 mg) using the mRNA Separator Kit (Clontech, Palo Alto, Calif.). An aliquot of the mRNA (4 μg) is used to make cDNA library using the SUPER SCRIPT Plasmid System for cDNA Synthesis and Plasmid Cloning (Life Technologies, Gaithersburg, Md.) according to the manufacturer's instructions. The resulting library contained approximately 4.9×10$^5$ primary colonies, and is divided into 98 pools, each containing 5000 colonies.

The initial screen of the library is accomplished by Southern blotting. Plasmids are purified from each of the 98 pools, using QIAGEN columns (Qiagen, Chatsworth, Calif.). DNA from each pool (approximately 5 μg) is digested with Mlu I to release the cDNA insert, then run on a 1% agarose gel. The gel is denatured for 30 min in 0.6 M NaCl, 0.4 N NaOH, then neutralized 30 min in 1.5 M NaCl, 0.5 M Tris, pH 7.5. The DNA is then transferred overnight to a HYBOND Nylon membrane (Amersham, Arlington Heights, Ill.) using 10×SSC as the transfer buffer (1×SSC= 0.15 M NaCl, 0.015 M sodium citrate, pH 7.0).

Human t-BRK-3 is cut with EcoRV and Afl III to give a 1.5 kb fragment. The fragment is randomly labeled with alpha[$^{32}$P]-dCTP having a specific activity of 3000 Ci/mmol (NEN Research Products, Boston, Mass.), using a PRIME-IT II Random Primer Labeling Kit (Stratagene, La Jolla, Calif.; a kit for random primer labeling of DNA, including Klenow DNA polymerase, primers, and buffers). The labeled probe is allowed to hybridize to the Southern blot for 18 hr at 42° C. in hybridization buffer (Sigma, St. Louis, Mo.) consisting of 50% deionized formamide, 5×SSPE (1× SSPE=0.14 M NaCl, 8 mM sodium phosphate, 0.08 mM EDTA, pH 7.7), 1× Denhardt's solutions, and 100 μg/ml of denatured salmon testis DNA. The blot is then washed in 0.25×SSPE, 0.5% sodium dodecyl sulfate (SDS), two times at 42° C. for 15 min each, then two times at 65° C. for 20 min each. The blot is then exposed to Kodak X-OMAT AR autoradiography film for 18 hr at −80° C. Development of the film shows five positive pools, as judged by the presence of a labeled band of approximately 2.5 kb.

For secondary screening, plates are streaked with the *E. coli* stocks from the five positive pools (5000 colonies/ plate). A HYBOND nylon membrane is placed on top of the plate so that the bacterial colonies are transferred to the filter. The colonies are then allowed to recover at 37° C. for 2–3 hr. The filter is soaked in 10% SDS for 3 min, then transferred to 1.5 M NaCl, 0.5 M NaOH for 5 min, neutralized in 1.5 M NaCl, 1.5 M Tris, pH 7.5 for 5 min, and washed in 2×SSC. To remove proteins, the blots are then shaken with 50 μg/ml of proteinase K (Boehringer Mannheim, Indianapolis, Ind.) in 0.1 M Tris, pH 7.6, 10 mM EDTA, 0.15 M NaCl, 0.02% SDS at 55° C. for 1 hr. The human BRK-3 fragment (Eco RV-Afl III) is labeled and the blots hybridized, washed, and subjected to autoradiography exactly as described above for the primary screening.

Colonies which corresponded to labeled spots on the autoradiograph are streaked on plates for tertiary screening, which is performed exactly as described above for secondary screening. Four positive clones are isolated. One clone, pSPORT1/N89-5, is found to have the largest insert size, 2.9 kb.

The inserts from the four positive clones are sequenced using the TAQ DYE DEOXY Terminator Cycle Sequencing Kit and an Applied Biosystems Model 373A Automated DNA Sequencer. Comparison of the four sequences shows that three of the four are identical at the 3' end, and all four align with the coding region of human BRK-3 at the 5' end. The longest clone, pSPORT1/N89-5, aligns with the human BRK-3 sequence approximately 600 pairs from the beginning of the coding region.

To generate more sequence information, the insert from pSPORT1/N89-5 is digested with EcoRi and Sca I, and the resulting 1.4 kb fragment is subcloned into BLUESCRIPT II SK(−) at the Eco RI and Hinc II sites. pSPORT1/N89-5 is also digested with Eco RI and Eco RV and the resulting 2.1 kb insert subcloned into the same vector at the same sites. Finally, the plasmid is digested with Sca I and Not I, and subcloned into the same vector at the Hinc II and Not I sites. Sequencing of these three constructs yields the complete sequence of the insert from pSPORT1/N89-5.

The missing 600 base pairs at the 5' end of the coding region is cloned using the 5' RACE System for Rapid Amplification of cDNA Ends (Life Technologies, Gaithersburg, Md.). An antisense primer is designed corresponding to the known sequence of pSPORT1/N89-5, having the sequence 5' CTG TGT GAA GAT AAG CCA GTC 3' (SEQ ID NO:28) (the reverse complement of nucleotides 968–948 in SEQ ID NO:7). After first strand synthesis of cDNA from 1 μg of NIH3T3 mRNA, a poly C tail is added to the newly synthesized cDNA using terminal deoxynucleotidyl transferase, according to the manufacturer's instructions. The primer above is used to amplify the 5' end of the BRK-3 cDNA, together with the Anchor Primer supplied with the kit, having the sequence 5' (CUA)$_4$ GGC CAC GCG TCG ACT AGT ACG GGI IGG GII GGG IIG 3' (SEQ ID NO:29, 30, and 31) (where I=inosine and U=uracil). PCR was performed using the GENE-AMP PCR Kit with AMPLITAQ DNA Polymerase. An initial melting period at 95° C. for 5 min was followed by 35 cycles of the following program: melting at 95° C. for 1 min, annealing at 55° C. for 1 min, and extension at 72° C. for 2 min. After the last cycle, the reaction was held at 72° C. for 5 min to complete extension. To reduce background from nonspecific primer binding, a second round of PCR is performed using the nested primer 5' CAA GAG CTT ACC CAA TCA CTT G 3', (SEQ ID NO:32) again derived from the known sequence of the insert from pSPORT1/N89-5 (the reverse complement of nucleotides 921–900 in SEQ ID NO: 7), together with same 5' anchor primer used in the first round of PCR.

The amplified products of the second PCR reaction in the size range of 600–1000 bp are digested with Ecl XI and Sal I and subcloned into BLUESCRIPT II SK(−) at the Ecl XI and Sal I sites. The inserts are then sequenced, yielding an additional 600 bp of sequence which align with the coding region of human t-BRK-3. Three separate clones, designated R6-8B2, R6-11-1, and R6-11-2, are sequenced with identical results.

In order to assemble a full length clone of mouse BRK-3, a Sal I site is first placed at the 5' end of clone R6-11-1 as follows. A primer is synthesized which contains a Sal I site followed by nucleotides 1–20 of the sequence of R6-11-1; the sequence of the primer is 5' CAC ACG CGT CGA CCA TGA CTT CCT CGC TGC ATC G 3' (SEQ ID NO:33). This is used together with the M13 reverse primer, 5' AAC AGC TAT GAC CAT G 3' (SEQ ID NO:34), in order to amplify a DNA fragment using plasmid DNA from clone R6-11-1 as the template. PCR was performed using the GENE-AMP PCR Kit with AMPLITAQ DNA Polymerase. An initial melting period at 95° C. for 5 min was followed by 35 cycles of the following program: melting at 95° C. for 1 min, annealing at 55° C. for 1 min, and extension at 72° C. for 2 min. After the last cycle, the reaction was held at 72° C. for 5 min to complete extension. The fragment amplified from R6-11-1, together with the insert from pSPORT1/N89-5 (230 ng), is then subcloned in to BLUESCRIPT II SK(–) as follows. The amplified fragment from R6-11-1 is digested with Sal I and Ecl XI. The insert from pSPORT1/N89-5 is digested with Ecl XI and Pst I. The vector BLUESCRIPT II SK(–) is digested with Sal I and Pst I. The three fragments are combined in a three-way ligation using T4 DNA ligase (3 hr, 25° C.) and used to transform electrocompetent E coli, strain DH5-a, using a BIO-RAD Gene PULSER (BIO-RAD, Hercules, Calif.) according to the manufacturer's instructions. A positive colony is selected and is designated pBLUESCRIPT-mBRK3. Sequencing of the 5' portion of the insert that was amplified by PCR shows a sequence identical to that of clone R6-11-1, indicating that no mutations are introduced during the amplification.

For mammalian expression, m-BRK-3 is subcloned into the mammalian expression vector pJT6. This vector is a derivative of pJT3, described in example 4 above, in which the Not I site at the 5' end of the multiple cloning site has been deleted, and a spacer inserted between the Pst I and BamHI restriction sites in the multiple cloning site. To accomplish the subcloning, m-BRK-3 is excised from pBLUESCRIPT-mBRK3 using Not I and Sal I, then subcloned into pJT6 at the Not I and Sal I sites to generate pJT6-mBRK3.

However, resequencing of the 3' end of pJT6-mBRK3 and the original cDNA in pSPORT1/N89-5 results in an altered reading frame at the 3' end, and shows that the stop codon is actually located 3' to the Pst I site. Thus, pJT6-mBRK3 does not contain a stop codon. Accordingly, two new constructs are prepared as follows.

Figure 10:
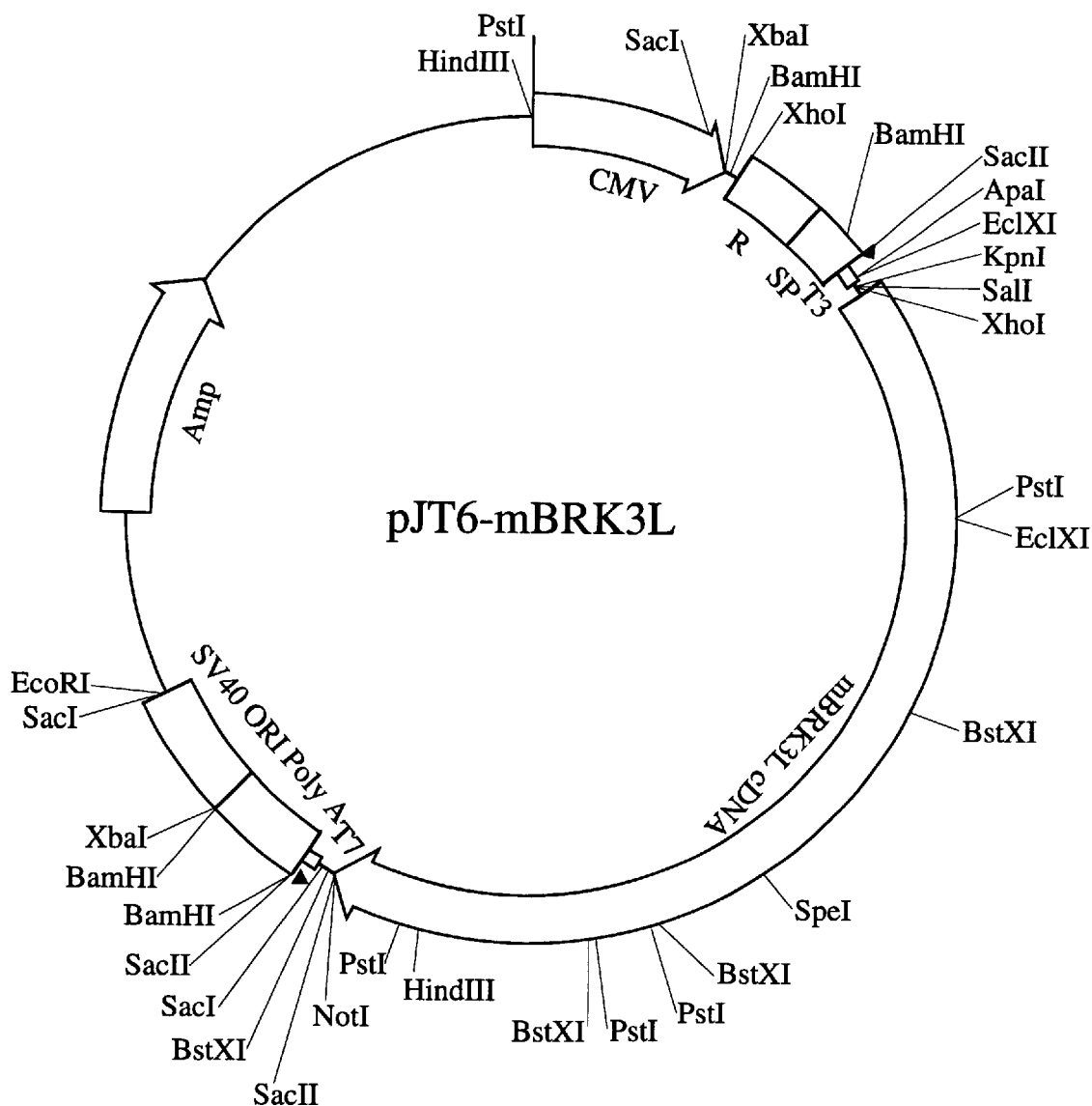
FIG. 10 shows the construct pJT6-mBRK-3L, used for transient mammalian expression of mouse BRK-3. Abbreviations used are the same as those for FIG. 2.

First, pJT6-mBRK3 is digested with SpeI (site at position 2306 in SEQ ID NO: 7) and Not I (in the multiple cloning site of pJT6), removing the 3' end of the insert. The longest clone isolated during the screening of the NIH-3T3 library, pSPORT1/N89-5, is also digested with Spe I and Not I. The 1.2 kb fragment liberated from pSPORT1/N89-5 is subcloned into the Spe I/Not I digested pJT6-mBRK3, regenerating both sites. This construct is designated pJT6-mBRK-3L, and contains the entire 3'end of the pSPORT1/N89-5 clone. A map of the construct is shown in FIG. 10.

Figure 11:
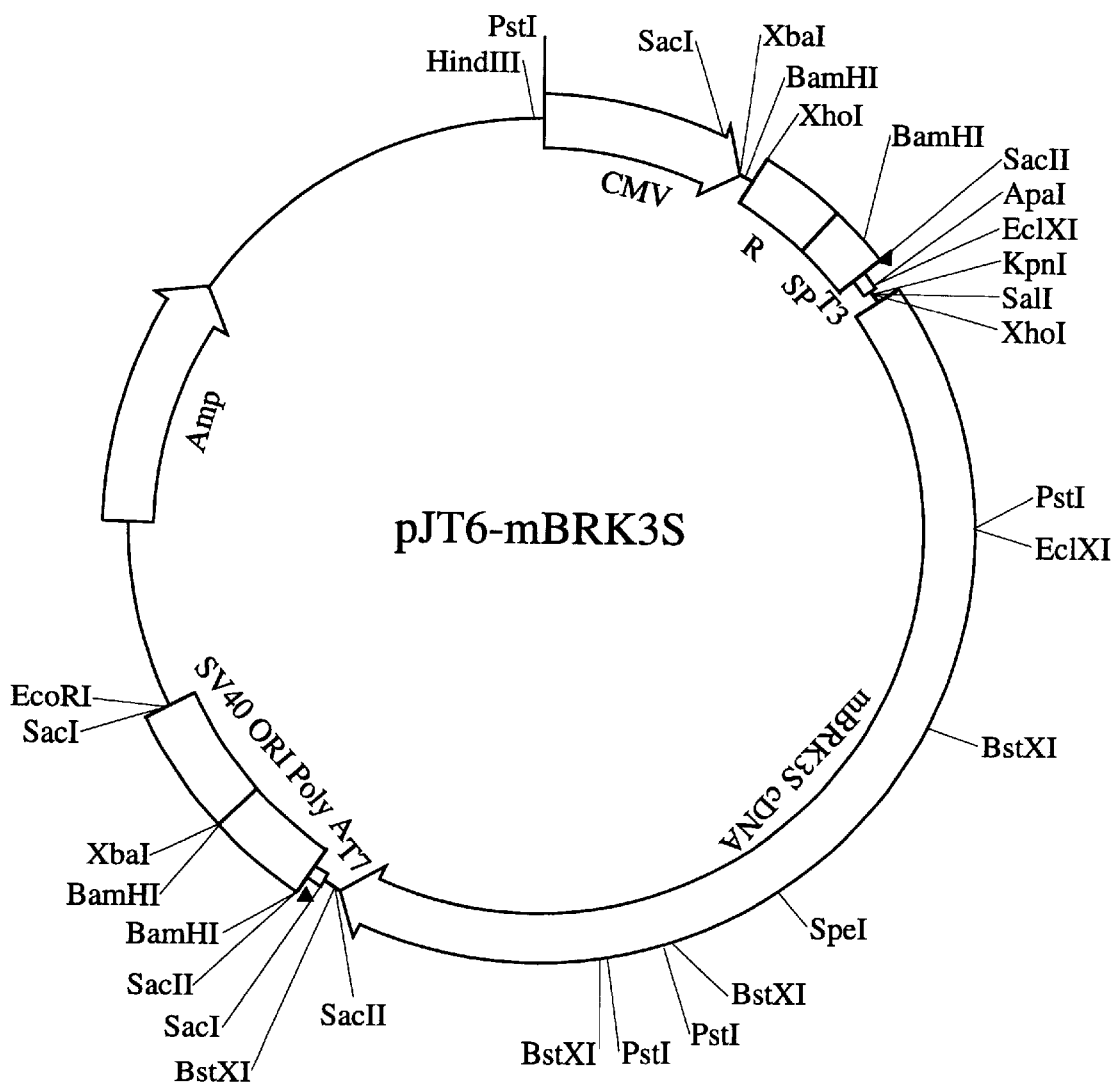
FIG. 11 shows the construct pJT6-mBRK-3 S, used for transient mammalian expression of mouse BRK-3. In this construct, most of the untranslated 3' region has been removed. Abbreviations used are the same as those for FIG. 2.

The 3' end of the clone contains 403 nucleotides in the untranslated region 3' to the stop codon. This region is very A-T rich, which might possibly lead to decreased expression levels. To remove this region, a second construct is prepared. The pSPORT1/N89-5 plasmid is digested with Hind III (site at nucleotide 3168 in SEQ ID NO:7, 21 bases 3' to the stop codon). The linearized plasmid is treated with Klenow fragment of DNA polymerase (Boehringer Mannheim, Indianapolis, Ind.) to fill in overhangs, then cut with Spe I to liberate an 863 bp fragment at the 3' end of the insert. At the same time, pJT6-mBRK3 is digested with Not I. The linearized plasmid is treated with Klenow fragment, then cut with Spe I, releasing the 3' end of the insert. The Not I/Spe I digested pJT6-mBRK3 is then ligated to the fragment liberated from pSPORT1/N89-5 by Hind III/Spe I. This regenerates the Spe I site; the Hind III and Not I sites are destroyed. The resulting construct is designated pJT6-mBRK3S, and is shown in FIG. 11.

The construct pJT6-mBRK-3S is also constructed directly from the partial cDNA clone of m-BRK-3, pSPORT1/N89-5, and the construct containing the 5' end of the cDNA, clone R6-11-1. This is accomplished by digestion of clone R6-1 1-1 with Sal I and Ecl XI, digestion of pSPORT1/N89-5 with Ecl XI and Hind III, and digestion of BLUESCRIPT II SK (–) with Sal I and Hind III. These fragments are then subjected to a three-way ligation to generate the full length m-BRK-3 cDNA in the BLUESCRIPT II vector. The full length cDNA is then excised from this construct using Sal I and Not I, then subcloned into the Sal I and Not I sites of the pJT6 vector. The resulting plasmid has exactly the same cDNA for BRK-3 as does pJT6-mBRK3S described in the above example. However, it carries additional vector sequence at the 3' end of the cDNA, comprising the region between the Hind III and Not I sites in the multiple cloning site of BLUESCRIPT II SK(–).

EXAMPLE 10

Sequence Analysis of Mouse BRK-3

The DNA sequence of the full length mouse BRK-3 insert from pJT6-mBRK3L is shown in SEQ ID NO: 7, and the deduced protein sequence is shown in SEQ ID NO: 8. The deduced amino acid sequence of mouse BRK-3 is searched against all translated protein sequences in GenBank release 84.0, dated Aug. 15, 1994, using a standard Needleman-Wunsch algorithm (S. B. Needleman and C. D. Wunsch, J. Mol. Biol, 48: 443–453 (1970)). It is found to be a unique sequence. It encodes a protein of 1038 amino acids. Comparing mouse BRK-3 with the truncated human receptor over the region encoded by t-BRK-3 (amino acids 1–582 in SEQ ID NO:4; amino acids 1–582 in SEQ ID NO: 8), the two receptors are 98% identical in sequence. Like t-BRK-3, m-BRK-3 contains a predicted transmembrane region encompassing amino acids 151–172. As with t-BRK-3, the intracellular domain contains all of the consensus sequences that characterize a protein kinase domain with predicted specificity for serine/threonine residues (S. K. Hanks, A. M. Quinn, and T. Hunter, Science, 241: 42–52 (1988)). The kinase domain is followed by an extremely long carboxy terminus (534 amino acids). Indeed, due to the presence of this carboxy terminus, the intracellular domain in BRK-3 (866 amino acids) is much larger than that of any other receptor in the TGF-β receptor family. It is nearly twice as long as the intracellular domain of DAF-4 (490 amino acids), which has the longest intracellular domain known in the TGF-β family until the present invention.

EXAMPLE 11

Demonstration of [$^{125}$I]-BMP-4 Binding to m-BRK-3

In order to demonstrate that [$^{125}$I]-BMP-4 binds specifically to m-BRK-3, COS-1 cells are transfected as described in Example 5 using the constructs pJT6-mBRK-3S and pJT6-mBRK-3L. In addition, the cells are also co-transfected with cDNA for the type I receptor BRK-2, using the construct pJT3-BRK-2, to determine whether the presence of a type I BMP receptor affects binding of [$^{125}$I]-BMP-4. Whole cell binding with [$^{125}$I]-BMP-4 is carried out as described in Example 7.

Figure 12:
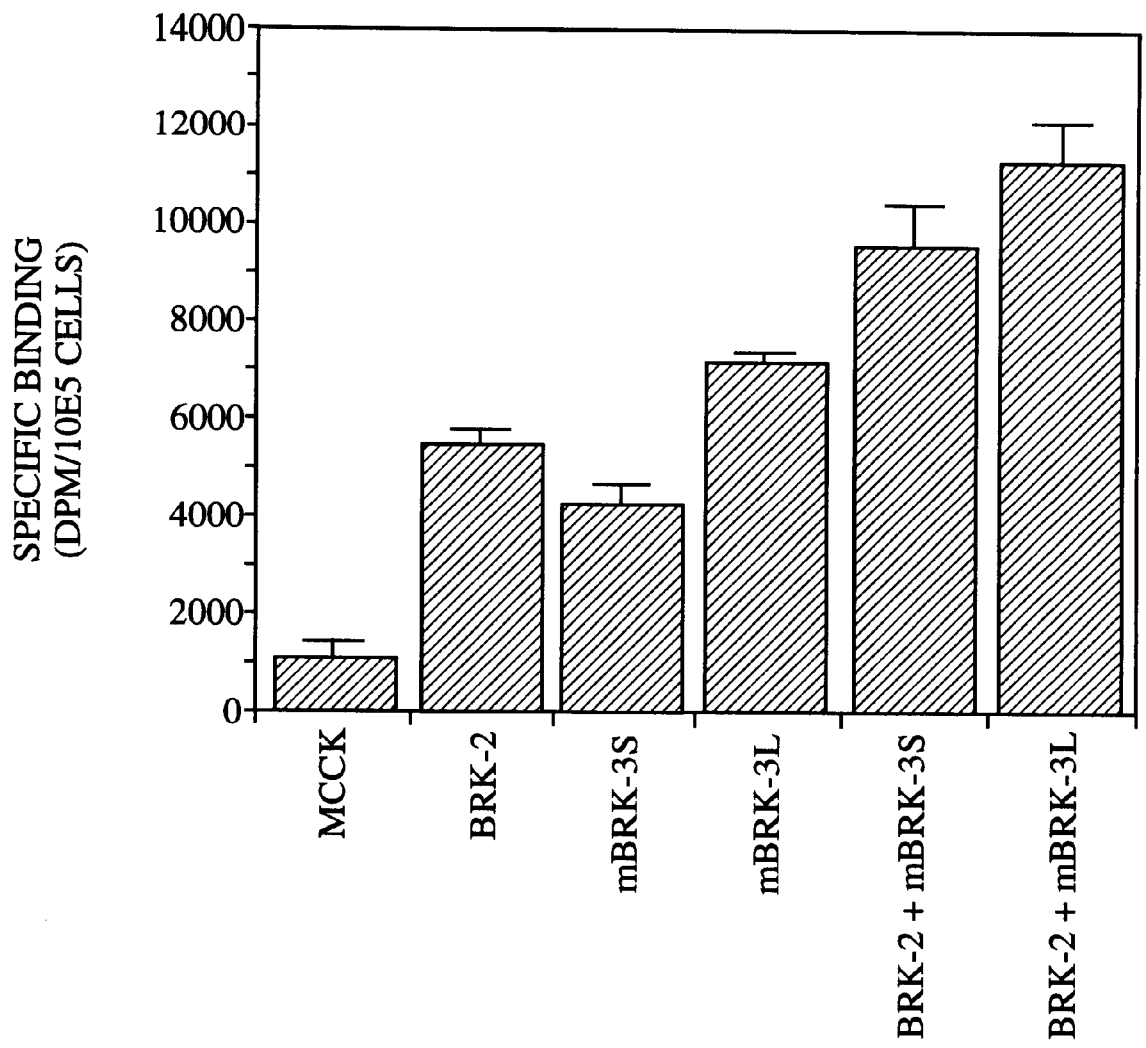
FIG. 12 shows whole cell binding of $[^{125}I]$-BMP-4 to mouse BRK-3 expressed in COS-1 cells, in the presence or absence of the type I receptor BRK-2. Bars represent specific binding of $[^{125}I]$-BMP-4, normalized to cell number. Constructs used for mouse BRK-3 are pJT6-mBRK-3L and pJT6-mBRK-3S; for BRK-2, the construct is pJT3-BRK-2. Both constructs contain the complete coding region of mouse BRK-3. In pJT6-mBRK-3S, an A-T rich region in the 3' untranslated region has been deleted. Left to right, COS-1 cells transfected with the vector pJT-6 alone (designated "mock"); pJT3-BRK-2 alone; the construct pJT6-mBRK-3S alone; pJT6-mBRK-3L alone; pJT3-BRK-2 plus pJT6-BRK-3S; and pJT3-BRK-2 plus pJT6-BRK-3L.

The results are shown in FIG. 12, which shows specific binding of [$^{125}$I]-BMP-4 normalized to cell number. When cells are transfected with mouse BRK-3 alone, using either of the two constructs tested, specific binding of [125I]-BMP-4 is increased to 4–7 times the level seen with mock transfected cells. Transfection of BRK-2 alone shows increased binding at a similar level to that seen with mouse BRK-3 alone. When cells are co-transfected with BRK-2 as well as mouse BRK-3, the binding is further increased to 9–11 times that of mock-transfected cells, consistent with the results obtained with BRK-2 in combination with t-BRK-3 (FIG. 6 in Example 7 above).

As an additional demonstration that m-BRK-3 binds to[$^{125}$I]-BMP-4, a crosslinking experiment is carried out. COS-1 cells are transfected with the cDNA for m-BRK-3, using the construct pJT6-mBRK-3S, and/or with cDNAs for BRK-1 (using pJT4-J159F) or BRK-2 (using pJT3-BRK-2) as described in Example 5. The transfected cells are incubated with [$^{125}$I]-BMP-4 and crosslinked as described in Example 7, except that disuccinimidyl suberate (DSS) is used as the crosslinking agent rather than disuccinimidyl glutarate. The results of such an experiment are shown in FIG. 13. Cells transfected with m-BRK-3 alone show no crosslinked band, consistent with the results obtained with t-BRK-3 (FIG. 7). Cells transfected with the cDNA for BRK-1 alone show a single species migrating at an apparent molecular weight of 81 kD, consistent with the predicted molecular weight of BRK-1 plus the crosslinked BMP-4 monomer. Cells transfected with the cDNAs for BRK-1 and m-BRK-3 show three labeled bands, one of which is consistent with the band seen with BRK-1 alone (81 kD). The other bands migrate with an apparent molecular weight of 159 kD and 128 kD. The larger of these is consistent with the predicted molecular weight of m-BRK-3 plus the crosslinked BMP-4 monomer. Note that the intensity of the crosslinked band identified with BRK-1 is considerably increased, compared to that seen with BRK-1 alone.

Similarly, transfection of cells with the cDNA for BRK-2 alone yields a crosslinked band migrating at an apparent molecular weight of 78 kD, consistent with the predicted molecular weight of BRK-2 plus the crosslinked BMP-4 monomer. In cells transfected with the cDNAs for BRK-2 and mBRK3, the 78 kD species identified with BRK-2 is observed, as well as crosslinked bands at 159 kD and 128 kD, comigrating with the higher molecular weight bands seen in cells transfected with the cDNAs for BRK-1 and m-BRK-3. As with BRK-1, the intensity of crosslinking to the band identified with BRK-2 is considerably increased compared to that seen with BRK-2 alone. Finally, no labeled bands are observed in cells transfected with vector alone.

An immunoprecipitation experiment is carried out to demonstrate the ability of m-BRK-3 to form a complex with type I BMP receptors. COS-1 cells are transfected with the cDNA for m-BRK-3, using the construct pJT6-mBRK-3S, and/or with cDNAs for BRK-1 (using pJT4-J159F) or BRK-2 (using pJT3-BRK-2) as described in Example 5. The transfected cells are incubated with [$^{125}$I]-BMP-4, crosslinked, and subjected to immunoprecipitation with antibodies to the appropriate type I receptor or preimmune serum as described in example 8, except that DSS is used as the crosslinking agent rather than disuccinimidyl glutarate. The results of this experiment are shown in FIG. 14. In cells transfected with cDNA for BRK-1 alone, a single band is precipitated by antibodies to BRK-1, migrating at an apparent molecular weight of 81 kD. In cells transfected with cDNAs for BRK-1 and m-BRK-3, antibodies to BRK-1 precipitate the 81 kD band, which is now increased in intensity. In addition, however, a band migrating at an apparent molecular weight of 159 kD is observed, consistent with the predicted molecular weight of m-BRK-3 plus crosslinked BMP-4 monomer. Similarly, in cells transfected with cDNA for BRK-2 alone, antibodies to BRK-2 precipitate a labeled species migrating at an apparent molecular weight of 78 kD. In cells transfected with cDNAs for BRK-2 and m-BRK-3 and precipitated with antibodies to BRK-2, the 78 kD band identified with BRK-2 is again observed, at increased intensity. In addition, a labeled species is seen at 159 kD, consistent with m-BRK-3 and comigrating with the higher molecular weight band seen in cells transfected with cDNAs for BRK-1 and m-BRK-3. In cells transfected with cDNAs for BRK-2 and m-BRK-3, an additional labeled band is observed at 94 kD. As a control, cells are transfected with the cDNAs for BRK-1 and m-BRK-3, or BRK-2 and m-BRK-3, then subjected to immunoprecipitation with pre-immune sera (lanes far left and far right); no labeled bands are observed.

This experiment shows that when m-BRK-3 is co-expressed with the type I BMP receptors BRK-1 or BRK-2, antibodies which precipitate the type I receptor also precipitate m-BRK-3. Thus, m-BRK-3 can form a complex with either of these mammalian type I BMP receptors, as expected for a mammalian type II BMP receptor. This is consistent with results obtained with t-BRK-3 described in Example 8 above.

EXAMPLE 12

Isolation of Full Length Human BRK-3 cDNA

Since clone HSK723, described in Example 2, does not contain an in-frame stop codon, it is desired to obtain additional sequence 3' to the end of this cDNA. Accordingly, the human foreskin fibroblast library prepared in Example 1 is rescreened with the HSK7-2 PCR fragment, using labeling and screening conditions exactly as described in Example 2. This results in isolation of a longer clone, designated pHSK1030, which contains additional human BRK-3 sequence (total of 3355 base pairs) subcloned in BLUESCRIPT SK(-). Sequencing of the insert from pHSK1030 discloses a coding region of 982 amino acids, but the insert still does not contain an in-frame stop codon.

The remainder of the coding region is cloned by PCR as follows. Two forward primers are derived from the plus strand of clone pHSK1030. The sequences of these primers are as follows: primer RPK3-1, 5' CCTGTCACATAATAGGCGTGTGCC-3' (SEQ ID NO:37) (identical to nucleotides 1998–2021 in SEQ ID NO:1); primer RPK3-2, 5' CGCGGATCCATCATACTGACAG-CATCG 3' (SEQ ID NO:36) (which incorporates a BamHI site followed by nucleotides 2078–2095 in SEQ ID NO:1). Two additional primers are derived from the minus strand of λgt10. These primers are: G10F1, 5' GCTGGGTAGTC-CCCACCTTT 3' (SEQ ID NO:37) and G10F2, 5' GAG-CAAGTTCAGCCTGGT 3' (SEQ ID NO:38).

The human fibroblast cDNA library prepared in Example 1 is used as the template for PCR. The library (0.3 μg) is incubated with the RPK3-1 and G10F1 primers (1 μM each), Tth polymerase ( 1.2 units), all four deoxynucleotides (200 μM each), buffer for the Tth polymerase, and water in a total of 50 μl. Conditions for the PCR cycle are as follows: initial melting at 94° C. for 2 min, followed by 20 cycles of melting, 94° C. for 1.5 min; annealing, 52° C. for 2 min; and extension, 72° C. for 3 min. After cycle 20, the sample is held at 72° C. for an additional 8 min to insure complete extension.

To increase specificity and reduce background, a second round of nested PCR is carried out. The incubation mixture is the same as described in this example for the first round, except that (1) an aliquot of the first PCR reaction (0.5 µl) is used as the template; and (2) RPK3-2 and G10F2 primers are used, instead of RPK3-1 and G10F1. Conditions for the PCR run are identical to those described in this example for the first round of PCR.

The second round of PCR results in the amplification of a 1.6 kb fragment, which is isolated from an agarose gel by QIAEX. This fragment is digested with EcoRI and BamHI, and subcloned into BLUESCRIPT SK(-) at the EcoRI and Bam HI sites. The resulting construct, pHSK723-3U, is sequenced and found to encode the remaining coding region of BRK-3 with an in-frame stop codon.

In order to assemble the full length human BRK-3, the inserts from pHSK1030 and pHSK723-3U are joined at a unique Stu I site (located at nucleotide 3219 in SEQ ID NO: 1) in the vector BLUESCRIPT II SK(-). This yields the complete construct pHSK1040, which contains the complete coding sequence of human BRK-3. The pHSK1040 is shown in FIG. 15. The DNA sequence of human BRK-3 is shown in SEQ ID NO: 1, and the deduced amino acid sequence for human BRK-3 is shown in SEQ ID NO: 2.

The amino acid sequence of human BRK-3 (SEQ ID NO:2) is compared to the amino acid sequence for m-BRK-3 (SEQ ID NO:8) and found to be 96.7% identical.

EXAMPLE 13

Use of the BRK-3 in a Ligand Binding Assay for the Identification of BMP Receptor Agonists and Antagonists Identification of ligands that interact with BRK-3 can be achieved through the use of assays that are designed to measure the interaction of ligands with BRK-3. An example of a receptor binding assay that is adapted to handle large numbers of samples is carried out as follows.

COS-1 cells are transfected with the cDNA for m-BRK-3 using the construct pJT6-mBRK-3L as described in example 11 above, except that cells are grown in a 12 well culture dish. At 48–68 hr after transfection, the cells are washed once with 1.0 ml binding buffer (50 mM HEPES, pH 7.4, 128 mM NaCl, 5 mM KCL, 5 mM MgSO$_4$, 1.2 mM CaCl$_2$, 2 mg/ml BSA), then equilibrated in the same buffer at 4° C. for 60 min. with gentle shaking. After equilibration, the buffer is aspirated, and to each well is added 500 µl of 4° C. binding buffer containing [$^{125}$I]BMP-4 tracer (100–400 pM) in the presence or absence of varying concentrations of unlabeled test compounds (i.e., putative ligands), for a period of 4 hours at 4° C. with gentle shaking. For determination of nonspecific binding and complete displacement from the BMP receptor complex, BMP-2 is added at a final concentration of 10 nM. To prevent degradation of ligand, a protease inhibitor cocktail is also added, to give a final concentration of 10 µg/ml leupeptin, 10 µg/ml antipain, 50 µg/ml aprotinin, 100 µg/ml benzamidine, 100 µg/ml soybean trypsin inhibitor, 10 µg/ml bestatin, 10 µg/ml pepstatin, and 300 µM phenylmethylsulfonyl fluoride (PMSF). At the end of the incubation period, the buffer is aspirated, and the cells are rinsed 4 times with 1 ml washing buffer (50 mM HEPES, pH 7.4, 128 mM NaCl, 5 mM KCl, 5 mM MgSO$_4$, 1.2 mM CaCl$_2$, 0.5 mg/ml BSA). After the final wash is aspirated, 200 µl of solubilization buffer (10 mM Tris Cl, pH 7.4, 1 mM EDTA, 1% (v/v) Triton X–100) is added to each well and incubated at room temperature for 15–30 min. The solubilized cells are then transferred to fresh tubes and counted in a Packard Model 5005 COBRA Gamma Counter (Packard Instruments, Meriden, Conn.).

Test compounds which interact with the m-BRK-3 receptor are observed to compete with binding to the receptor with the [$^{125}$I]BMP-4 tracer in the cells expressing m-BRK-3, such that less [$^{125}$I]BMP-4 tracer is bound in the presence of the test compound in comparison to the binding observed when the tracer is incubated in the absence of the novel compound. A decrease in binding of the [$^{125}$I]BMP-4 tracer by ≧30% at the highest concentration of the test compound that is studied demonstrates that the test compound binds to m-BRK-3.

Similar results are obtained when other, related BRK-3 protein receptor kinases of the present invention are used according to the method of this example.

EXAMPLE 14

Use of m-BRK-3 and BRK-2 in a Ligand Binding Assay for the Identification of BMP Receptor Agonists and Antagonists Identification of ligands that interact with BRK-3 complexed to a type I BMP receptor can be achieved through the use of assays that are designed to measure the interaction of the ligands with this BMP receptor complex. A receptor binding assay that uses the m-BRK-3/BRK-2 complex and is adapted to handle large numbers of samples is carried out as follows.

COS-1 cells are transfected with the cDNAs for m-BRK-3, using the construct pJT6-mBRK-3L, and BRK-2, using the construct pJT3-BRK-2, as described in example 11 above, except that the cells are grown in a 12 well culture dish. The DNA mixture used to transfect the cells contains 2 µg/ml of pJT3-BRK-2 and 4 µg/ml of pJT6-mBRK-3L. At 48–68 hours after transfection, the cells are washed once with 1 ml binding buffer (50 mM HEPES, pH 7.4, 128 mM NaCl, 5 mM KCL, 5 mM MgSO$_4$, 1.2 mM CaCl$_2$, 2 mg/ml BSA), then equilibrated in the same buffer at 4° C. for 60 min with gentle shaking. After equilibration, the buffer is aspirated, and to each well is added 500 µl of 4° C. binding buffer containing [$^{125}$I]BMP-4 tracer (100–400 pM) in the presence or absence of varying concentrations of test compounds (i.e., putative ligands), for a period of 4 hours at 4° C. with gentle shaking. For determination of nonspecific binding and complete displacement from the BMP receptor complex, BMP-2 is added at a final concentration of 10 nM. To prevent degradation of ligand, a protease inhibitor cocktail is also added, to give a final concentration of 10 µg/ml leupeptin, 10 µg/ml antipain, 50 µg/ml aprotinin, 100 µg/ml benzamidine, 100 µg/ml soybean trypsin inhibitor, 10 µg/ml bestatin, 10 µg/ml pepstatin, and 300 µM phenylmethylsulfonyl fluoride (PMSF). At the end of the incubation period, the buffer is aspirated, and the cells are rinsed 4 times with 1 ml washing buffer (50 mM HEPES, pH 7.4, 128 mM NaCl, 5 mM KCl, 5 mM MgSO$_{4, 1.2}$ mM CaCl$_2$, 0.5 mg/ml BSA). After the final wash is aspirated, 200 µl of solubilization buffer ( 10 mM Tris Cl, pH 7.4, 1 mM EDTA, 1% (v/v) Triton X–100) is added to each well and incubated at room temperature for 15–30 min. The solubilized cells are then transferred to fresh tubes and counted in a Packard Model 5005 COBRA Gamma Counter (Packard Instruments, Meriden, Conn.).

Test compounds which interact with the m-BRK-3/BRK-2 receptor complex are observed to compete for binding to the receptor complex with the [$^{125}$I]BMP-4 tracer, such that less [$^{125}$I]BMP-4 tracer is bound in the presence of the test compound in comparison to the binding observed when the tracer is incubated in the absence of the novel compound. A decrease in binding of the [$^{125}$I]BMP-4 tracer by $\geq$30% at the highest concentration of the test compound that is studied demonstrates that the test compound binds to the m-BRK-3/BRK-2 receptor complex.

Similar results are obtained when the other BRK-3 protein receptor kinases of the present invention, or homologues thereof, are used in combination with BRK-2 or other BMP type I receptors.

EXAMPLE 15

Use of m-BRK-3 and BRK-2 in a Signaling Assay for the Identification of BMP Receptor Agonists and Antagonists Identification of ligands that signal upon interaction with BRK-3 complexed to a type I receptor can be achieved through the use of assays that are designed to measure the activation of the receptor protein kinase domain after binding of the ligand to the receptor complex. An in vivo phosphorylation assay that measures changes in phosphorylation of proteins that are immunoprecipitated by antibodies to the BRK-2 Type I receptor in cells that express the mBRK-3/BRK-2 complex is carried out as follows.

COS-1 cells are transfected with the cDNAs for m-BRK-3, using the construct pJT6-mBRK-3 S, and BRK-2, using the construct pJT3-BRK-2, as described in Example 11 above, except that cells are grown in a T175 flask (Falcon). The DNA mixture used to transfect the cells contains 2 $\mu$g/ml of pJT3-BRK-2 and 4 $\mu$g/ml of pJT6-mBRK-3S. 24 hours after transfection, the cells are plated into 100 millimeter tissue culture dishes, allowed to attach to the plates for at least 5 hours, and then the media is changed to DMEM (Life Technologies, Inc., Gaithersburg, Md.) containing 1% fetal bovine serum (HyClone, Logan, Utah), and 2 mM L-glutamine, 0.1 mM MEM nonessential amino acids solution; and grown in this low serum media for an additional 12–18 hours. These serum-starved cells are washed three times with ten milliliters per dish of phosphate-free Dulbecco's modified Eagle's medium (DMEM, Life Technologies, Inc., Gaithersburg, Md.) supplemented with 2 mM L-glutamine, 0.1 mM MEM nonessential amino acids solution, and 25 mM HEPES buffer, pH 7.4. Three milliliters per dish of supplemented phosphate-free DMEM and 0.8–1.0 milliCuries per dish of [$^{32}$P] orthophosphoric acid (DuPont New England Nuclear, Wilmington, Del.) are then added to the cells, which are incubated at 37° C. in 95% air/5% C$_2$ for 3 hours. Following incubation, the cells are treated with appropriate concentrations of ligand stimulators such as BMP-4 for 5 minutes at 37° C. Treated cells are washed three times with ten milliliters per dish of 4° C. 50 mM Tris-buffered saline solution (Sigma, St. Louis, Mo.) and lysed for ten minutes at 4° C. in one milliliter per dish of P-RIP buffer (20 mM Tris pH 8.0, 100 mM sodium chloride, 1 mM disodium ethylenediaminetetraacetic acid, 0.5% Nonidet P-40, 0.5% sodium deoxycholate, 10 mM sodium iodide, 1% bovine serum albumin, 50 mM sodium fluoride, 30 mM tetrasodium pyrophosphate, 250 mM sodium orthovanadate, and 1 mM phenylmethylsulfonyl fluoride (all reagents from Sigma, St. Louis, Mo.)). The lysates are clarified by centrifugation at 10,000×g for ten minutes and sodium dodecyl sulfate (Sigma, St. Louis, Mo.) is added to 0.1% final concentration from a 10% stock solution (the resulting buffer is called P-RIPS: P-RIP supplemented with 0.1% sodium dodecyl sulfate). 100 $\mu$l of PANSORBIN (a 10% solution of S. aureus cells; Pansorbin: Calbiochem, La Jolla, Calif.) is added and tubes are incubated for 30 minutes on ice. The PANSORBIN is removed by centrifugation at 10,000×g for three minutes and the supernatants are transferred to new tubes containing a 1:100 dilution of rabbit anti-BRK-2 polyclonal antisera obtained as described in Example 8 above, except that the BRK-2 antibody that is used for this assay is generated against the peptide ARPRYSIGLEQDETYIPPC, (SEQ ID NO:39) which is based on the amino acid sequence of BRK-2 in the intracellular juxtamembrane region, comprising amino acids 155–172 in SEQ ID NO: 14, with the addition of a cysteine at the C terminus to permit conjugation of the peptide, as described in Example 8, above. Following an overnight incubation at 4° C., 50 microliters of Pansorbin is added and incubated for an additional 30 minutes at 4° C. The Pansorbin-bound complexes are pelleted by centrifugation at 10,000×g for three minutes and the pellets are washed three times with P-RIPS buffer and once with P-TNEN buffer (20 mM Tris pH 8.0, 100 mM sodium chloride, 1 mM disodium ethylenediaminetetraacetic acid, 0.5% Nonidet P-40, 50 mM sodium fluoride, 30 mM tetrasodium pyrophosphate, 250 mM sodium orthovanadate, and 1 mM phenylmethylsulfonyl fluoride). The pellets are then resuspended in 20 microliters per tube of SDS-PAGE sample buffer (5 Prime-3 Prime, Boulder, Colo.: 50 mM Tris pH 6.8, 2% sodium dodecyl sulfate, 0.1 M dithiothreitol, 0.1% bromophenol blue, 10% glycerol), heated at 95° C. for five minutes, and pelleted by centrifugation at 10,000×g for three minutes. The supernatants are electrophoresed through a 7.5%, 12.5%, or 15% SDS-polyacrylamide gel (Integrated Separation Systems, Natick, Mass.) at a current of 35 milliamps per gel in an electrophoretic running buffer consisting of 25 mM Tris pH 8.5, 192 mM glycine, and 0.1% sodium dodecyl sulfate (Integrated Separation Systems, Natick, Mass.). The gels are fixed for 15 minutes in a 40% methanol/10% acetic acid solution, dried, and either exposed for autoradiography at −80° C. or subjected to PhosphorImager analysis (Molecular Dynamics, Sunnyvale, Calif.).

Test compounds which are agonists of the BRK-2/BRK-3 receptor complex will cause an increase in phosphorylation of the proteins immunoprecipitated by antibodies to the BRK-2 receptor, as judged by an increased labeling of the proteins with [$^{32}$p]. In order to test for antagonist activity, test compounds are added in the presence of a fixed concentration of BMP-4 or another BMP receptor agonist. Test compounds which are antagonists of the BRK-2/BRK-3 complex will cause a decrease in the labeling of the proteins present in the BRK-2 immunoprecipitate in comparison to that observed after stimulation of the cells with only the fixed concentration of BMP-4, or another BMP receptor agonist.

Deposit of BRK-3, t-BRK-3 and m-BRK-3

E. coli transformed with pJT4-J159F (SEQ ID NO:11 subcloned into expression vector pJT4) was deposited with the ATCC on Oct. 7, 1993, and assigned ATCC Designation No. 69457.

E. coli transformed with pJT4-hBRK3T (SEQ ID NO:3 subcloned into expression vector pJT4) was deposited with the ATCC on Aug. 16, 1994 and assigned ATCC designation No. 69676.

E. coli transformed with pJT6-mBRK-3S (SEQ ID NO: 7 subcloned into expression vector pJT6) was deposited with the ATCC on Sep. 28, 1994 and assigned ATCC designation No. 69694.

E. coli transformed with pJT6-mBRK-3L (SEQ ID NO:7 subcloned into expression vector pJT6) was deposited with the ATCC on Sep. 28, 1994 and assigned ATCC designation No. 69695.

E. coli transformed with pHSK1040 (SEQ ID NO:1 subcloned into BLUESCRIPT II SK(-) was deposited with the ATCC on Oct. 12, 1994, and assigned ATCC designation No. 69703.

As is recognized in the art, there are occasionally errors in DNA and amino acid sequencing methods. As a result, the sequences encoded in the deposited material are incorporated herein by reference and controlling in the event of an error in any of the sequences found in the written description of the present invention. It is further noted that one of ordinary skill in the art reproducing Applicants' work from the written disclosure can discover any sequencing errors using routine skill. The deposit of ATCC No. 69457, ATCC No. 69676, ATCC No. 69694, ATCC No. 69695 and ATCC No. 69703 is not to be considered as an admission that the deposited material is essential to the practice of the present invention.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A method for determining whether a compound is capable of binding to a BMP receptor kinase protein complex, wherein the complex is comprised of a BMP type I receptor kinase protein and BMP receptor kinase protein BRK-3, the method comprising:
   (a) providing a BMP receptor kinase protein complex, a sample comprising the compound, and a labeled BMP;
   (b) bringing the sample comprising the compound into contact with the BMP receptor kinase protein complex and the labeled BMP;
   (c) allowing the compound and the labeled BMP to bind to the BMP receptor kinase protein complex under equilibrium conditions;
   (d) and detecting the binding of the compound to the BMP receptor kinase protein complex by measuring the amount of unbound labeled BMP, and comparing the unbound labeled BMP to a known BMP standard; and wherein said BMP receptor kinase protein BRK-3 is selected from the group consisting of SEQ ID NO: 2, SEQ ID NO: 6, SEQ ID NO: 24, SEQ ID NO: 4, SEQ ID NO: 8, SEQ ID NO: 10 and SEQ ID NO: 26.

2. The method of claim 1, wherein the BMP receptor kinase protein BRK-3 has the amino acid sequence SEQ ID NO: 4.

3. The method of claim 2, wherein the BMP type I receptor kinase protein has the amino acid sequence SEQ ID NO: 12 or SEQ ID NO: 14.

4. The method of claim 3, wherein the BMP type I receptor kinase protein has the amino acid sequence SEQ ID NO: 14.

5. The method of claim 1, wherein the BMP receptor kinase protein BRK-3 has the amino acid sequence SEQ ID NO: 8.

6. The method of claim 5, wherein the BMP type I receptor kinase protein has the amino acid sequence SEQ ID NO: 12 or SEQ ID NO: 14.

7. The method of claim 6, wherein the BMP type I receptor kinase protein has the amino acid sequence SEQ ID NO: 14.

* * * * *

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
    (A) LENGTH: 3603 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:1:

```
CGCCCCCCGA CCCCGGATCG AATCCCCGCC CTCCGCACCC TGGATATGTT TTCTCCCAGA      60

CCTGGATATT TTTTTGATAT CGTGAAACTA CGAGGGAAAT AATTTGGGGG ATTTCTTCTT     120

GGCTCCCTGC TTTCCCCACA GACATGCCTT CCGTTTGGAG GGCCGCGGCA CCCCGTCCGA     180

GGCGAAGGAA CCCCCCCAGC CGCGAGGGAG AGAAATGAAG GGAATTTCTG CAGCGGCATG     240

AAAGCTCTGC AGCTAGGTCC TCTCATCAGC CATTTGTCCT TTCAAACTGT ATTGTGATAC     300

GGGCAGGATC AGTCCACGGG AGAGAAGACG AGCCTCCCGG CTGTTTCTCC GCCGGTCTAC     360

TTCCCATATT TCTTTTCTTT GCCCTCCTGA TTCTTGGCTG GCCCAGGGAT GACTTCCTCG     420

CTGCAGCGGC CCTGGCGGGT GCCCTGGCTA CCATGGACCA TCCTGCTGGT CAGCACTGCG     480

GCTGCTTCGC AGAATCAAGA ACGGCTATGT GCGTTTAAAG ATCCGTATCA GCAAGACCTT     540

GGGATAGGTG AGAGTAGAAT CTCTCATGAA AATGGGACAA TATTATGCTC GAAAGGTAGC     600

ACCTGCTATG GCCTTTGGGA GAAATCAAAA GGGGACATAA ATCTTGTAAA ACAAGGATGT     660

TGGTCTCACA TTGGAGATCC CCAAGAGTGT CACTATGAAG AATGTGTAGT AACTACCACT     720

CCTCCCTCAA TTCAGAATGG AACATACCGT TTCTGCTGTT GTAGCACAGA TTTATGTAAT     780

GTCAACTTTA CTGAGAATTT TCCACCTCCT GACACAACAC CACTCAGTCC ACCTCATTCA     840

TTTAACCGAG ATGAGACAAT AATCATTGCT TTGGCATCAG TCTCTGTATT AGCTGTTTTG     900

ATAGTTGCCT TATGCTTTGG ATACAGAATG TTGACAGGAG ACCGTAAACA AGGTCTTCAC     960

AGTATGAACA TGATGGAGGC AGCAGCATCC GAACCCTCTC TTGATCTAGA TAATCTGAAA    1020

CTGTTGGAGC TGATTGGCCG AGGTCGATAT GGAGCAGTAT ATAAAGGCTC CTTGGATGAG    1080

CGTCCAGTTG CTGTAAAAGT GTTTTCCTTT GCAAACCGTC AGAATTTTAT CAACGAAAAG    1140
```

-continued

```
AACATTTACA GAGTGCCTTT GATGGAACAT GACAACATTG CCCGCTTTAT AGTTGGAGAT    1200

GAGAGAGTCA CTGCAGATGG ACGCATGGAA TATTTGCTTG TGATGGAGTA CTATCCCAAT    1260

GGATCTTTAT GCAAGTATTT AAGTCTCCAC ACAAGTGACT GGGTAAGCTC TTGCCGTCTT    1320

GCTCATTCTG TTACTAGAGG ACTGGCTTAT CTTCACACAG AATTACCACG AGGAGATCAT    1380

TATAAACCTG CAATTTCCCA TCGAGATTTA ACAGCAGAA ATGTCCTAGT GAAAAATGAT     1440

GGAACCTGTG TTATTAGTGA CTTTGGACTG TCCATGAGGC TGACTGGAAA TAGACTGGTG    1500

CGCCCAGGGG AGGAAGATAA TGCAGCCATA AGCGAGGTTG GCACTATCAG ATATATGGCA    1560

CCAGAAGTGC TAGAAGGAGC TGTGAACTTG AGGGACTGTG AATCAGCTTT GAAACAAGTA    1620

GACATGTATG CTCTTGGACT AATCTATTGG GAGATATTTA TGAGATGTAC AGACCTCTTC    1680

CCAGGGGAAT CCGTACCAGA GTACCAGATG GCTTTTCAGA CAGAGGTTGG AAACCATCCC    1740

ACTTTTGAGG ATATGCAGGT TCTCGTGTCT AGGGAAAAAC AGAGACCCAA GTTCCCAGAA    1800

GCCTGGAAAG AAAATAGCCT GGCAGTGAGG TCACTCAAGG AGACAATCGA AGACTGTTGG    1860

GACCAGGATG CAGAGGCTCG GCTTACTGCA CAGTGTGCTG AGGAAAGGAT GGCTGAACTT    1920

ATGATGATTT GGGAAAGAAA CAAATCTGTG AGCCCAACAG TCAATCCAAT GTCTACTGCT    1980

ATGCAGAATG AACGCAACCT GTCACATAAT AGGCGTGTGC CAAAAATTGG TCCTTATCCA    2040

GATTATTCTT CCTCCTCATA CATTGAAGAC TCTATCCATC ATACTGACAG CATCGTGAAG    2100

AATATTTCCT CTGAGCATTC TATGTCCAGC ACACCTTTGA CTATAGGGGA AAAAAACCGA    2160

AATTCAATTA ACTATGAACG ACAGCAAGCA CAAGCTCGAA TCCCCAGCCC TGAAACAAGT    2220

GTCACCAGCC TCTCCACCAA CACAACAACC ACAAACACCA CAGGACTCAC GCCAAGTACT    2280

GGCATGACTA CTATATCTGA TGCCATAC CCAGATGAAA CAAATCTGCA TACCACAAAT      2340

GTTGCACAGT CAATTGGGCC AACCCCTGTC TGCTTACAGC TGACAGAAGA AGACTTGGAA    2400

ACCAACAAGC TAGACCCAAA AGAAGTTGAT AAGAACCTCA AGGAAAGCTC TGATGAGAAT    2460

CTCATGGAGC ACTCTCTTAA ACAGTTCAGT GGCCCAGACC CACTGAGCAG TACTAGTTCT    2520

AGCTTGCTTT ACCCACTCAT AAAACTTGCA GTAGAAGCAA CTGGACAGCA GGACTTCACA    2580

CAGACTGCAA ATGGCCAAGC ATGTTTGATT CCTGATGTTC TGCCTACTCA GATCTATCCT    2640

CTCCCCAAGC AGCAGAACCT TCCCAAGAGA CCTACTAGTT TGCCTTTGAA CACCAAAAAT    2700

TCAACAAAAG AGCCCCGGCT AAAATTTGGC AGCAAGCACA AATCAAACTT GAAACAAGTC    2760

GAAACTGGAG TTGCCAAGAT GAATACAATC AATGCAGCAG AACCTCATGT GGTGACAGTC    2820

ACCATGAATG GTGTGGCAGG TAGAAACCAC AGTGTTAACT CCCATGCTGC CACAACCCAA    2880

TATGCCAATG GGACAGTACT ATCTGGCCAA ACAACCAACA TAGTGCACACA TAGGGCCCAA   2940

GAAATGTTGC AGAATCAGTT TATTGGTGAG GACACCCGGC TGAATATTAA TTCCAGTCCT    3000

GATGAGCATG AGCCTTTACT GAGACGAGAG CAACAAGCTG GCCATGATGA AGGTGTTCTG    3060

GATCGTCTTG TGGACAGGAG GGAACGGCCA CTAGAAGGTG GCCGAACTAA TTCCAATAAC    3120

AACAACAGCA ATCCATGTTC AGAACAAGAT GTTCTTGCAC AGGGTGTTCC AAGCACAGCA    3180

GCAGATCCTG GGCCATCAAA GCCCAGAAGA GCACAGAGGC CTAATTCTCT GGATCTTTCA    3240

GCCACAAATG TCCTGGATGG CAGCAGTATA CAGATAGGTG AGTCAACACA AGATGGCAAA    3300

TCAGGATCAG GTGAAAAGAT CAAGAAACGT GTGAAAACTC CCTATTCTCT TAAGCGGTGG    3360

CGCCCCTCCA CCTGGGTCAT CTCCACTGAA TCGTTCTGGA CTGTGAAGTC AACAATAATG    3420

GCAGTAACAG GGCAGTTCAT TCCAAATCCA GCACTGCTGT TTACCTTGCA GAAGGAGGCA    3480
```

```
CTGCTACAAC CATGGTGTCT AAAGATATAG GAATGAACTG TCTGTGAAAT GTTTTCAAGC    3540

CTATGGAGTG AAATTATTTT TTGCATCATT TAAACATGCA GAAGATGTTT AAAAAAAAAA    3600

AAA                                                                  3603
```

(2) INFORMATION FOR SEQ ID NO:2:

(i) SEQUENCE CHARACTERISTICS:
        (A) LENGTH: 2887 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:2:

```
Met Glu Thr Thr His Arg Ser Glu Arg Ser Glu Arg Leu Glu Gly Leu
 1               5                  10                  15

Asn Ala Arg Gly Pro Arg Thr Arg Pro Ala Arg Gly Val Ala Leu Pro
            20                  25                  30

Arg Thr Arg Pro Leu Glu Pro Arg Thr Arg Pro Thr His Arg Ile Leu
        35                  40                  45

Glu Leu Glu Leu Glu Val Ala Leu Ser Glu Arg Thr His Arg Ala Leu
    50                  55                  60

Ala Ala Leu Ala Ala Leu Ala Ser Glu Arg Gly Leu Asn Ala Ser Asn
65                  70                  75                  80

Gly Leu Asn Gly Leu Ala Arg Gly Leu Glu Cys Tyr Ser Ala Leu Ala
                85                  90                  95

Pro His Glu Leu Tyr Ser Ala Ser Pro Pro Arg Thr Tyr Arg Gly Leu
            100                 105                 110

Asn Gly Leu Asn Ala Ser Pro Leu Glu Gly Leu Tyr Ile Leu Glu Gly
        115                 120                 125

Leu Tyr Gly Leu Ser Glu Arg Ala Arg Gly Ile Leu Glu Ser Glu Arg
    130                 135                 140

His Ile Ser Gly Leu Ala Ser Asn Gly Leu Tyr Thr His Arg Ile Leu
145                 150                 155                 160

Glu Leu Glu Cys Tyr Ser Ser Glu Arg Leu Tyr Ser Gly Leu Tyr Ser
                165                 170                 175

Glu Arg Thr His Arg Cys Tyr Ser Thr Tyr Arg Gly Leu Tyr Leu Glu
            180                 185                 190

Thr Arg Pro Gly Leu Leu Tyr Ser Ser Glu Arg Leu Tyr Ser Gly Leu
        195                 200                 205

Tyr Ala Ser Pro Ile Leu Glu Ala Ser Asn Leu Glu Val Ala Leu Leu
    210                 215                 220

Tyr Ser Gly Leu Asn Gly Leu Tyr Cys Tyr Ser Thr Arg Pro Ser Glu
225                 230                 235                 240

Arg His Ile Ser Ile Leu Glu Gly Leu Tyr Ala Ser Pro Pro Arg Gly
                245                 250                 255

Leu Asn Gly Leu Cys Tyr Ser His Ile Ser Thr Tyr Arg Gly Leu Gly
            260                 265                 270

Leu Cys Tyr Ser Val Ala Leu Val Ala Leu Thr His Arg Thr His Arg
        275                 280                 285

Thr His Arg Pro Arg Pro Arg Ser Glu Arg Ile Leu Glu Gly Leu Asn
    290                 295                 300

Ala Ser Asn Gly Leu Tyr Thr His Arg Thr Tyr Arg Ala Arg Gly Pro
305                 310                 315                 320
```

-continued

```
His Glu Cys Tyr Ser Cys Tyr Ser Cys Tyr Ser Ser Glu Arg Thr His
            325                 330                 335

Arg Ala Ser Pro Leu Glu Cys Tyr Ser Ala Ser Asn Val Ala Leu Ala
            340                 345                 350

Ser Asn Pro His Glu Thr His Arg Gly Leu Ala Ser Asn Pro His Glu
            355                 360                 365

Pro Arg Pro Arg Pro Arg Ala Ser Pro Thr His Arg Thr His Arg Pro
370                 375                 380

Arg Leu Glu Ser Glu Arg Pro Arg Pro Arg His Ile Ser Ser Glu Arg
385                 390                 395                 400

Pro His Glu Ala Ser Asn Ala Arg Gly Ala Ser Pro Gly Leu Thr His
            405                 410                 415

Arg Ile Leu Glu Ile Leu Glu Ile Leu Glu Ala Leu Ala Leu Glu Ala
            420                 425                 430

Leu Ala Ser Glu Arg Val Ala Leu Ser Glu Arg Val Ala Leu Leu Glu
            435                 440                 445

Ala Leu Ala Val Ala Leu Leu Glu Ile Leu Glu Val Ala Leu Ala Leu
450                 455                 460

Ala Leu Glu Cys Tyr Ser Pro His Glu Gly Leu Tyr Thr Tyr Arg Ala
465                 470                 475                 480

Arg Gly Met Glu Thr Leu Glu Thr His Arg Gly Leu Tyr Ala Ser Pro
            485                 490                 495

Ala Arg Gly Leu Tyr Ser Gly Leu Asn Gly Leu Tyr Leu Glu His Ile
            500                 505                 510

Ser Ser Glu Arg Met Glu Thr Ala Ser Asn Met Glu Thr Met Glu Thr
            515                 520                 525

Gly Leu Ala Leu Ala Ala Leu Ala Ala Leu Ala Ser Glu Arg Gly Leu
            530                 535                 540

Pro Arg Ser Glu Arg Leu Glu Ala Ser Pro Leu Glu Ala Ser Pro Ala
545                 550                 555                 560

Ser Asn Leu Glu Leu Tyr Ser Leu Glu Leu Glu Gly Leu Leu Glu Ile
            565                 570                 575

Leu Glu Gly Leu Tyr Ala Arg Gly Gly Leu Tyr Ala Arg Gly Thr Tyr
            580                 585                 590

Arg Gly Leu Tyr Ala Leu Ala Val Ala Leu Thr Tyr Arg Leu Tyr Ser
            595                 600                 605

Gly Leu Tyr Ser Glu Arg Leu Glu Ala Ser Pro Gly Leu Ala Arg Gly
            610                 615                 620

Pro Arg Val Ala Leu Ala Leu Ala Val Ala Leu Leu Tyr Ser Val Ala
625                 630                 635                 640

Leu Pro His Glu Ser Glu Arg Pro His Glu Ala Leu Ala Ala Ser Asn
            645                 650                 655

Ala Arg Gly Gly Leu Asn Ala Ser Asn Pro His Glu Ile Leu Glu Ala
            660                 665                 670

Ser Asn Gly Leu Leu Tyr Ser Ala Ser Asn Ile Leu Glu Thr Tyr Arg
            675                 680                 685

Ala Arg Gly Val Ala Leu Pro Arg Leu Glu Met Glu Thr Gly Leu His
690                 695                 700

Ile Ser Ala Ser Pro Ala Ser Asn Ile Leu Glu Ala Leu Ala Ala Arg
705                 710                 715                 720

Gly Pro His Glu Ile Leu Glu Val Ala Leu Gly Leu Tyr Ala Ser Pro
            725                 730                 735

Gly Leu Ala Arg Gly Val Ala Leu Thr His Arg Ala Leu Ala Ala Ser
```

-continued

```
                740               745               750
Pro Gly Leu Tyr Ala Arg Gly Met Glu Thr Gly Leu Thr Tyr Arg Leu
                    755               760               765
Glu Leu Glu Val Ala Leu Met Glu Thr Gly Leu Thr Tyr Arg Thr Tyr
            770               775               780
Arg Pro Arg Ala Ser Asn Gly Leu Tyr Ser Glu Arg Leu Glu Cys Tyr
785               790               795               800
Ser Leu Tyr Ser Thr Tyr Arg Leu Glu Ser Glu Arg Leu Glu His Ile
                805               810               815
Ser Thr His Arg Ser Glu Arg Ala Ser Pro Thr Arg Pro Val Ala Leu
                    820               825               830
Ser Glu Arg Ser Glu Arg Cys Tyr Ser Ala Arg Gly Leu Glu Ala Leu
            835               840               845
Ala His Ile Ser Ser Glu Arg Val Ala Leu Thr His Arg Ala Arg Gly
        850               855               860
Gly Leu Tyr Leu Glu Ala Leu Ala Thr Tyr Arg Leu Glu His Ile Ser
865               870               875               880
Thr His Arg Gly Leu Leu Glu Pro Arg Ala Arg Gly Gly Leu Tyr Ala
                    885               890               895
Ser Pro His Ile Ser Thr Tyr Arg Leu Tyr Ser Pro Arg Ala Leu Ala
                900               905               910
Ile Leu Glu Ser Glu Arg His Ile Ser Ala Arg Gly Ala Ser Pro Leu
                915               920               925
Glu Ala Ser Asn Ser Glu Arg Ala Arg Gly Ala Ser Asn Val Ala Leu
            930               935               940
Leu Glu Val Ala Leu Leu Tyr Ser Ala Ser Asn Ala Ser Pro Gly Leu
945               950               955               960
Tyr Thr His Arg Cys Tyr Ser Val Ala Leu Ile Leu Glu Ser Glu Arg
                965               970               975
Ala Ser Pro Pro His Glu Gly Leu Tyr Leu Glu Ser Glu Arg Met Glu
                980               985               990
Thr Ala Arg Gly Leu Glu Thr His Arg Gly Leu Tyr Ala Ser Asn Ala
                995               1000              1005
Arg Gly Leu Glu Val Ala Leu Ala Arg Gly Pro Arg Gly Leu Tyr Gly
    1010              1015              1020
Leu Gly Leu Ala Ser Pro Ala Ser Asn Ala Leu Ala Ala Leu Ala Ile
1025              1030              1035              1040
Leu Glu Ser Glu Arg Gly Leu Val Ala Leu Gly Leu Tyr Thr His Arg
                    1045              1050              1055
Ile Leu Glu Ala Arg Gly Thr Tyr Arg Met Glu Thr Ala Leu Ala Pro
                1060              1065              1070
Arg Gly Leu Val Ala Leu Leu Glu Gly Leu Gly Leu Tyr Ala Leu Ala
            1075              1080              1085
Val Ala Leu Ala Ser Asn Leu Glu Ala Arg Gly Ala Ser Pro Cys Tyr
        1090              1095              1100
Ser Gly Leu Ser Glu Arg Ala Leu Ala Leu Glu Leu Tyr Ser Gly Leu
1105              1110              1115              1120
Asn Val Ala Leu Ala Ser Pro Met Glu Thr Thr Tyr Arg Ala Leu Ala
                    1125              1130              1135
Leu Glu Gly Leu Tyr Leu Glu Ile Leu Glu Thr Tyr Arg Thr Arg Pro
                1140              1145              1150
Gly Leu Ile Leu Glu Pro His Glu Met Glu Thr Ala Arg Gly Cys Tyr
            1155              1160              1165
```

```
Ser Thr His Arg Ala Ser Pro Leu Glu Pro His Glu Pro Arg Gly Leu
    1170                1175                1180
Tyr Gly Leu Ser Glu Arg Val Ala Leu Pro Arg Gly Leu Thr Tyr Arg
1185                1190                1195                1200
Gly Leu Asn Met Glu Thr Ala Leu Ala Pro His Glu Gly Leu Asn Thr
            1205                1210                1215
His Arg Gly Leu Val Ala Leu Gly Leu Tyr Ala Ser Asn His Ile Ser
            1220                1225                1230
Pro Arg Thr His Arg Pro His Glu Gly Leu Ala Ser Pro Met Glu Thr
            1235                1240                1245
Gly Leu Asn Val Ala Leu Leu Glu Val Ala Leu Ser Glu Arg Ala Arg
    1250                1255                1260
Gly Gly Leu Leu Tyr Ser Gly Leu Asn Ala Arg Gly Pro Arg Leu Tyr
1265                1270                1275                1280
Ser Pro His Glu Pro Arg Gly Leu Ala Leu Ala Thr Arg Pro Leu Tyr
            1285                1290                1295
Ser Gly Leu Ala Ser Asn Ser Glu Arg Leu Glu Ala Leu Ala Val Ala
            1300                1305                1310
Leu Ala Arg Gly Ser Glu Arg Leu Glu Leu Tyr Ser Gly Leu Thr His
            1315                1320                1325
Arg Ile Leu Glu Gly Leu Ala Ser Pro Cys Tyr Ser Thr Arg Pro Ala
    1330                1335                1340
Ser Pro Gly Leu Asn Ala Ser Pro Ala Leu Ala Gly Leu Ala Leu Ala
1345                1350                1355                1360
Ala Arg Gly Leu Glu Thr His Arg Ala Leu Ala Gly Leu Asn Cys Tyr
            1365                1370                1375
Ser Ala Leu Ala Gly Leu Gly Leu Ala Arg Gly Met Glu Thr Ala Leu
            1380                1385                1390
Ala Gly Leu Leu Glu Met Glu Thr Met Glu Thr Ile Leu Glu Thr Arg
            1395                1400                1405
Pro Gly Leu Ala Arg Gly Ala Ser Asn Leu Tyr Ser Ser Glu Arg Val
    1410                1415                1420
Ala Leu Ser Glu Arg Pro Arg Thr His Arg Val Ala Leu Ala Ser Asn
1425                1430                1435                1440
Pro Arg Met Glu Thr Ser Glu Arg Thr His Arg Ala Leu Ala Met Glu
            1445                1450                1455
Thr Gly Leu Asn Ala Ser Asn Gly Leu Ala Arg Gly Ala Ser Asn Leu
            1460                1465                1470
Glu Ser Glu Arg His Ile Ser Ala Ser Asn Ala Arg Gly Ala Arg Gly
            1475                1480                1485
Val Ala Leu Pro Arg Leu Tyr Ser Ile Leu Glu Gly Leu Tyr Pro Arg
            1490                1495                1500
Thr Tyr Arg Pro Arg Ala Ser Pro Thr Tyr Arg Ser Glu Arg Ser Glu
1505                1510                1515                1520
Arg Ser Glu Arg Ser Glu Arg Thr Tyr Arg Ile Leu Glu Gly Leu Ala
            1525                1530                1535
Ser Pro Ser Glu Arg Ile Leu Glu His Ile Ser His Ile Ser Thr His
            1540                1545                1550
Arg Ala Ser Pro Ser Glu Arg Ile Leu Glu Val Ala Leu Leu Tyr Ser
    1555                1560                1565
Ala Ser Asn Ile Leu Glu Ser Glu Arg Ser Glu Arg Gly Leu His Ile
    1570                1575                1580
```

-continued

```
Ser Ser Glu Arg Met Glu Thr Ser Glu Arg Ser Glu Arg Thr His Arg
1585                1590                1595                1600

Pro Arg Leu Glu Thr His Arg Ile Leu Glu Gly Leu Tyr Gly Leu Leu
                1605                1610                1615

Tyr Ser Ala Ser Asn Ala Arg Gly Ala Ser Asn Ser Glu Arg Ile Leu
            1620                1625                1630

Glu Ala Ser Asn Thr Tyr Arg Gly Leu Ala Arg Gly Gly Leu Asn Gly
        1635                1640                1645

Leu Asn Ala Leu Ala Gly Leu Asn Ala Leu Ala Arg Gly Ile Leu
    1650                1655                1660

Glu Pro Arg Ser Glu Arg Pro Arg Gly Leu Thr His Arg Ser Glu Arg
1665                1670                1675                1680

Val Ala Leu Thr His Arg Ser Glu Arg Leu Glu Ser Glu Arg Thr His
                1685                1690                1695

Arg Ala Ser Asn Thr His Arg Thr His Arg Thr His Arg Thr His Arg
            1700                1705                1710

Ala Ser Asn Thr His Arg Thr His Arg Gly Leu Tyr Leu Glu Thr His
        1715                1720                1725

Arg Pro Arg Ser Glu Arg Thr His Arg Gly Leu Tyr Met Glu Thr Thr
    1730                1735                1740

His Arg Thr His Arg Ile Leu Glu Ser Glu Arg Gly Leu Met Glu Thr
1745                1750                1755                1760

Pro Arg Thr Tyr Arg Pro Arg Ala Ser Pro Gly Leu Thr His Arg Ala
                1765                1770                1775

Ser Asn Leu Glu His Ile Ser Thr His Arg Thr His Arg Ala Ser Asn
            1780                1785                1790

Val Ala Leu Ala Leu Ala Gly Leu Asn Ser Glu Arg Ile Leu Glu Gly
        1795                1800                1805

Leu Tyr Pro Arg Thr His Arg Pro Arg Val Ala Leu Cys Tyr Ser Leu
    1810                1815                1820

Glu Gly Leu Asn Leu Glu Thr His Arg Gly Leu Gly Leu Ala Ser Pro
1825                1830                1835                1840

Leu Glu Gly Leu Thr His Arg Ala Ser Asn Leu Tyr Ser Leu Glu Ala
                1845                1850                1855

Ser Pro Pro Arg Leu Tyr Ser Gly Leu Val Ala Leu Ala Ser Pro Leu
            1860                1865                1870

Tyr Ser Ala Ser Asn Leu Glu Leu Tyr Ser Gly Leu Ser Glu Arg Ser
        1875                1880                1885

Glu Arg Ala Ser Pro Gly Leu Ala Ser Asn Leu Glu Met Glu Thr Gly
    1890                1895                1900

Leu His Ile Ser Ser Glu Arg Leu Glu Leu Tyr Ser Gly Leu Asn Pro
1905                1910                1915                1920

His Glu Ser Glu Arg Gly Leu Tyr Pro Arg Ala Ser Pro Pro Arg Leu
                1925                1930                1935

Glu Ser Glu Arg Ser Glu Arg Thr His Arg Ser Glu Arg Ser Glu Arg
            1940                1945                1950

Ser Glu Arg Leu Glu Leu Glu Thr Tyr Arg Pro Arg Leu Glu Ile Leu
        1955                1960                1965

Glu Leu Tyr Ser Leu Glu Ala Leu Ala Val Ala Leu Gly Leu Ala Leu
    1970                1975                1980

Ala Thr His Arg Gly Leu Tyr Gly Leu Asn Gly Leu Asn Ala Ser Pro
1985                1990                1995                2000

Pro His Glu Thr His Arg Gly Leu Asn Thr His Arg Ala Leu Ala Ala
```

-continued

```
                  2005                2010                2015
Ser Asn Gly Leu Tyr Gly Leu Asn Ala Leu Ala Cys Tyr Ser Leu Glu
                2020                2025                2030

Ile Leu Glu Pro Arg Ala Ser Pro Val Ala Leu Leu Glu Pro Arg Thr
        2035                2040                2045

His Arg Gly Leu Asn Ile Leu Glu Thr Tyr Arg Pro Arg Leu Glu Pro
    2050                2055                2060

Arg Leu Tyr Ser Gly Leu Asn Gly Leu Asn Ala Ser Asn Leu Glu Pro
2065                2070                2075                2080

Arg Leu Tyr Ser Ala Arg Gly Pro Arg Thr His Arg Ser Glu Arg Leu
                2085                2090                2095

Glu Pro Arg Leu Glu Ala Ser Asn Thr His Arg Leu Tyr Ser Ala Ser
                2100                2105                2110

Asn Ser Glu Arg Thr His Arg Leu Tyr Ser Gly Leu Pro Arg Ala Arg
            2115                2120                2125

Gly Leu Glu Leu Tyr Ser Pro His Glu Gly Leu Tyr Ser Glu Arg Leu
        2130                2135                2140

Tyr Ser His Ile Ser Leu Tyr Ser Ser Glu Arg Ala Ser Asn Leu Glu
2145                2150                2155                2160

Leu Tyr Ser Gly Leu Asn Val Ala Leu Gly Leu Thr His Arg Gly Leu
                2165                2170                2175

Tyr Val Ala Leu Ala Leu Ala Leu Tyr Ser Met Glu Thr Ala Ser Asn
            2180                2185                2190

Thr His Arg Ile Leu Glu Ala Ser Asn Ala Leu Ala Ala Leu Ala Gly
        2195                2200                2205

Leu Pro Arg His Ile Ser Val Ala Leu Val Ala Leu Thr His Arg Val
    2210                2215                2220

Ala Leu Thr His Arg Met Glu Thr Ala Ser Asn Gly Leu Tyr Val Ala
2225                2230                2235                2240

Leu Ala Leu Ala Gly Leu Tyr Ala Arg Gly Ala Ser Asn His Ile Ser
                2245                2250                2255

Ser Glu Arg Val Ala Leu Ala Ser Asn Ser Glu Arg His Ile Ser Ala
            2260                2265                2270

Leu Ala Ala Leu Ala Thr His Arg Thr His Arg Gly Leu Asn Thr Tyr
        2275                2280                2285

Arg Ala Leu Ala Ala Ser Asn Gly Leu Tyr Thr His Arg Val Ala Leu
    2290                2295                2300

Leu Glu Ser Glu Arg Gly Leu Tyr Gly Leu Asn Thr His Arg Thr His
2305                2310                2315                2320

Arg Ala Ser Asn Ile Leu Glu Val Ala Leu Thr His Arg His Ile Ser
            2325                2330                2335

Ala Arg Gly Ala Leu Ala Gly Leu Asn Gly Leu Met Glu Thr Leu Glu
        2340                2345                2350

Gly Leu Asn Ala Ser Asn Gly Leu Asn Pro His Glu Ile Leu Glu Gly
        2355                2360                2365

Leu Tyr Gly Leu Ala Ser Pro Thr His Arg Ala Arg Gly Leu Glu Ala
    2370                2375                2380

Ser Asn Ile Leu Glu Ala Ser Asn Ser Glu Arg Ser Glu Arg Pro Arg
2385                2390                2395                2400

Ala Ser Pro Gly Leu His Ile Ser Gly Leu Pro Arg Leu Glu Leu Glu
                2405                2410                2415

Ala Arg Gly Ala Arg Gly Gly Leu Gly Leu Asn Gly Leu Asn Ala Leu
            2420                2425                2430
```

-continued

```
Ala Gly Leu Tyr His Ile Ser Ala Ser Pro Gly Leu Gly Leu Tyr Val
            2435                2440                2445
Ala Leu Leu Glu Ala Ser Pro Ala Arg Gly Leu Glu Val Ala Leu Ala
            2450                2455                2460
Ser Pro Ala Arg Gly Ala Arg Gly Leu Ala Arg Gly Pro Arg Leu
2465            2470                2475                2480
Glu Gly Leu Gly Leu Tyr Gly Leu Tyr Ala Arg Gly Thr His Arg Ala
            2485                2490                2495
Ser Asn Ser Glu Arg Ala Ser Asn Ala Ser Asn Ala Ser Asn Ala Ser
            2500                2505                2510
Asn Ser Glu Arg Ala Ser Asn Pro Arg Cys Tyr Ser Ser Glu Arg Gly
            2515                2520                2525
Leu Gly Leu Asn Ala Ser Pro Val Ala Leu Leu Glu Ala Leu Ala Gly
            2530                2535                2540
Leu Asn Gly Leu Tyr Val Ala Leu Pro Arg Ser Glu Arg Thr His Arg
2545            2550                2555                2560
Ala Leu Ala Ala Leu Ala Ala Ser Pro Pro Arg Gly Leu Tyr Pro Arg
            2565                2570                2575
Ser Glu Arg Leu Tyr Ser Pro Arg Ala Arg Gly Ala Arg Gly Ala Leu
            2580                2585                2590
Ala Gly Leu Asn Ala Arg Gly Pro Arg Ala Ser Asn Ser Glu Arg Leu
            2595                2600                2605
Glu Ala Ser Pro Leu Glu Ser Glu Arg Ala Leu Ala Thr His Arg Ala
            2610                2615                2620
Ser Asn Val Ala Leu Leu Glu Ala Ser Pro Gly Leu Tyr Ser Glu Arg
2625            2630                2635                2640
Ser Glu Arg Ile Leu Glu Gly Leu Asn Ile Leu Glu Gly Leu Tyr Gly
            2645                2650                2655
Leu Ser Glu Arg Thr His Arg Gly Leu Asn Ala Ser Pro Gly Leu Tyr
            2660                2665                2670
Leu Tyr Ser Ser Glu Arg Gly Leu Tyr Ser Glu Arg Gly Leu Tyr Gly
            2675                2680                2685
Leu Leu Tyr Ser Ile Leu Glu Leu Tyr Ser Leu Tyr Ser Ala Arg Gly
            2690                2695                2700
Val Ala Leu Leu Tyr Ser Thr His Arg Pro Arg Thr Tyr Arg Ser Glu
2705            2710                2715                2720
Arg Leu Glu Leu Tyr Ser Ala Arg Gly Thr Arg Pro Ala Arg Gly Pro
            2725                2730                2735
Arg Ser Glu Arg Thr His Arg Thr Arg Pro Val Ala Leu Ile Leu Glu
            2740                2745                2750
Ser Glu Arg Thr His Arg Gly Leu Ser Glu Arg Leu Glu Ala Ser Pro
            2755                2760                2765
Cys Tyr Ser Gly Leu Val Ala Leu Ala Ser Asn Ala Ser Asn Ala Ser
            2770                2775                2780
Asn Gly Leu Tyr Ser Glu Arg Ala Ser Asn Ala Arg Gly Ala Leu Ala
2785            2790                2795                2800
Val Ala Leu His Ile Ser Ser Glu Arg Leu Tyr Ser Ser Glu Arg Ser
            2805                2810                2815
Glu Arg Thr His Arg Ala Leu Ala Val Ala Leu Thr Tyr Arg Leu Glu
            2820                2825                2830
Ala Leu Ala Gly Leu Gly Leu Tyr Gly Leu Tyr Thr His Arg Ala Leu
            2835                2840                2845
```

Ala Thr His Arg Thr His Arg Met Glu Thr Val Ala Leu Ser Glu Arg
  2850                           2855                      2860

Leu Tyr Ser Ala Ser Pro Ile Leu Glu Gly Leu Tyr Met Glu Thr Ala
2865                  2870                      2875                      2880

Ser Asn Cys Tyr Ser Leu Glu
              2885

(2) INFORMATION FOR SEQ ID NO:3:

(i) SEQUENCE CHARACTERISTICS:
        (A) LENGTH: 2156 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CGCCCCCCGA CCCCGGATCG AATCCCCGCC CTCCGCACCC TGGATATGTT TTCTCCCAGA      60

CCTGGATATT TTTTTGATAT CGTGAAACTA CGAGGGAAAT AATTTGGGGG ATTTCTTCTT     120

GGCTCCCTGC TTTCCCCACA GACATGCCTT CCGTTTGGAG GGCCGCGGCA CCCCGTCCGA     180

GGCGAAGGAA CCCCCCCAGC CGCGAGGGAG AGAAATGAAG GGAATTTCTG CAGCGGCATG     240

AAAGCTCTGC AGCTAGGTCC TCTCATCAGC CATTTGTCCT TTCAAACTGT ATTGTGATAC     300

GGGCAGGATC AGTCCACGGG AGAGAAGACG AGCCTCCCGG CTGTTTCTCC GCCGGTCTAC     360

TTCCCATATT TCTTTTCTTT GCCCTCCTGA TTCTTGGCTG GCCCAGGGAT GACTTCCTCG     420

CTGCAGCGGC CCTGGCGGGT GCCCTGGCTA CCATGGACCA TCCTGCTGGT CAGCACTGCG     480

GCTGCTTCGC AGAATCAAGA ACGGCTATGT GCGTTTAAAG ATCCGTATCA GCAAGACCTT     540

GGGATAGGTG AGAGTAGAAT CTCTCATGAA AATGGGACAA TATTATGCTC GAAAGGTAGC     600

ACCTGCTATG GCCTTTGGGA GAAATCAAAA GGGGACATAA ATCTTGTAAA ACAAGGATGT     660

TGGTCTCACA TTGGAGATCC CCAAGAGTGT CACTATGAAG AATGTGTAGT AACTACCACT     720

CCTCCCTCAA TTCAGAATGG AACATACCGT TTCTGCTGTT GTAGCACAGA TTTATGTAAT     780

GTCAACTTTA CTGAGAATTT TCCACCTCCT GACACAACAC CACTCAGTCC ACCTCATTCA     840

TTTAACCGAG ATGAGACAAT AATCATTGCT TTGGCATCAG TCTCTGTATT AGCTGTTTTG     900

ATAGTTGCCT TATGCTTTGG ATACAGAATG TTGACAGGAG ACCGTAAACA AGGTCTTCAC     960

AGTATGAACA TGATGGAGGC AGCAGCATCC GAACCCTCTC TTGATCTAGA TAATCTGAAA    1020

CTGTTGGAGC TGATTGGCCG AGGTCGATAT GGAGCAGTAT ATAAAGGCTC CTTGGATGAG    1080

CGTCCAGTTG CTGTAAAAGT GTTTTCCTTT GCAAACCGTC AGAATTTTAT CAACGAAAAG    1140

AACATTTACA GAGTGCCTTT GATGGAACAT GACAACATTG CCCGCTTTAT AGTTGGAGAT    1200

GAGAGAGTCA CTGCAGATGG ACGCATGGAA TATTTGCTTG TGATGGAGTA CTATCCCAAT    1260

GGATCTTTAT GCAAGTATTT AAGTCTCCAC ACAAGTGACT GGGTAAGCTC TTGCCGTCTT    1320

GCTCATTCTG TTACTAGAGG ACTGGCTTAT CTTCACACAG AATTACCACG AGGAGATCAT    1380

TATAAACCTG CAATTTCCCA TCGAGATTTA AACAGCAGAA ATGTCCTAGT GAAAAATGAT    1440

GGAACCTGTG TTATTAGTGA CTTTGGACTG TCCATGAGGC TGACTGGAAA TAGACTGGTG    1500

CGCCCAGGGG AGGAAGATAA TGCAGCCATA AGCGAGGTTG GCACTATCAG ATATATGGCA    1560

CCAGAAGTGC TAGAAGGAGC TGTGAACTTG AGGGACTGTG AATCAGCTTT GAAACAAGTA    1620

GACATGTATG CTCTTGGACT AATCTATTGG GAGATATTTA TGAGATGTAC AGACCTCTTC    1680

CCAGGGGAAT CCGTACCAGA GTACCAGATG GCTTTTCAGA CAGAGGTTGG AAACCATCCC    1740
```

```
ACTTTTGAGG ATATGCAGGT TCTCGTGTCT AGGGAAAAAC AGAGACCCAA GTTCCCAGAA    1800

GCCTGGAAAG AAAATAGCCT GGCAGTGAGG TCACTCAAGG AGACAATCGA AGACTGTTGG    1860

GACCAGGATG CAGAGGCTCG GCTTACTGCA CAGTGTGCTG AGGAAAGGAT GGCTGAACTT    1920

ATGATGATTT GGGAAAGAAA CAAATCTGTG AGCCCAACAG TCAATCCAAT GTCTACTGCT    1980

ATGCAGAATG AACGCAACCT GTCACATAAT AGGCGTGTGC CAAAAATTGG TCCTTATCCA    2040

GATTATTCTT CCTCCTCATA CATTGAAGAC TCTATCCATC ATACTGACAG CATCGTGAAG    2100

AATATTTCCT CTGAGCATTC TATGTCCAGC ACACCTTTGA CTATAGGGGA AAAAAA       2156
```

(2) INFORMATION FOR SEQ ID NO:4:

(i) SEQUENCE CHARACTERISTICS:
        (A) LENGTH: 1618 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

```
Met Glu Thr Thr His Arg Ser Glu Arg Ser Glu Arg Leu Glu Gly Leu
1               5                  10                  15

Asn Ala Arg Gly Pro Arg Thr Arg Pro Ala Arg Gly Val Ala Leu Pro
            20                  25                  30

Arg Thr Arg Pro Leu Glu Pro Arg Thr Arg Pro Thr His Arg Ile Leu
        35                  40                  45

Glu Leu Glu Leu Glu Val Ala Leu Ser Glu Arg Thr His Arg Ala Leu
    50                  55                  60

Ala Ala Leu Ala Ala Leu Ala Ser Glu Arg Gly Leu Asn Ala Ser Asn
65                  70                  75                  80

Gly Leu Asn Gly Leu Ala Arg Gly Leu Glu Cys Tyr Ser Ala Leu Ala
                85                  90                  95

Pro His Glu Leu Tyr Ser Ala Ser Pro Pro Arg Thr Tyr Arg Gly Leu
            100                 105                 110

Asn Gly Leu Asn Ala Ser Pro Leu Glu Gly Leu Tyr Ile Leu Glu Gly
        115                 120                 125

Leu Tyr Gly Leu Ser Glu Arg Ala Arg Gly Ile Leu Glu Ser Glu Arg
    130                 135                 140

His Ile Ser Gly Leu Ala Ser Asn Gly Leu Tyr Thr His Arg Ile Leu
145                 150                 155                 160

Glu Leu Glu Cys Tyr Ser Ser Glu Arg Leu Tyr Ser Gly Leu Tyr Ser
                165                 170                 175

Glu Arg Thr His Arg Cys Tyr Ser Thr Tyr Arg Gly Leu Tyr Leu Glu
            180                 185                 190

Thr Arg Pro Gly Leu Leu Tyr Ser Glu Arg Leu Tyr Ser Gly Leu
        195                 200                 205

Tyr Ala Ser Pro Ile Leu Glu Ala Ser Asn Leu Glu Val Ala Leu Leu
    210                 215                 220

Tyr Ser Gly Leu Asn Gly Leu Tyr Cys Tyr Ser Thr Arg Pro Ser Glu
225                 230                 235                 240

Arg His Ile Ser Ile Leu Glu Gly Leu Tyr Ala Ser Pro Pro Arg Gly
                245                 250                 255

Leu Asn Gly Leu Cys Tyr Ser His Ile Ser Thr Tyr Arg Gly Leu Gly
            260                 265                 270
```

-continued

```
Leu Cys Tyr Ser Val Ala Leu Val Ala Leu Thr His Arg Thr His Arg
            275                 280                 285

Thr His Arg Pro Arg Pro Arg Ser Glu Arg Ile Leu Glu Gly Leu Asn
        290                 295                 300

Ala Ser Asn Gly Leu Tyr Thr His Arg Thr Tyr Arg Ala Arg Gly Pro
305                 310                 315                 320

His Glu Cys Tyr Ser Cys Tyr Ser Cys Tyr Ser Ser Glu Arg Thr His
                325                 330                 335

Arg Ala Ser Pro Leu Glu Cys Tyr Ser Ala Ser Asn Val Ala Leu Ala
            340                 345                 350

Ser Asn Pro His Glu Thr His Arg Gly Leu Ala Ser Asn Pro His Glu
        355                 360                 365

Pro Arg Pro Arg Pro Arg Ala Ser Pro Thr His Arg Thr His Arg Pro
370                 375                 380

Arg Leu Glu Ser Glu Arg Pro Arg Pro Arg His Ile Ser Ser Glu Arg
385                 390                 395                 400

Pro His Glu Ala Ser Asn Ala Arg Gly Ala Ser Pro Gly Leu Thr His
                405                 410                 415

Arg Ile Leu Glu Ile Leu Glu Ile Leu Glu Ala Leu Ala Leu Glu Ala
            420                 425                 430

Leu Ala Ser Glu Arg Val Ala Leu Ser Glu Arg Val Ala Leu Leu Glu
            435                 440                 445

Ala Leu Ala Val Ala Leu Leu Glu Ile Leu Glu Val Ala Leu Ala Leu
450                 455                 460

Ala Leu Glu Cys Tyr Ser Pro His Glu Gly Leu Tyr Thr Tyr Arg Ala
465                 470                 475                 480

Arg Gly Met Glu Thr Leu Glu Thr His Arg Gly Leu Tyr Ala Ser Pro
                485                 490                 495

Ala Arg Gly Leu Tyr Ser Gly Leu Asn Gly Leu Tyr Leu Glu His Ile
            500                 505                 510

Ser Ser Glu Arg Met Glu Thr Ala Ser Asn Met Glu Thr Met Glu Thr
            515                 520                 525

Gly Leu Ala Leu Ala Ala Leu Ala Ala Leu Ala Ser Glu Arg Gly Leu
        530                 535                 540

Pro Arg Ser Glu Arg Leu Glu Ala Ser Pro Leu Glu Ala Ser Pro Ala
545                 550                 555                 560

Ser Asn Leu Glu Leu Tyr Ser Leu Glu Leu Glu Gly Leu Leu Glu Ile
                565                 570                 575

Leu Glu Gly Leu Tyr Ala Arg Gly Leu Tyr Ala Arg Gly Thr Tyr
            580                 585                 590

Arg Gly Leu Tyr Ala Leu Ala Val Ala Leu Thr Tyr Arg Leu Tyr Ser
        595                 600                 605

Gly Leu Tyr Ser Glu Arg Leu Glu Ala Ser Pro Gly Leu Ala Arg Gly
610                 615                 620

Pro Arg Val Ala Leu Ala Leu Ala Val Ala Leu Leu Tyr Ser Val Ala
625                 630                 635                 640

Leu Pro His Glu Ser Glu Arg Pro His Glu Ala Leu Ala Ala Ser Asn
                645                 650                 655

Ala Arg Gly Gly Leu Asn Ala Ser Asn Pro His Glu Ile Leu Glu Ala
            660                 665                 670

Ser Asn Gly Leu Leu Tyr Ser Ala Ser Asn Ile Leu Glu Thr Tyr Arg
            675                 680                 685

Ala Arg Gly Val Ala Leu Pro Arg Leu Glu Met Glu Thr Gly Leu His
```

-continued

```
            690                 695                 700
Ile Ser Ala Ser Pro Ala Ser Asn Ile Leu Glu Ala Leu Ala Ala Arg
705                 710                 715                 720
Gly Pro His Glu Ile Leu Glu Val Ala Leu Gly Leu Tyr Ala Ser Pro
                725                 730                 735
Gly Leu Ala Arg Gly Val Ala Leu Thr His Arg Ala Leu Ala Ala Ser
            740                 745                 750
Pro Gly Leu Tyr Ala Arg Gly Met Glu Thr Gly Leu Thr Tyr Arg Leu
            755                 760                 765
Glu Leu Glu Val Ala Leu Met Glu Thr Gly Leu Thr Tyr Arg Thr Tyr
770                 775                 780
Arg Pro Arg Ala Ser Asn Gly Leu Tyr Ser Glu Arg Leu Glu Cys Tyr
785                 790                 795                 800
Ser Leu Tyr Ser Thr Tyr Arg Leu Glu Ser Glu Arg Leu Glu His Ile
                805                 810                 815
Ser Thr His Arg Ser Glu Arg Ala Ser Pro Thr Arg Pro Val Ala Leu
            820                 825                 830
Ser Glu Arg Ser Glu Arg Cys Tyr Ser Ala Arg Gly Leu Glu Ala Leu
            835                 840                 845
Ala His Ile Ser Ser Glu Arg Val Ala Leu Thr His Arg Ala Arg Gly
850                 855                 860
Gly Leu Tyr Leu Glu Ala Leu Ala Thr Tyr Arg Leu Glu His Ile Ser
865                 870                 875                 880
Thr His Arg Gly Leu Leu Glu Pro Arg Ala Arg Gly Gly Leu Tyr Ala
                885                 890                 895
Ser Pro His Ile Ser Thr Tyr Arg Leu Tyr Ser Pro Arg Ala Leu Ala
                900                 905                 910
Ile Leu Glu Ser Glu Arg His Ile Ser Ala Arg Gly Ala Ser Pro Leu
            915                 920                 925
Glu Ala Ser Asn Ser Glu Arg Ala Arg Gly Ala Ser Asn Val Ala Leu
            930                 935                 940
Leu Glu Val Ala Leu Leu Tyr Ser Ala Ser Asn Ala Ser Pro Gly Leu
945                 950                 955                 960
Tyr Thr His Arg Cys Tyr Ser Val Ala Leu Ile Leu Glu Ser Glu Arg
                965                 970                 975
Ala Ser Pro Pro His Glu Gly Leu Tyr Leu Glu Ser Glu Arg Met Glu
                980                 985                 990
Thr Ala Arg Gly Leu Glu Thr His Arg Gly Leu Tyr Ala Ser Asn Ala
            995                 1000                1005
Arg Gly Leu Glu Val Ala Leu Ala Arg Gly Pro Arg Gly Leu Tyr Gly
            1010                1015                1020
Leu Gly Leu Ala Ser Pro Ala Ser Asn Ala Leu Ala Ala Leu Ala Ile
1025                1030                1035                1040
Leu Glu Ser Glu Arg Gly Leu Val Ala Leu Gly Leu Tyr Thr His Arg
                1045                1050                1055
Ile Leu Glu Ala Arg Gly Thr Tyr Arg Met Glu Thr Ala Leu Ala Pro
            1060                1065                1070
Arg Gly Leu Val Ala Leu Leu Glu Gly Leu Gly Leu Tyr Ala Leu Ala
            1075                1080                1085
Val Ala Leu Ala Ser Asn Leu Glu Ala Arg Gly Ala Ser Pro Cys Tyr
            1090                1095                1100
Ser Gly Leu Ser Glu Arg Ala Leu Ala Leu Glu Leu Tyr Ser Gly Leu
1105                1110                1115                1120
```

-continued

```
Asn Val Ala Leu Ala Ser Pro Met Glu Thr Thr Tyr Arg Ala Leu Ala
                1125                1130                1135
Leu Glu Gly Leu Tyr Leu Glu Ile Leu Glu Thr Tyr Arg Thr Arg Pro
            1140                1145                1150
Gly Leu Ile Leu Glu Pro His Glu Met Glu Thr Ala Arg Gly Cys Tyr
            1155                1160                1165
Ser Thr His Arg Ala Ser Pro Leu Glu Pro His Glu Pro Arg Gly Leu
        1170                1175                1180
Tyr Gly Leu Ser Glu Arg Val Ala Leu Pro Arg Gly Leu Thr Tyr Arg
1185                1190                1195                1200
Gly Leu Asn Met Glu Thr Ala Leu Ala Pro His Glu Gly Leu Asn Thr
                1205                1210                1215
His Arg Gly Leu Val Ala Leu Gly Leu Tyr Ala Ser Asn His Ile Ser
                1220                1225                1230
Pro Arg Thr His Arg Pro His Glu Gly Leu Ala Ser Pro Met Glu Thr
                1235                1240                1245
Gly Leu Asn Val Ala Leu Leu Glu Val Ala Leu Ser Glu Arg Ala Arg
            1250                1255                1260
Gly Gly Leu Leu Tyr Ser Gly Leu Asn Ala Arg Gly Pro Arg Leu Tyr
1265                1270                1275                1280
Ser Pro His Glu Pro Arg Gly Leu Ala Leu Ala Thr Arg Pro Leu Tyr
                1285                1290                1295
Ser Gly Leu Ala Ser Asn Ser Glu Arg Leu Glu Ala Leu Ala Val Ala
                1300                1305                1310
Leu Ala Arg Gly Ser Glu Arg Leu Glu Leu Tyr Ser Gly Leu Thr His
            1315                1320                1325
Arg Ile Leu Glu Gly Leu Ala Ser Pro Cys Tyr Ser Thr Arg Pro Ala
            1330                1335                1340
Ser Pro Gly Leu Asn Ala Ser Pro Ala Leu Ala Gly Leu Ala Leu Ala
1345                1350                1355                1360
Ala Arg Gly Leu Glu Thr His Arg Ala Leu Ala Gly Leu Asn Cys Tyr
                1365                1370                1375
Ser Ala Leu Ala Gly Leu Gly Leu Ala Arg Gly Met Glu Thr Ala Leu
            1380                1385                1390
Ala Gly Leu Leu Glu Met Glu Thr Met Glu Thr Ile Leu Glu Thr Arg
            1395                1400                1405
Pro Gly Leu Ala Arg Gly Ala Ser Asn Leu Tyr Ser Ser Glu Arg Val
            1410                1415                1420
Ala Leu Ser Glu Arg Pro Arg Thr His Arg Val Ala Leu Ala Ser Asn
1425                1430                1435                1440
Pro Arg Met Glu Thr Ser Glu Arg Thr His Arg Ala Leu Ala Met Glu
                1445                1450                1455
Thr Gly Leu Asn Ala Ser Asn Gly Leu Ala Arg Gly Ala Ser Asn Leu
                1460                1465                1470
Glu Ser Glu Arg His Ile Ser Ala Ser Asn Ala Arg Gly Ala Arg Gly
            1475                1480                1485
Val Ala Leu Pro Arg Leu Tyr Ser Ile Leu Glu Gly Leu Tyr Pro Arg
            1490                1495                1500
Thr Tyr Arg Pro Arg Ala Ser Pro Thr Tyr Arg Ser Glu Arg Ser Glu
1505                1510                1515                1520
Arg Ser Glu Arg Ser Glu Arg Thr Tyr Arg Ile Leu Glu Gly Leu Ala
                1525                1530                1535
```

```
Ser Pro Ser Glu Arg Ile Leu Glu His Ile Ser His Ile Ser Thr His
            1540                1545                1550

Arg Ala Ser Pro Ser Glu Arg Ile Leu Glu Val Ala Leu Leu Tyr Ser
            1555                1560                1565

Ala Ser Asn Ile Leu Glu Ser Glu Arg Ser Glu Arg Gly Leu His Ile
    1570                1575                1580

Ser Ser Glu Arg Met Glu Thr Ser Glu Arg Ser Glu Arg Thr His Arg
1585                1590                1595                1600

Pro Arg Leu Glu Thr His Arg Ile Leu Glu Gly Leu Tyr Gly Leu Leu
                1605                1610                1615

Tyr Ser (2) INFORMATION FOR SEQ ID NO:5:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTCTTGGCTG GCCCAGGGAT GACTTCCTCG CTGCAGCGGC CCTGGCGGGT GCCCTGGCTA        60

CCATGGACCA TCCTGCTGGT CAGCACTGCG GCTGCTTCGC AGAATCAAGA ACGGCTATGT       120

GCGTTTAAAG ATCCGTATCA GCAAGACCTT GGGATAGGTG AGAGTAGAAT CTCTCATGAA       180

AATGGGACAA TATTATGCTC GAAAGGTAGC ACCTGCTATG GCCTTTGGGA GAAATCAAAA       240

GGGGACATAA ATCTTGTAAA ACAAGGATGT TGGTCTCACA TTGGAGATCC CCAAGAGTGT       300

CACTATGAAG AATGTGTAGT AACTACCACT CCTCCCTCAA TTCAGAATGG AACATACCGT       360

TTCTGCTGTT GTAGCACAGA TTTATGTAAT GTCAACTTTA CTGAGAATTT TCCACCTCCT       420

GACACAACAC CACTCAGTCC ACCTCATTCA TTTAACCGAG ATGAGACATG A                471

(2) INFORMATION FOR SEQ ID NO:6:

(i) SEQUENCE CHARACTERISTICS:
        (A) LENGTH: 417 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:6:

Met Glu Thr Thr His Arg Ser Glu Arg Ser Glu Arg Leu Glu Gly Leu
1               5                   10                  15

Asn Ala Arg Gly Pro Arg Thr Arg Pro Ala Arg Gly Val Ala Leu Pro
                20                  25                  30

Arg Thr Arg Pro Leu Glu Pro Arg Thr Arg Pro Thr His Arg Ile Leu
            35                  40                  45

Glu Leu Glu Leu Glu Val Ala Leu Ser Glu Arg Thr His Arg Ala Leu
    50                  55                  60

Ala Ala Leu Ala Ala Leu Ala Ser Glu Arg Gly Leu Asn Ala Ser Asn
65                  70                  75                  80

Gly Leu Asn Gly Leu Ala Arg Gly Leu Glu Cys Tyr Ser Ala Leu Ala
                85                  90                  95

Pro His Glu Leu Tyr Ser Ala Ser Pro Pro Arg Thr Tyr Arg Gly Leu
                100                 105                 110
```

```
Asn Gly Leu Asn Ala Ser Pro Leu Glu Gly Leu Tyr Ile Leu Glu Gly
        115                 120                 125
Leu Tyr Gly Leu Ser Glu Arg Ala Arg Gly Ile Leu Glu Ser Glu Arg
        130                 135                 140
His Ile Ser Gly Leu Ala Ser Asn Gly Leu Tyr Thr His Arg Ile Leu
145                 150                 155                 160
Glu Leu Glu Cys Tyr Ser Ser Glu Arg Leu Tyr Ser Gly Leu Tyr Ser
                    165                 170                 175
Glu Arg Thr His Arg Cys Tyr Ser Thr Tyr Arg Gly Leu Tyr Leu Glu
                180                 185                 190
Thr Arg Pro Gly Leu Leu Tyr Ser Ser Glu Arg Leu Tyr Ser Gly Leu
                195                 200                 205
Tyr Ala Ser Pro Ile Leu Glu Ala Ser Asn Leu Glu Val Ala Leu Leu
        210                 215                 220
Tyr Ser Gly Leu Asn Gly Leu Tyr Cys Tyr Ser Thr Arg Pro Ser Glu
225                 230                 235                 240
Arg His Ile Ser Ile Leu Glu Gly Leu Tyr Ala Ser Pro Arg Gly
                    245                 250                 255
Leu Asn Gly Leu Cys Tyr Ser His Ile Ser Thr Tyr Arg Gly Leu Gly
                260                 265                 270
Leu Cys Tyr Ser Val Ala Leu Val Ala Leu Thr His Arg Thr His Arg
        275                 280                 285
Thr His Arg Pro Arg Pro Arg Ser Glu Arg Ile Leu Glu Gly Leu Asn
        290                 295                 300
Ala Ser Asn Gly Leu Tyr Thr His Arg Thr Tyr Arg Ala Arg Gly Pro
305                 310                 315                 320
His Glu Cys Tyr Ser Cys Tyr Ser Cys Tyr Ser Ser Glu Arg Thr His
                    325                 330                 335
Arg Ala Ser Pro Leu Glu Cys Tyr Ser Ala Ser Asn Val Ala Leu Ala
                340                 345                 350
Ser Asn Pro His Glu Thr His Arg Gly Leu Ala Ser Asn Pro His Glu
        355                 360                 365
Pro Arg Pro Arg Pro Arg Ala Ser Pro Thr His Arg Thr His Arg Pro
370                 375                 380
Arg Leu Glu Ser Glu Arg Pro Arg Pro Arg His Ile Ser Ser Glu Arg
385                 390                 395                 400
Pro His Glu Ala Ser Asn Ala Arg Gly Ala Ser Pro Gly Leu Thr His
                405                 410                 415
Arg (2) INFORMATION FOR SEQ ID NO:7:

(i) SEQUENCE CHARACTERISTICS:
        (A) LENGTH: 3508 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTTTGCTGGC CCAGGGATGA CTTCCTCGCT GCATCGGCCC TTTCGGGTGC CCTGGCTGCT        60

ATGGGCCGTC CTGCTGGTCA GCACTACGGC TGCTTCTCAG AATCAAGAAC GGCTGTGTGC       120

ATTTAAAGAT CCATATCAAC AAGATCTTGG GATAGGTGAG AGTCGAATCT CTCATGAAAA       180
```

-continued

```
TGGGACAATA TTATGTTCCA AAGGGAGCAC GTGTTATGGT CTGTGGGAGA AATCAAAAGG      240

GGACATCAAT CTTGTGAAAC AAGGATGTTG GTCTCACATC GGTGATCCCC AAGAGTGCCA      300

CTATGAAGAG TGTGTAGTAA CTACCACCCC ACCCTCAATT CAGAATGGAA CGTACCGCTT      360

TTGCTGCTGT AGTACAGATT TATGTAATGT CAACTTTACT GAGAACTTTC CACCCCCTGA      420

CACAACACCA CTCAGTCCAC CTCATTCATT AATCGAGAT GAAACGATAA TCATTGCTTT       480

GGCATCAGTT TCTGTGTTAG CTGTTTTGAT AGTCGCCTTA TGTTTTGGAT ACAGAATGTT      540

GACAGGAGAC CGGAAACAGG GTCTTCACAG CATGAACATG ATGGAGGCGG CAGCAGCAGA      600

GCCCTCCCTT GACCTGGATA ACCTGAAGCT GCTGGAGCTG ATTGGACGGG GTCGATACGG      660

AGCAGTATAT AAAGGTTCCT TGGATGAGCG TCCAGTTGCT GTAAAAGTAT TTTCTTTTGC      720

AAACCGTCAG AATTTTATAA ATGAAAAAAA CATTTACAGA GTGCCTTTGA TGGAACATGA      780

CAACATTGCT CGCTTCATAG TTGGAGACGA GAGGCTCACT GCAGACGGCC GCATGGAGTA      840

TTTGCTTGTG ATGGAGTATT ATCCCAATGG ATCTCTGTGC AAATATCTGA GTCTCCACAC      900

AAGTGATTGG GTAAGCTCTT GCCGTCTGGC TCATTCTGTG ACTAGAGGAC TGGCTTATCT      960

TCACACAGAA TTACCACGAG GAGATCATTA TAAACCCGCA ATCTCCCACC GAGATTTAAA     1020

CAGCAGGAAT GTCCTGGTAA AGAATGACGG CGCGTGTGTT ATCAGTGACT TTGGTTTATC     1080

CATGAGGCTA ACTGGAAATC GGCTGGTGCG CCCAGGGGAA GAAGATAATG CGGCTATAAG     1140

TGAGGTTGGC ACAATTCGCT ATATGGCACC AGAAGTGCTA AAGGAGCTG TGAACCTGAG      1200

GGACTGTGAG TCAGCTCTGA AGCAAGTGGA CATGTATGCG CTTGGACTCA TCTACTGGGA     1260

GGTGTTTATG AGGTGTACAG ACCTCTTCCC AGGTGAATCT GTACCAGATT ACCAGATGGC     1320

TTTTCAGACA GAAGTTGGAA ACCATCCCAC ATTTGAGGAT ATGCAGGTTC TTGTGTCCAG     1380

AGAGAAGCAG AGACCCAAGT TCCCAGAAGC CTGGAAAGAA AATAGCCTGG CAGTGAGGTC     1440

ACTCAAGGAA ACAATTGAAG ACTGCTGGGA CCAGGATGCA GAGGCTCGGC TCACTGCACA     1500

GTGTGCTGAG GAGAGGATGG CTGAACTCAT GATGATATGG GAGAGAAACA AGTCTGTGAG     1560

CCCAACGGTC AACCCAATGT CAACTGCTAT GCAGAATGAA CGCAACCTGT CACATAATAG     1620

GCGTGTGCCA AAAATCGGGC CTTACCCAGA TTATTCCTCT TCCTCATATA TTGAAGACTC     1680

TATCCATCAT ACTGACAGCA TTGTGAAGAA TATTTCCTCT GAGCATTCGA TGTCCAGCAC     1740

ACCATTGACA ATAGGAGAAA AGAATCGAAA TTCAATTAAT TATGAACGAC AGCAAGCACA     1800

AGCTCGAATC CCTAGCCCAG AAACAAGCGT CACAAGCCTG TCCACAAACA CAACCACCAC     1860

AAACACCACC GGCCTCACTC CAAGTACTGG CATGACCACT ATATCTGAGA TGCCATACCC     1920

AGATGAGACA CATTTGCACG CCACAAATGT TGCACAGTCA ATCGGGCCAA CCCCTGTCTG     1980

CTTACAGCTG ACAGAAGAAG ACTTGGAGAC TAATAAGCTA GATCCAAAAG AAGTTGATAA     2040

GAACCTCAAG GAAAGCTCTG ATGAGAATCT CATGGAGCAT TCTCTGAAGC AGTTCAGTGG     2100

GCCAGACCCA TTGAGCAGTA CCAGTTCTAG CTTGCTTTAT CCACTCATAA AGCTCGCAGT     2160

GGAAGTGACT GGACAACAGG ACTTCACACA GGCTGCAAAT GGGCAAGCAT GTTTAATTCC     2220

TGATGTTCCA CCTGCTCAGA TCTATCCTCT CCCTAAGCAA CAGAACCTTC CTAAGAGACC     2280

TACTAGTTTG CCTTTGAACA CCAAAAATTC AACAAAAGAA CCCCGGCTAA AATTTGGCAA     2340

CAAGCACAAA TCAAACTTGA AACAAGTAGA AACTGGAGTT GCCAAGATGA ATACAATCAA     2400

TGCAGCAGAG CCTCATGTGG TGACAGTAAC TATGAATGGT GTGGCAGGTA GAAGCCACAA     2460

TGTTAATTCT CATGCTGCCA CAACCCAGTA TGCCAATGGC GCAGTGCCAG CTGGCCAGGC     2520

AGCCAACATA GTGGCACATA GGTCCCAAGA AATGCTGCAG AATCAATTTA TTGGTGAGGA     2580
```

```
TACCAGGCTG AATATCAATT CCAGTCCTGA TGAGCATGAA CCTTTACTGA GACGAGAGCA    2640

ACAGGCTGGC CATGATGAAG GGGTTCTGGA TCGTTTGGTA GATAGGAGGG AACGGCCATT    2700

AGAAGGTGGC CGAACAAATT CCAATAACAA CAACAGCAAT CCATGTTCAG AACAAGATAT    2760

CCTTACACAA GGTGTTACAA GCACAGCTGC AGATCCTGGG CCATCAAAGC CCAGAAGAGC    2820

ACAGAGGCCC AATTCTCTGG ATCTTTCAGC CACAAATATC CTGGATGGCA GCAGTATACA    2880

GATAGGTGAG TCAACACAAG ATGGCAAATC AGGATCAGGT GAAAAGATCA AGAGACGTGT    2940

GAAAACTCCA TACTCTCTTA AGCGGTGGCG CCCGTCCACC TGGGTCATCT CCACCGAGCC    3000

GCTGGACTGT GAGGTCAACA ACAATGGCAG TGACAGGGCA GTCCATTCTA AATCTAGCAC    3060

TGCTGTGTAC CTTGCAGAGG GAGGCACTGC CACGACCACA GTGTCTAAAG ATATAGGAAT    3120

GAATTGTCTG TGAGATGTTT TCAAGCTTAT GGAGTGAAAT TATTTTTTTG CATCATTTAA    3180

ACATGCAGAA GACATTTAAA AAAAAAACTG CTTTAACCTC CTGTCAGCAC CCCTTCCCAC    3240

CCCTGCAGCA AGGACTTGCT TTAAATAGAT TTCAGCTATG CAGAAAATTT TAGCTTATGC    3300

TTCCATAATT TTTAATTTTG TTTTTTAAGT TTTGCACTTT TGTTTAGTCT TGCTAAAGTT    3360

ATATTTGTCT GTTATGACCA CATTATATGT GTGCTTATCC AAAGTGGTCT CCAAATATTT    3420

TTTTAAGAAA AAAGCCCAAA CAATGGATTG CTGATAATCA GTTTGGACCA TTTTCTAAAG    3480

GTCATTAAAA CAGAAGCAAA TTCAGACC                                      3508

(2) INFORMATION FOR SEQ ID NO:8:

(i) SEQUENCE CHARACTERISTICS:
        (A) LENGTH: 2887 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:8:

Met Glu Thr Thr His Arg Ser Glu Arg Ser Glu Arg Leu Glu His Ile
  1               5                  10                  15

Ser Ala Arg Gly Pro Arg Pro His Glu Ala Arg Gly Val Ala Leu Pro
                 20                  25                  30

Arg Thr Arg Pro Leu Glu Leu Glu Thr Arg Pro Ala Leu Ala Val Ala
             35                  40                  45

Leu Leu Glu Leu Glu Val Ala Leu Ser Glu Arg Thr His Arg Thr His
 50                  55                  60

Arg Ala Leu Ala Ala Leu Ala Ser Glu Arg Gly Leu Asn Ala Ser Asn
 65                  70                  75                  80

Gly Leu Asn Gly Leu Ala Arg Gly Leu Glu Cys Tyr Ser Ala Leu Ala
                 85                  90                  95

Pro His Glu Leu Tyr Ser Ala Ser Pro Pro Arg Thr Tyr Arg Gly Leu
                100                 105                 110

Asn Gly Leu Asn Ala Ser Pro Leu Glu Gly Leu Tyr Ile Leu Glu Gly
            115                 120                 125

Leu Tyr Gly Leu Ser Glu Arg Ala Arg Gly Ile Leu Glu Ser Glu Arg
        130                 135                 140

His Ile Ser Gly Leu Ala Ser Asn Gly Leu Tyr Thr His Arg Ile Leu
145                 150                 155                 160

Glu Leu Glu Cys Tyr Ser Ser Gly Arg Leu Tyr Ser Gly Leu Tyr Ser
                165                 170                 175
```

```
Glu Arg Thr His Arg Cys Tyr Ser Thr Tyr Arg Gly Leu Tyr Leu Glu
            180                 185                 190

Thr Arg Pro Gly Leu Leu Tyr Ser Ser Glu Arg Leu Tyr Ser Gly Leu
            195                 200                 205

Tyr Ala Ser Pro Ile Leu Glu Ala Ser Asn Leu Glu Val Ala Leu Leu
            210                 215                 220

Tyr Ser Gly Leu Asn Gly Leu Tyr Cys Tyr Ser Thr Arg Pro Ser Glu
225                 230                 235                 240

Arg His Ile Ser Ile Leu Glu Gly Leu Tyr Ala Ser Pro Arg Gly
            245                 250                 255

Leu Asn Gly Leu Cys Tyr Ser His Ile Ser Thr Tyr Arg Gly Leu Gly
            260                 265                 270

Leu Cys Tyr Ser Val Ala Leu Val Ala Leu Thr His Arg Thr His Arg
            275                 280                 285

Thr His Arg Pro Arg Pro Arg Ser Glu Arg Ile Leu Glu Gly Leu Asn
            290                 295                 300

Ala Ser Asn Gly Leu Tyr Thr His Arg Thr Tyr Arg Ala Arg Gly Pro
305                 310                 315                 320

His Glu Cys Tyr Ser Cys Tyr Ser Cys Tyr Ser Ser Glu Arg Thr His
                    325                 330                 335

Arg Ala Ser Pro Leu Glu Cys Tyr Ser Ala Ser Asn Val Ala Leu Ala
            340                 345                 350

Ser Asn Pro His Glu Thr His Arg Gly Leu Ala Ser Asn Pro His Glu
            355                 360                 365

Pro Arg Pro Arg Pro Arg Ala Ser Pro Thr His Arg Thr His Arg Pro
            370                 375                 380

Arg Leu Glu Ser Glu Arg Pro Arg Pro Arg His Ile Ser Ser Glu Arg
385                 390                 395                 400

Pro His Glu Ala Ser Asn Ala Arg Gly Ala Ser Pro Gly Leu Thr His
                    405                 410                 415

Arg Ile Leu Glu Ile Leu Glu Ile Leu Glu Ala Leu Ala Leu Glu Ala
            420                 425                 430

Leu Ala Ser Glu Arg Val Ala Leu Ser Glu Arg Val Ala Leu Leu Glu
            435                 440                 445

Ala Leu Ala Val Ala Leu Leu Glu Ile Leu Glu Val Ala Leu Ala Leu
            450                 455                 460

Ala Leu Glu Cys Tyr Ser Pro His Glu Gly Leu Tyr Thr Tyr Arg Ala
465                 470                 475                 480

Arg Gly Met Glu Thr Leu Glu Thr His Arg Gly Leu Tyr Ala Ser Pro
                    485                 490                 495

Ala Arg Gly Leu Tyr Ser Gly Leu Asn Gly Leu Tyr Leu Glu His Ile
            500                 505                 510

Ser Ser Glu Arg Met Glu Thr Ala Ser Asn Met Glu Thr Met Glu Thr
            515                 520                 525

Gly Leu Ala Leu Ala Ala Leu Ala Ala Leu Ala Ala Leu Ala Gly Leu
            530                 535                 540

Pro Arg Ser Glu Arg Leu Glu Ala Ser Pro Leu Glu Ala Ser Pro Ala
545                 550                 555                 560

Ser Asn Leu Glu Leu Tyr Ser Leu Glu Leu Gly Leu Leu Glu Ile
                    565                 570                 575

Leu Glu Gly Leu Tyr Ala Arg Gly Gly Leu Tyr Ala Arg Gly Thr Tyr
            580                 585                 590

Arg Gly Leu Tyr Ala Leu Ala Val Ala Leu Thr Tyr Arg Leu Tyr Ser
```

-continued

```
            595                 600                 605

Gly Leu Tyr Ser Glu Arg Leu Glu Ala Ser Pro Gly Leu Ala Arg Gly
            610                 615                 620

Pro Arg Val Ala Leu Ala Leu Ala Val Ala Leu Leu Tyr Ser Val Ala
625                 630                 635                 640

Leu Pro His Glu Ser Glu Arg Pro His Glu Ala Leu Ala Ala Ser Asn
                    645                 650                 655

Ala Arg Gly Gly Leu Asn Ala Ser Asn Pro His Glu Ile Leu Glu Ala
            660                 665                 670

Ser Asn Gly Leu Leu Tyr Ser Ala Ser Asn Ile Leu Glu Thr Tyr Arg
            675                 680                 685

Ala Arg Gly Val Ala Leu Pro Arg Leu Glu Met Glu Thr Gly Leu His
            690                 695                 700

Ile Ser Ala Ser Pro Ala Ser Asn Ile Leu Glu Ala Leu Ala Ala Arg
705                 710                 715                 720

Gly Pro His Glu Ile Leu Glu Val Ala Leu Gly Leu Tyr Ala Ser Pro
                    725                 730                 735

Gly Leu Ala Arg Gly Leu Glu Thr His Arg Ala Leu Ala Ala Ser Pro
            740                 745                 750

Gly Leu Tyr Ala Arg Gly Met Glu Thr Gly Leu Thr Tyr Arg Leu Glu
            755                 760                 765

Leu Glu Val Ala Leu Met Glu Thr Gly Leu Thr Tyr Arg Thr Tyr Arg
770                 775                 780

Pro Arg Ala Ser Asn Gly Leu Tyr Ser Glu Arg Leu Glu Cys Tyr Ser
785                 790                 795                 800

Leu Tyr Ser Thr Tyr Arg Leu Glu Ser Glu Arg Leu Glu His Ile Ser
                    805                 810                 815

Thr His Arg Ser Glu Arg Ala Ser Pro Thr Arg Pro Val Ala Leu Ser
            820                 825                 830

Glu Arg Ser Glu Arg Cys Tyr Ser Ala Arg Gly Leu Glu Ala Leu Ala
            835                 840                 845

His Ile Ser Ser Glu Arg Val Ala Leu Thr His Arg Ala Arg Gly Gly
            850                 855                 860

Leu Tyr Leu Glu Ala Leu Ala Thr Tyr Arg Leu Glu His Ile Ser Thr
865                 870                 875                 880

His Arg Gly Leu Leu Glu Pro Arg Ala Arg Gly Gly Leu Tyr Ala Ser
                    885                 890                 895

Pro His Ile Ser Thr Tyr Arg Leu Tyr Ser Pro Arg Ala Leu Ala Ile
                    900                 905                 910

Leu Glu Ser Glu Arg His Ile Ser Ala Arg Gly Ala Ser Pro Leu Glu
            915                 920                 925

Ala Ser Asn Ser Glu Arg Ala Arg Gly Ala Ser Asn Val Ala Leu Leu
930                 935                 940

Glu Val Ala Leu Leu Tyr Ser Ala Ser Asn Ala Ser Pro Gly Leu Tyr
945                 950                 955                 960

Ala Leu Ala Cys Tyr Ser Val Ala Leu Ile Leu Glu Ser Glu Arg Ala
                    965                 970                 975

Ser Pro Pro His Glu Gly Leu Tyr Leu Glu Ser Glu Arg Met Glu Thr
            980                 985                 990

Ala Arg Gly Leu Glu Thr His Arg Gly Leu Tyr Ala Ser Asn Ala Arg
            995                 1000                1005

Gly Leu Glu Val Ala Leu Ala Arg Gly Pro Arg Gly Leu Tyr Gly Leu
            1010                1015                1020
```

```
Gly Leu Ala Ser Pro Ala Ser Asn Ala Leu Ala Ala Leu Ala Ile Leu
1025                1030                1035                1040

Glu Ser Glu Arg Gly Leu Val Ala Leu Gly Leu Tyr Thr His Arg Ile
                1045                1050                1055

Leu Glu Ala Arg Gly Thr Tyr Arg Met Glu Thr Ala Leu Ala Pro Arg
                1060                1065                1070

Gly Leu Val Ala Leu Leu Glu Gly Leu Gly Leu Tyr Ala Leu Ala Val
                1075                1080                1085

Ala Leu Ala Ser Asn Leu Glu Ala Arg Gly Ala Ser Pro Cys Tyr Ser
                1090                1095                1100

Gly Leu Ser Glu Arg Ala Leu Ala Leu Glu Leu Tyr Ser Gly Leu Asn
1105                1110                1115                1120

Val Ala Leu Ala Ser Pro Met Glu Thr Thr Tyr Arg Ala Leu Ala Leu
                1125                1130                1135

Glu Gly Leu Tyr Leu Glu Ile Leu Glu Thr Tyr Arg Thr Arg Pro Gly
                1140                1145                1150

Leu Val Ala Leu Pro His Glu Met Glu Thr Ala Arg Gly Cys Tyr Ser
                1155                1160                1165

Thr His Arg Ala Ser Pro Leu Glu Pro His Glu Pro Arg Gly Leu Tyr
                1170                1175                1180

Gly Leu Ser Glu Arg Val Ala Leu Pro Arg Ala Ser Pro Thr Tyr Arg
1185                1190                1195                1200

Gly Leu Asn Met Glu Thr Ala Leu Ala Pro His Glu Gly Leu Asn Thr
                1205                1210                1215

His Arg Gly Leu Val Ala Leu Gly Leu Tyr Ala Ser Asn His Ile Ser
                1220                1225                1230

Pro Arg Thr His Arg Pro His Glu Gly Leu Ala Ser Pro Met Glu Thr
                1235                1240                1245

Gly Leu Asn Val Ala Leu Leu Glu Val Ala Leu Ser Glu Arg Ala Arg
                1250                1255                1260

Gly Gly Leu Leu Tyr Ser Gly Leu Asn Ala Arg Gly Pro Arg Leu Tyr
1265                1270                1275                1280

Ser Pro His Glu Pro Arg Gly Leu Ala Leu Ala Thr Arg Pro Leu Tyr
                1285                1290                1295

Ser Gly Leu Ala Ser Asn Ser Glu Arg Leu Glu Ala Leu Ala Val Ala
                1300                1305                1310

Leu Ala Arg Gly Ser Glu Arg Leu Glu Leu Tyr Ser Gly Leu Thr His
                1315                1320                1325

Arg Ile Leu Glu Gly Leu Ala Ser Pro Cys Tyr Ser Thr Arg Pro Ala
                1330                1335                1340

Ser Pro Gly Leu Asn Ala Ser Pro Ala Leu Ala Gly Leu Ala Leu Ala
1345                1350                1355                1360

Ala Arg Gly Leu Glu Thr His Arg Ala Leu Ala Gly Leu Asn Cys Tyr
                1365                1370                1375

Ser Ala Leu Ala Gly Leu Gly Leu Ala Arg Gly Met Glu Thr Ala Leu
                1380                1385                1390

Ala Gly Leu Leu Glu Met Glu Thr Met Glu Thr Ile Leu Glu Thr Arg
                1395                1400                1405

Pro Gly Leu Ala Arg Gly Ala Ser Asn Leu Tyr Ser Ser Glu Arg Val
                1410                1415                1420

Ala Leu Ser Glu Arg Pro Arg Thr His Arg Val Ala Leu Ala Ser Asn
1425                1430                1435                1440
```

-continued

```
Pro Arg Met Glu Thr Ser Glu Arg Thr His Arg Ala Leu Ala Met Glu
            1445                1450                1455

Thr Gly Leu Asn Ala Ser Asn Gly Leu Ala Arg Gly Ala Ser Asn Leu
            1460                1465                1470

Glu Ser Glu Arg His Ile Ser Ala Ser Asn Ala Arg Gly Ala Arg Gly
            1475                1480                1485

Val Ala Leu Pro Arg Leu Tyr Ser Ile Leu Glu Gly Leu Tyr Pro Arg
        1490                1495                1500

Thr Tyr Arg Pro Arg Ala Ser Pro Thr Tyr Arg Ser Glu Arg Ser Glu
1505                1510                1515                1520

Arg Ser Glu Arg Ser Glu Arg Thr Tyr Arg Ile Leu Glu Gly Leu Ala
            1525                1530                1535

Ser Pro Ser Glu Arg Ile Leu Glu His Ile Ser His Ile Ser Thr His
            1540                1545                1550

Arg Ala Ser Pro Ser Glu Arg Ile Leu Glu Val Ala Leu Leu Tyr Ser
            1555                1560                1565

Ala Ser Asn Ile Leu Glu Ser Glu Arg Ser Glu Arg Gly Leu His Ile
            1570                1575                1580

Ser Ser Glu Arg Met Glu Thr Ser Glu Arg Ser Glu Arg Thr His Arg
1585                1590                1595                1600

Pro Arg Leu Glu Thr His Arg Ile Leu Glu Gly Leu Tyr Gly Leu Leu
            1605                1610                1615

Tyr Ser Ala Ser Asn Ala Arg Gly Ala Ser Asn Ser Glu Arg Ile Leu
            1620                1625                1630

Glu Ala Ser Asn Thr Tyr Arg Gly Leu Ala Arg Gly Gly Leu Asn Gly
            1635                1640                1645

Leu Asn Ala Leu Ala Gly Leu Asn Ala Leu Ala Ala Arg Gly Ile Leu
            1650                1655                1660

Glu Pro Arg Ser Glu Arg Pro Arg Gly Leu Thr His Arg Ser Glu Arg
1665                1670                1675                1680

Val Ala Leu Thr His Arg Ser Glu Arg Leu Glu Ser Glu Arg Thr His
            1685                1690                1695

Arg Ala Ser Asn Thr His Arg Thr His Arg Thr His Arg Thr His Arg
            1700                1705                1710

Ala Ser Asn Thr His Arg Thr His Arg Gly Leu Tyr Leu Glu Thr His
            1715                1720                1725

Arg Pro Arg Ser Glu Arg Thr His Arg Gly Leu Tyr Met Glu Thr Thr
            1730                1735                1740

His Arg Thr His Arg Ile Leu Glu Ser Glu Arg Gly Leu Met Glu Thr
1745                1750                1755                1760

Pro Arg Thr Tyr Arg Pro Arg Ala Ser Pro Gly Leu Thr His Arg His
            1765                1770                1775

Ile Ser Leu Glu His Ile Ser Ala Leu Ala Thr His Arg Ala Ser Asn
            1780                1785                1790

Val Ala Leu Ala Leu Ala Gly Leu Asn Ser Glu Arg Ile Leu Glu Gly
            1795                1800                1805

Leu Tyr Pro Arg Thr His Arg Pro Arg Val Ala Leu Cys Tyr Ser Leu
            1810                1815                1820

Glu Gly Leu Asn Leu Glu Thr His Arg Gly Leu Gly Leu Ala Ser Pro
1825                1830                1835                1840

Leu Glu Gly Leu Thr His Arg Ala Ser Asn Leu Tyr Ser Leu Glu Ala
            1845                1850                1855

Ser Pro Pro Arg Leu Tyr Ser Gly Leu Val Ala Leu Ala Ser Pro Leu
```

```
                    1860           1865              1870
Tyr Ser Ala Ser Asn Leu Glu Leu Tyr Ser Gly Leu Ser Glu Arg Ser
            1875              1880              1885

Glu Arg Ala Ser Pro Gly Leu Ala Ser Asn Leu Glu Met Glu Thr Gly
            1890              1895              1900

Leu His Ile Ser Ser Glu Arg Leu Glu Leu Tyr Ser Gly Leu Asn Pro
1905              1910              1915              1920

His Glu Ser Glu Arg Gly Leu Tyr Pro Arg Ala Ser Pro Arg Leu
            1925              1930              1935

Glu Ser Glu Arg Ser Glu Arg Thr His Arg Ser Glu Arg Ser Glu Arg
            1940              1945              1950

Ser Glu Arg Leu Glu Leu Glu Thr Tyr Arg Pro Arg Leu Glu Ile Leu
            1955              1960              1965

Glu Leu Tyr Ser Leu Glu Ala Leu Ala Val Ala Leu Gly Leu Val Ala
            1970              1975              1980

Leu Thr His Arg Gly Leu Tyr Gly Leu Asn Gly Leu Asn Ala Ser Pro
1985              1990              1995              2000

Pro His Glu Thr His Arg Gly Leu Asn Ala Leu Ala Ala Leu Ala Ala
            2005              2010              2015

Ser Asn Gly Leu Tyr Gly Leu Asn Ala Leu Ala Cys Tyr Ser Leu Glu
            2020              2025              2030

Ile Leu Glu Pro Arg Ala Ser Pro Val Ala Leu Pro Arg Pro Arg Ala
            2035              2040              2045

Leu Ala Gly Leu Asn Ile Leu Glu Thr Tyr Arg Pro Arg Leu Glu Pro
            2050              2055              2060

Arg Leu Tyr Ser Gly Leu Asn Gly Leu Asn Ala Ser Asn Leu Glu Pro
2065              2070              2075              2080

Arg Leu Tyr Ser Ala Arg Gly Pro Arg Thr His Arg Ser Glu Arg Leu
            2085              2090              2095

Glu Pro Arg Leu Glu Ala Ser Asn Thr His Arg Leu Tyr Ser Ala Ser
            2100              2105              2110

Asn Ser Glu Arg Thr His Arg Leu Tyr Ser Gly Leu Pro Arg Ala Arg
            2115              2120              2125

Gly Leu Glu Leu Tyr Ser Pro His Glu Gly Leu Tyr Ala Ser Asn Leu
            2130              2135              2140

Tyr Ser His Ile Ser Leu Tyr Ser Ser Glu Arg Ala Ser Asn Leu Glu
2145              2150              2155              2160

Leu Tyr Ser Gly Leu Asn Val Ala Leu Gly Leu Thr His Arg Gly Leu
            2165              2170              2175

Tyr Val Ala Leu Ala Leu Ala Leu Tyr Ser Met Glu Thr Ala Ser Asn
            2180              2185              2190

Thr His Arg Ile Leu Glu Ala Ser Asn Ala Leu Ala Ala Leu Ala Gly
            2195              2200              2205

Leu Pro Arg His Ile Ser Val Ala Leu Val Ala Leu Thr His Arg Val
            2210              2215              2220

Ala Leu Thr His Arg Met Glu Thr Ala Ser Asn Gly Leu Tyr Val Ala
2225              2230              2235              2240

Leu Ala Leu Ala Gly Leu Tyr Ala Arg Gly Ser Glu Arg His Ile Ser
            2245              2250              2255

Ala Ser Asn Val Ala Leu Ala Ser Asn Ser Glu Arg His Ile Ser Ala
            2260              2265              2270

Leu Ala Ala Leu Ala Thr His Arg Thr His Arg Gly Leu Asn Thr Tyr
            2275              2280              2285
```

-continued

Arg Ala Leu Ala Ala Ser Asn Gly Leu Tyr Ala Leu Ala Val Ala Leu
        2290                2295                2300

Pro Arg Ala Leu Ala Gly Leu Tyr Gly Leu Asn Ala Leu Ala Ala Leu
2305                2310                2315                2320

Ala Ala Ser Asn Ile Leu Glu Val Ala Leu Ala Leu Ala His Ile Ser
            2325                2330                2335

Ala Arg Gly Ser Glu Arg Gly Leu Asn Gly Leu Met Glu Thr Leu Glu
        2340                2345                2350

Gly Leu Asn Ala Ser Asn Gly Leu Asn Pro His Glu Ile Leu Glu Gly
        2355                2360                2365

Leu Tyr Gly Leu Ala Ser Pro Thr His Arg Ala Arg Gly Leu Glu Ala
        2370                2375                2380

Ser Asn Ile Leu Glu Ala Ser Asn Ser Glu Arg Ser Glu Arg Pro Arg
2385                2390                2395                2400

Ala Ser Pro Gly Leu His Ile Ser Gly Leu Pro Arg Leu Glu Leu Glu
            2405                2410                2415

Ala Arg Gly Ala Arg Gly Gly Leu Gly Leu Asn Gly Leu Asn Ala Leu
        2420                2425                2430

Ala Gly Leu Tyr His Ile Ser Ala Ser Pro Gly Leu Gly Leu Tyr Val
        2435                2440                2445

Ala Leu Leu Glu Ala Ser Pro Ala Arg Gly Leu Glu Val Ala Leu Ala
        2450                2455                2460

Ser Pro Ala Arg Gly Ala Arg Gly Gly Leu Ala Arg Gly Pro Arg Leu
2465                2470                2475                2480

Glu Gly Leu Gly Leu Tyr Gly Leu Tyr Ala Arg Gly Thr His Arg Ala
            2485                2490                2495

Ser Asn Ser Glu Arg Ala Ser Asn Ala Ser Asn Ala Ser Asn Ala Ser
        2500                2505                2510

Asn Ser Glu Arg Ala Ser Asn Pro Arg Cys Tyr Ser Glu Arg Gly
        2515                2520                2525

Leu Gly Leu Asn Ala Ser Pro Ile Leu Glu Leu Glu Thr His Arg Gly
        2530                2535                2540

Leu Asn Gly Leu Tyr Val Ala Leu Thr His Arg Ser Glu Arg Thr His
2545                2550                2555                2560

Arg Ala Leu Ala Ala Leu Ala Ala Ser Pro Pro Arg Gly Leu Tyr Pro
            2565                2570                2575

Arg Ser Glu Arg Leu Tyr Ser Pro Arg Ala Arg Gly Ala Arg Gly Ala
        2580                2585                2590

Leu Ala Gly Leu Asn Ala Arg Gly Pro Arg Ala Ser Asn Ser Glu Arg
        2595                2600                2605

Leu Glu Ala Ser Pro Leu Glu Ser Glu Arg Ala Leu Ala Thr His Arg
        2610                2615                2620

Ala Ser Asn Ile Leu Glu Leu Glu Ala Ser Pro Gly Leu Tyr Ser Glu
2625                2630                2635                2640

Arg Ser Glu Arg Ile Leu Glu Gly Leu Asn Ile Leu Glu Gly Leu Tyr
            2645                2650                2655

Gly Leu Ser Glu Arg Thr His Arg Gly Leu Asn Ala Ser Pro Gly Leu
        2660                2665                2670

Tyr Leu Tyr Ser Ser Glu Arg Gly Leu Tyr Ser Glu Arg Gly Leu Tyr
        2675                2680                2685

Gly Leu Leu Tyr Ser Ile Leu Glu Leu Tyr Ser Ala Arg Gly Ala Arg
        2690                2695                2700

-continued

```
Gly Val Ala Leu Leu Tyr Ser Thr His Arg Pro Arg Thr Tyr Arg Ser
2705                2710                2715                2720

Glu Arg Leu Glu Leu Tyr Ser Ala Arg Gly Thr Arg Pro Ala Arg Gly
                2725                2730                2735

Pro Arg Ser Glu Arg Thr His Arg Thr Arg Pro Val Ala Leu Ile Leu
                2740                2745                2750

Glu Ser Glu Arg Thr His Arg Gly Leu Pro Arg Leu Glu Ala Ser Pro
            2755                2760                2765

Cys Tyr Ser Gly Leu Val Ala Leu Ala Ser Asn Ala Ser Asn Ala Ser
            2770                2775                2780

Asn Gly Leu Tyr Ser Glu Arg Ala Ser Pro Ala Arg Gly Ala Leu Ala
2785                2790                2795                2800

Val Ala Leu His Ile Ser Ser Glu Arg Leu Tyr Ser Ser Glu Arg Ser
                2805                2810                2815

Glu Arg Thr His Arg Ala Leu Ala Val Ala Leu Thr Tyr Arg Leu Glu
                2820                2825                2830

Ala Leu Ala Gly Leu Gly Leu Tyr Gly Leu Tyr Thr His Arg Ala Leu
                2835                2840                2845

Ala Thr His Arg Thr His Arg Thr His Arg Val Ala Leu Ser Glu Arg
            2850                2855                2860

Leu Tyr Ser Ala Ser Pro Ile Leu Glu Gly Leu Tyr Met Glu Thr Ala
2865                2870                2875                2880

Ser Asn Cys Tyr Ser Leu Glu
                2885
```

(2) INFORMATION FOR SEQ ID NO:9:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CTTTGCTGGC CCAGGGATGA CTTCCTCGCT GCATCGGCCC TTTCGGGTGC CCTGGCTGCT      60

ATGGGCCGTC CTGCTGGTCA GCACTACGGC TGCTTCTCAG AATCAAGAAC GGCTGTGTGC     120

ATTTAAAGAT CCATATCAAC AAGATCTTGG GATAGGTGAG AGTCGAATCT CTCATGAAAA     180

TGGGACAATA TTATGTTCCA AAGGGAGCAC GTGTTATGGT CTGTGGGAGA AATCAAAAGG     240

GGACATCAAT CTTGTGAAAC AAGGATGTTG GTCTCACATC GGTGATCCCC AAGAGTGCCA     300

CTATGAAGAG TGTGTAGTAA CTACCACCCC ACCCTCAATT CAGAATGGAA CGTACCGCTT     360

TTGCTGCTGT AGTACAGATT TATGTAATGT CAACTTTACT GAGAACTTTC CACCCCCTGA     420

CACAACACCA CTCAGTCCAC CTCATTCATT TAATCGAGAT GAAACGTGA                 469
```

(2) INFORMATION FOR SEQ ID NO:10:

(i) SEQUENCE CHARACTERISTICS:
        (A) LENGTH: 417 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:10:

Met Glu Thr Thr His Arg Ser Glu Arg Ser Glu Arg Leu Glu His Ile

```
1               5                   10                  15

Ser Ala Arg Gly Pro Arg Pro His Glu Ala Arg Gly Val Ala Leu Pro
                20              25              30

Arg Thr Arg Pro Leu Glu Leu Glu Thr Arg Pro Ala Leu Ala Val Ala
        35              40              45

Leu Leu Glu Leu Glu Val Ala Leu Ser Glu Arg Thr His Arg Thr His
    50              55              60

Arg Ala Leu Ala Ala Leu Ala Ser Glu Arg Gly Leu Asn Ala Ser Asn
65              70              75              80

Gly Leu Asn Gly Leu Ala Arg Gly Leu Glu Cys Tyr Ser Ala Leu Ala
                85              90              95

Pro His Glu Leu Tyr Ser Ala Ser Pro Pro Arg Thr Tyr Arg Gly Leu
            100             105             110

Asn Gly Leu Asn Ala Ser Pro Leu Glu Gly Leu Tyr Ile Leu Glu Gly
            115             120             125

Leu Tyr Gly Leu Ser Glu Arg Ala Arg Gly Ile Leu Glu Ser Glu Arg
    130             135             140

His Ile Ser Gly Leu Ala Ser Asn Gly Leu Tyr Thr His Arg Ile Leu
145             150             155             160

Glu Leu Glu Cys Tyr Ser Ser Glu Arg Leu Tyr Ser Gly Leu Tyr Ser
                165             170             175

Glu Arg Thr His Arg Cys Tyr Ser Thr Tyr Arg Gly Leu Tyr Leu Glu
            180             185             190

Thr Arg Pro Gly Leu Leu Tyr Ser Glu Arg Leu Tyr Ser Gly Leu
        195             200             205

Tyr Ala Ser Pro Ile Leu Glu Ala Ser Asn Leu Glu Val Ala Leu Leu
    210             215             220

Tyr Ser Gly Leu Asn Gly Leu Tyr Cys Tyr Ser Thr Arg Pro Ser Glu
225             230             235             240

Arg His Ile Ser Ile Leu Glu Gly Leu Tyr Ala Ser Pro Pro Arg Gly
                245             250             255

Leu Asn Gly Leu Cys Tyr Ser His Ile Ser Thr Tyr Arg Gly Leu Gly
                260             265             270

Leu Cys Tyr Ser Val Ala Leu Val Ala Leu Thr His Arg Thr His Arg
            275             280             285

Thr His Arg Pro Arg Pro Arg Ser Glu Arg Ile Leu Glu Gly Leu Asn
        290             295             300

Ala Ser Asn Gly Leu Tyr Thr His Arg Thr Tyr Arg Ala Arg Gly Pro
305             310             315             320

His Glu Cys Tyr Ser Cys Tyr Ser Cys Tyr Ser Ser Glu Arg Thr His
                325             330             335

Arg Ala Ser Pro Leu Glu Cys Tyr Ser Ala Ser Asn Val Ala Leu Ala
            340             345             350

Ser Asn Pro His Glu Thr His Arg Gly Leu Ala Ser Asn Pro His Glu
            355             360             365

Pro Arg Pro Arg Pro Arg Ala Ser Pro Thr His Arg Thr His Arg Pro
        370             375             380

Arg Leu Glu Ser Glu Arg Pro Arg Pro Arg His Ile Ser Ser Glu Arg
385             390             395             400

Pro His Glu Ala Ser Asn Ala Arg Gly Ala Ser Pro Gly Leu Thr His
            405             410             415

Arg
```

(2) INFORMATION FOR SEQ ID NO:11:

(i) SEQUENCE CHARACTERISTICS:
        (A) LENGTH: 2402 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GAATCAGACA ATGACTCAGC TATACACTTA CATCAGATTA CTGGGAGCCT GTCTGTTCAT      60

CATTTCTCAT GTTCAAGGGC AGAATCTAGA TAGTATGCTC CATGGCACTG GTATGAAATC     120

AGACTTGGAC CAGAAGAAGC CAGAAAATGG AGTGACTTTA GCACCAGAGG ATACCTTGCC     180

TTTCTTAAAG TGCTATTGCT CAGGACACTG CCCAGATGAT GCTATTAATA ACACATGCAT     240

AACTAATGGC CATTGCTTTG CCATTATAGA AGAAGATGAT CAGGGAGAAA CCACATTAAC     300

TTCTGGGTGT ATGAAGTATG AAGGCTCTGA TTTTCAATGC AAGGATTCAC CGAAAGCCCA     360

GCTACGCAGG ACAATAGAAT GTTGTCGGAC CAATTTGTGC AACCAGTATT TGCAGCCTAC     420

ACTGCCCCCT GTTGTTATAG GTCCGTTCTT TGATGGCAGC ATCCGATGGC TGGTTGTGCT     480

CATTTCCATG GCTGTCTGTA TAGTTGCTAT GATCATCTTC TCCAGCTGCT TTTGCTATAA     540

GCATTATTGT AAGAGTATCT CAAGCAGGGG TCGTTACAAC CGTGATTTGG AACAGGATGA     600

AGCATTTATT CCAGTAGGAG AATCATTGAA AGACCTGATT GACCAGTCCC AAAGCTCTGG     660

GAGTGGATCT GGATTGCCTT TATTGGTTCA GCGAACTATT GCCAAACAGA TTCAGATGGT     720

TCGGCAGGTT GGTAAAGGCC GCTATGGAGA AGTATGGATG GGTAAATGGC GTGGTGAAAA     780

AGTGGCTGTC AAAGTGTTTT TTACCACTGA AGAAGCTAGC TGGTTTAGAG AAACAGAAAT     840

CTACCAGACG TGTTAATGC GTCATGAAAA TATACTTGGT TTTATAGCTG CAGACATTAA     900

AGGCACTGGT TCCTGGACTC AGCTGTATTT GATTACTGAT TACCATGAAA ATGGATCTCT     960

CTATGACTTC CTGAAATGTG CCACACTAGA CACCAGAGCC CTACTCAAGT TAGCTTATTC    1020

TGCTGCTTGT GGTCTGTGCC ACCTCCACAC AGAAATTTAT GGTACCCAAG GGAAGCCTGC    1080

AATTGCTCAT CGAGACCTGA AGAGCAAAAA CATCCTTATT AAGAAAAATG GAAGTTGCTG    1140

TATTGCTGAC CTGGGCCTAG CTGTTAAATT CAACAGTGAT ACAAATGAAG TTGACATACC    1200

CTTGAATACC AGGGTGGGCA CCAAGCGGTA CATGGCTCCA GAAGTGCTGG ATGAAAGCCT    1260

GAATAAAAAC CATTTCCAGC CCTACATCAT GGCTGACATC TATAGCTTTG GTTTGATCAT    1320

TTGGGAAATG GCTCGTCGTT GTATTACAGG AGGAATCGTG GAGGAATATC AATTACCATA    1380

TTACAACATG GTGCCCAGTG ACCCATCCTA TGAGGACATG CGTGAGGTTG TGTGTGTGAA    1440

ACGCTTGCGG CCAATCGTGT CTAACCGCTG GAACAGCGAT GAATGTCTTC GAGCAGTTTT    1500

GAAGCTAATG TCAGAATGTT GGGCCCATAA TCCAGCCTCC AGACTCACAG CTTTGAGAAT    1560

CAAGAAGACA CTTGCAAAAA TGGTTGAATC CCAGGATGTA AAGATTTGAC AATTAAACAA    1620

TTTTGAGGGA GAATTTAGAC TGCAAGAACT TCTTCACCCA AGGAATGGGT GGGATTAGCA    1680

TGGAATAGGA TGTTGACTTG GTTTCCAGAC TCCTTCCTCT ACATCTTCAC AGGCTGCTAA    1740

CAGTAAACCT TACCGCACTC TACAGAATAC AAGATTGGAA CTTGGAACTT GGAACTTCAA    1800

ACATGTCATT CTTTATATAT GGACAGCTGT GTTTTAAATG TGGGGTTTTT GTGTTTTGCT    1860

TTCTTTGTTT TGTTTTGGTT TTGATGCTTT TTTGGTTTTT ATGAACTGCA TCAAGACTCC    1920

AATCCTGATA AGAAGTCTCT GGTCAACCTC TGGGTACTCA CTATCCTGTC CATAAAGTGG    1980
```

-continued

```
TGCTTTCTGT GAAAGCCTTA AGAAAATTAA TGAGCTCAGC AGAGATGGAA AAAGGCATAT    2040

TTGGCTTCTA CCAGAGAAAA CATCTGTCTG TGTTCTGTCT TTGTAAACAG CCTATAGATT    2100

ATGATCTCTT TGGGATACTG CCTGGCTTAT GATGGTGCAC CATACCTTTG ATATACATAC    2160

CAGAATTCTC TCCTGCCCTA GGGCTAAGAA GACAAGAATG TAGAGGTTGC ACAGGAGGTA    2220

TTTTGTGACC AGTGGTTTAA ATTGCAATAT CTAGTTGGCA ATCGCCAATT TCATAAAAGC    2280

CATCCACCTT GTAGCTGTAG TAACTTCTCC ACTGACTTTA TTTTTAGCAT AATAGTTGTG    2340

AAGGCCAAAC TCCATGTAAA GTGTCCATAG ACTTGGACTG TTTTCCCCCA GCTCTGATTA    2400

CC                                                                   2402
```

(2) INFORMATION FOR SEQ ID NO:12:

(i) SEQUENCE CHARACTERISTICS:
        (A) LENGTH: 1495 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:12:

```
Met Glu Thr Thr His Arg Gly Leu Asn Leu Glu Thr Tyr Arg Thr His
 1               5                  10                  15

Arg Thr Tyr Arg Ile Leu Glu Ala Arg Gly Leu Glu Leu Glu Gly Leu
                20                  25                  30

Tyr Ala Leu Ala Cys Tyr Ser Leu Glu Pro His Glu Ile Leu Glu Ile
            35                  40                  45

Leu Glu Ser Glu Arg His Ile Ser Val Ala Leu Gly Leu Asn Gly Leu
        50                  55                  60

Tyr Gly Leu Asn Ala Ser Asn Leu Glu Ala Ser Pro Ser Glu Arg Met
65                  70                  75                  80

Glu Thr Leu Glu His Ile Ser Gly Leu Tyr Thr His Arg Gly Leu Tyr
                85                  90                  95

Met Glu Thr Leu Tyr Ser Ser Glu Arg Ala Ser Pro Leu Glu Ala Ser
               100                 105                 110

Pro Gly Leu Asn Leu Tyr Ser Leu Tyr Ser Pro Arg Gly Leu Ala Ser
            115                 120                 125

Asn Gly Leu Tyr Val Ala Leu Thr His Arg Leu Glu Ala Leu Ala Pro
        130                 135                 140

Arg Gly Leu Ala Ser Pro Thr His Arg Leu Glu Pro Arg Pro His Glu
145                 150                 155                 160

Leu Glu Leu Tyr Ser Cys Tyr Ser Thr Tyr Arg Cys Tyr Ser Ser Glu
                165                 170                 175

Arg Gly Leu Tyr His Ile Ser Cys Tyr Ser Pro Arg Ala Ser Pro Ala
            180                 185                 190

Ser Pro Ala Leu Ala Ile Leu Glu Ala Ser Asn Ala Ser Asn Thr His
        195                 200                 205

Arg Cys Tyr Ser Ile Leu Glu Thr His Arg Ala Ser Asn Gly Leu Tyr
    210                 215                 220

His Ile Ser Cys Tyr Ser Pro His Glu Ala Leu Ala Ile Leu Glu Ile
225                 230                 235                 240

Leu Glu Gly Leu Gly Leu Ala Ser Pro Ala Ser Pro Gly Leu Asn Gly
                245                 250                 255

Leu Tyr Gly Leu Thr His Arg Thr His Arg Leu Glu Thr His Arg Ser
            260                 265                 270
```

-continued

```
Glu Arg Gly Leu Tyr Cys Tyr Ser Met Glu Thr Leu Tyr Ser Thr Tyr
        275                 280                 285

Arg Gly Leu Gly Leu Tyr Ser Glu Arg Ala Ser Pro Pro His Glu Gly
        290                 295                 300

Leu Asn Cys Tyr Ser Leu Tyr Ser Ala Ser Pro Ser Glu Arg Pro Arg
305                 310                 315                 320

Leu Tyr Ser Ala Leu Ala Gly Leu Asn Leu Glu Ala Arg Gly Ala Arg
                325                 330                 335

Gly Thr His Arg Ile Leu Glu Gly Leu Cys Tyr Ser Cys Tyr Ser Ala
                340                 345                 350

Arg Gly Thr His Arg Ala Ser Asn Leu Glu Cys Tyr Ser Ala Ser Asn
                355                 360                 365

Gly Leu Asn Thr Tyr Arg Leu Glu Gly Leu Asn Pro Arg Thr His Arg
        370                 375                 380

Leu Glu Pro Arg Pro Arg Val Ala Leu Val Ala Leu Ile Leu Glu Gly
385                 390                 395                 400

Leu Tyr Pro Arg Pro His Glu Pro His Glu Ala Ser Pro Gly Leu Tyr
                405                 410                 415

Ser Glu Arg Ile Leu Glu Ala Arg Gly Thr Arg Pro Leu Glu Val Ala
                420                 425                 430

Leu Val Ala Leu Leu Glu Ile Leu Glu Ser Glu Arg Met Glu Thr Ala
        435                 440                 445

Leu Ala Val Ala Leu Cys Tyr Ser Ile Leu Glu Val Ala Leu Ala Leu
        450                 455                 460

Ala Met Glu Thr Ile Leu Glu Ile Leu Glu Pro His Glu Ser Glu Arg
465                 470                 475                 480

Ser Glu Arg Cys Tyr Ser Pro His Glu Cys Tyr Ser Thr Tyr Arg Leu
                485                 490                 495

Tyr Ser His Ile Ser Thr Tyr Arg Cys Tyr Ser Leu Tyr Ser Ser Glu
                500                 505                 510

Arg Ile Leu Glu Ser Glu Arg Ser Glu Arg Ala Arg Gly Gly Leu Tyr
        515                 520                 525

Ala Arg Gly Thr Tyr Arg Ala Ser Asn Ala Arg Gly Ala Ser Pro Leu
        530                 535                 540

Glu Gly Leu Gly Leu Asn Ala Ser Pro Gly Leu Ala Leu Ala Pro His
545                 550                 555                 560

Glu Ile Leu Glu Pro Arg Val Ala Leu Gly Leu Tyr Gly Leu Ser Glu
                565                 570                 575

Arg Leu Glu Leu Tyr Ser Ala Ser Pro Leu Glu Ile Leu Glu Ala Ser
                580                 585                 590

Pro Gly Leu Asn Ser Glu Arg Gly Leu Asn Ser Glu Arg Ser Glu Arg
                595                 600                 605

Gly Leu Tyr Ser Glu Arg Gly Leu Tyr Ser Glu Arg Gly Leu Tyr Leu
        610                 615                 620

Glu Pro Arg Leu Glu Leu Glu Val Ala Leu Gly Leu Asn Ala Arg Gly
625                 630                 635                 640

Thr His Arg Ile Leu Glu Ala Leu Ala Leu Tyr Ser Gly Leu Asn Ile
                645                 650                 655

Leu Glu Gly Leu Asn Met Glu Thr Val Ala Leu Ala Arg Gly Gly Leu
                660                 665                 670

Asn Val Ala Leu Gly Leu Tyr Leu Tyr Ser Gly Leu Tyr Ala Arg Gly
        675                 680                 685
```

-continued

```
Thr Tyr Arg Gly Leu Tyr Gly Leu Val Ala Leu Thr Arg Pro Met Glu
    690                 695                 700

Thr Gly Leu Tyr Leu Tyr Ser Thr Arg Pro Ala Arg Gly Gly Leu Tyr
705                 710                 715                 720

Gly Leu Leu Tyr Ser Val Ala Leu Ala Leu Ala Val Ala Leu Leu Tyr
                725                 730                 735

Ser Val Ala Leu Pro His Glu Pro His Glu Thr His Arg Thr His Arg
            740                 745                 750

Gly Leu Gly Leu Ala Leu Ala Ser Glu Arg Thr Arg Pro Pro His Glu
            755                 760                 765

Ala Arg Gly Gly Leu Thr His Arg Gly Leu Ile Leu Glu Thr Tyr Arg
    770                 775                 780

Gly Leu Asn Thr His Arg Val Ala Leu Leu Glu Met Glu Thr Ala Arg
785                 790                 795                 800

Gly His Ile Ser Gly Leu Ala Ser Asn Ile Leu Glu Leu Glu Gly Leu
                805                 810                 815

Tyr Pro His Glu Ile Leu Glu Ala Leu Ala Ala Leu Ala Ala Ser Pro
            820                 825                 830

Ile Leu Glu Leu Tyr Ser Gly Leu Tyr Thr His Arg Gly Leu Tyr Ser
    835                 840                 845

Glu Arg Thr Arg Pro Thr His Arg Gly Leu Asn Leu Glu Thr Tyr Arg
    850                 855                 860

Leu Glu Ile Leu Glu Thr His Arg Ala Ser Pro Thr Tyr Arg His Ile
865                 870                 875                 880

Ser Gly Leu Ala Ser Asn Gly Leu Tyr Ser Glu Arg Leu Glu Thr Tyr
                885                 890                 895

Arg Ala Ser Pro Pro His Glu Leu Glu Leu Tyr Ser Cys Tyr Ser Ala
            900                 905                 910

Leu Ala Thr His Arg Leu Glu Ala Ser Pro Thr His Arg Ala Arg Gly
            915                 920                 925

Ala Leu Ala Leu Glu Leu Glu Leu Tyr Ser Leu Glu Ala Leu Ala Thr
    930                 935                 940

Tyr Arg Ser Glu Arg Ala Leu Ala Ala Leu Ala Cys Tyr Ser Gly Leu
945                 950                 955                 960

Tyr Leu Glu Cys Tyr Ser His Ile Ser Leu Glu His Ile Ser Thr His
                965                 970                 975

Arg Gly Leu Ile Leu Glu Thr Tyr Arg Gly Leu Tyr Thr His Arg Gly
            980                 985                 990

Leu Asn Gly Leu Tyr Leu Tyr Ser Pro Arg Ala Leu Ala Ile Leu Glu
            995                 1000                1005

Ala Leu Ala His Ile Ser Ala Arg Gly Ala Ser Pro Leu Glu Leu Tyr
    1010                1015                1020

Ser Ser Glu Arg Leu Tyr Ser Ala Ser Asn Ile Leu Glu Leu Glu Ile
1025                1030                1035                1040

Leu Glu Leu Tyr Ser Leu Tyr Ser Ala Ser Asn Gly Leu Tyr Ser Glu
                1045                1050                1055

Arg Cys Tyr Ser Cys Tyr Ser Ile Leu Glu Ala Leu Ala Ala Ser Pro
            1060                1065                1070

Leu Glu Gly Leu Tyr Leu Glu Ala Leu Ala Val Ala Leu Leu Tyr Ser
            1075                1080                1085

Pro His Glu Ala Ser Asn Ser Glu Arg Ala Ser Pro Thr His Arg Ala
    1090                1095                1100

Ser Asn Gly Leu Val Ala Leu Ala Ser Pro Ile Leu Glu Pro Arg Leu
```

```
                    1105                1110                1115                1120
Glu Ala Ser Asn Thr His Arg Ala Arg Gly Val Ala Leu Gly Leu Tyr
                1125                1130                1135
Thr His Arg Leu Tyr Ser Ala Arg Gly Thr Tyr Arg Met Glu Thr Ala
            1140                1145                1150
Leu Ala Pro Arg Gly Leu Val Ala Leu Leu Glu Ala Ser Pro Gly Leu
        1155                1160                1165
Ser Glu Arg Leu Glu Ala Ser Asn Leu Tyr Ser Ala Ser Asn His Ile
    1170                1175                1180
Ser Pro His Glu Gly Leu Asn Pro Arg Thr Tyr Arg Ile Leu Glu Met
1185                1190                1195                1200
Glu Thr Ala Leu Ala Ala Ser Pro Ile Leu Glu Thr Tyr Arg Ser Glu
                1205                1210                1215
Arg Pro His Glu Gly Leu Tyr Leu Glu Ile Leu Glu Ile Leu Glu Thr
                1220                1225                1230
Arg Pro Gly Leu Met Glu Thr Ala Leu Ala Ala Arg Gly Ala Arg Gly
                1235                1240                1245
Cys Tyr Ser Ile Leu Glu Thr His Arg Gly Leu Tyr Gly Leu Tyr Ile
                1250                1255                1260
Leu Glu Val Ala Leu Gly Leu Gly Leu Thr Tyr Arg Gly Leu Asn Leu
1265                1270                1275                1280
Glu Pro Arg Thr Tyr Arg Thr Tyr Arg Ala Ser Asn Met Glu Thr Val
                1285                1290                1295
Ala Leu Pro Arg Ser Glu Arg Ala Ser Pro Pro Arg Ser Glu Arg Thr
                1300                1305                1310
Tyr Arg Gly Leu Ala Ser Pro Met Glu Thr Ala Arg Gly Gly Leu Val
                1315                1320                1325
Ala Leu Val Ala Leu Cys Tyr Ser Val Ala Leu Leu Tyr Ser Ala Arg
                1330                1335                1340
Gly Leu Glu Ala Arg Gly Pro Arg Ile Leu Glu Val Ala Leu Ser Glu
1345                1350                1355                1360
Arg Ala Ser Asn Ala Arg Gly Thr Arg Pro Ala Ser Asn Ser Glu Arg
                1365                1370                1375
Ala Ser Pro Gly Leu Cys Tyr Ser Leu Glu Ala Arg Gly Ala Leu Ala
                1380                1385                1390
Val Ala Leu Leu Glu Leu Tyr Ser Leu Glu Met Glu Thr Ser Glu Arg
                1395                1400                1405
Gly Leu Cys Tyr Ser Thr Arg Pro Ala Leu Ala His Ile Ser Ala Ser
            1410                1415                1420
Asn Pro Arg Ala Leu Ala Ser Glu Arg Ala Arg Gly Leu Glu Thr His
1425                1430                1435                1440
Arg Ala Leu Ala Leu Glu Ala Arg Gly Ile Leu Glu Leu Tyr Ser Leu
                1445                1450                1455
Tyr Ser Thr His Arg Leu Glu Ala Leu Ala Leu Tyr Ser Met Glu Thr
            1460                1465                1470
Val Ala Leu Gly Leu Ser Glu Arg Gly Leu Asn Ala Ser Pro Val Ala
        1475                1480                1485
Leu Leu Tyr Ser Ile Leu Glu
    1490                1495

(2) INFORMATION FOR SEQ ID NO:13:

(i) SEQUENCE CHARACTERISTICS:
        (A) LENGTH: 2252 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GTTTTCCAGC AGACTGATGC TATAAATGCT CCACAACATG GAGAATGGTT TGGGTTGGAA      60
GTAGACTTAA AGACCATCTA TGTGTGGGGA TACCTCCCAC TAGATCAGGC TGCTCAGGGC     120
CCCATTCACC ACCTCCAGGG ACGGGGTAGC CACTGCTTCT CTGAGCAACC TGAGCAACTT     180
CCTCACAGTG AAGAGTTCCT CCTGTATCCG AGGGTGGAGT TCATTTCTTT TGTCCTTGGA     240
AGTTGAATAG CAGAAAGGGA CATTTCAGCT TTTCTTGATA AAGGTTACAT CCATTTTACT     300
TAGACTACAA GACGAAGATT TCTGAAAATT GAGATCTTTA GTTTTCTGGA CAAGATGCCC     360
TTGCTTAGCT CCAGCAAGTT GAGCATGGAG AGCAGAAAAG AAGATAGTGA GGGCACAGCA     420
CCTGCCCCTC CACAGAAGAA GCTGTCATGT CAGTGCCACC ACCATTGTCC TGAGGACTCA     480
GTCAACAGCA CCTGCAGCAC TGATGGCTAC TGCTTCACCA TAATAGAAGA AGATGATTCT     540
GGTGGACATT TGGTCACCAA AGGATGTCTA GGATTAGAGG GCTCGGACTT CCAGTGTCGG     600
GACACTCCTA TTCCACACCA AAGAAGATCT ATTGAATGCT GCACAGGCCA AGATTACTGT     660
AACAAACATC TTCACCCAAC GCTGCCACCA CTGAAAAATC GAGACTTTGC TGAAGGAAAC     720
ATTCACCATA AGGCCCTGCT GATCTCGGTG ACTGTCTGTA GTATACTACT GGTGCTTATC     780
ATCATATTCT GCTACTTCAG GTACAAGCGG CAAGAAGCCA GGCCCCGCTA CAGCATCGGG     840
CTGGAGCAGG ACGAGACCTA CATTCCCCCT GGAGAATCCC TGAAGGATCT GATCGAGCAG     900
TCCCAGAGCT CAGGCAGCGG CTCCGGGCTC CCTCTCCTGG TTCAAAGGAC CATAGCAAAA     960
CAGATTCAGA TGGTAAAACA GATTGGAAAA GGTCGCTATG GGGAAGTCTG GATGGGAAAG    1020
TGGCGTGGCG AAAAGGTAGC TGTCAAAGTG TTTTTTACCA CGGAGGAGGC CAGCTGGTTC    1080
AGAGAAACAG AAATCTACCA AACTGTCCTG ATGAGGCATG AAAATATTCT CGGATTCATT    1140
GCGGCAGACA TTAAAGGCAC AGGCTCTTGG ACCCAACTGT ATCTCATCAC TGACTATCAT    1200
GAGAATGGCT CCCTTTACGA TTACCTAAAA TCCACCACCC TGGACACAAA AGGCATGCTA    1260
AAATTGGCTT ACTCCTCTGT TAGTGGCTTG TGCCACCTAC ATACAGGGAT CTTCAGTACC    1320
CAAGGCAAAC CGGCTATTGC CCACCGTGAT CTAAAAAGTA AGAACATCCT GGTGAAAAAG    1380
AACGGAACCT GCTGTATAGC AGATTTGGGC TTGGCTGTTA AATTTATTAG TGATACAAAT    1440
GAGGTAGACA TCCCTCCAAA CACCCGCGTA GGAACAAAAC GCTATATGCC TCCTGAGGTG    1500
CTGGATGAAA GCTTGAACAG AAATCACTTT CAGTCGTACA TCATGGCTGA TATGTACAGC    1560
TTTGGACTCA TCCTTTGGGA GATAGCCAGG AGATGTGTGT CAGGAGGAAT AGTGGAAGAA    1620
TACCAGCTCC CATATCACGA CCTTGTCCCC AGTGACCCCT CCTACGAGGA CATGAGGGAG    1680
ATTGTGTGCA TCAAAAGGCT ACGTCCTTCA TTCCCCAACA GATGGAGCAG CGATGAGTGC    1740
CTGCGGCAGA TGGGGAAGCT CATGATGGAG TGCTGGGCCC ATAACCCTGC ATCCCGGCTC    1800
ACAGCCCTAC GAGTCAAAAA AACACTTGCC AAAATGTCAG AGTCGCAGGA CATTAAGCTC    1860
TGATGGAGCA AAAACAGCTC CTTCTCGTGA AGACCCATGG AAACAGACTT TCTCTTGCAG    1920
GCAGAAGTCA TGGAGAGGTG CTGATAAGTA CCCTGAGTGC AGTCATATTT AAGAGCAACT    1980
GTTTGTTTGA CAGCTTTGAG GAGACTGTTC TTGGCAAAAT CAGCTGAATT TTGGCATGCA    2040
AGGTTGGGAG AGGCTTATCT GCCCTTGTTT ACACAGGGAT ATACAGTTTT AGTAACTGGT    2100
TTAAGGTTAT GCATGTTGCT TTCCGTGAAA GCCACTTATT ATTTTATTAT TATTGTTATT    2160
```

```
ATTATTATTT TGATTGTTTT AAAAGATACT GCTTTAAATT TTATGAAAAT AAAACCCTTT      2220

GGTTAGAAGA AAAAAAGATG TATATTGTTA CA                                   2252
```

(2) INFORMATION FOR SEQ ID NO:14:

(i) SEQUENCE CHARACTERISTICS:
        (A) LENGTH: 1399 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:14:

```
Met Glu Thr Pro Arg Leu Glu Leu Glu Ser Glu Arg Ser Glu Arg Ser
  1               5                  10                  15

Glu Arg Leu Tyr Ser Leu Glu Ser Glu Arg Met Glu Thr Gly Leu Ser
             20                  25                  30

Glu Arg Ala Arg Gly Leu Tyr Ser Gly Leu Ala Ser Pro Ser Glu Arg
         35                  40                  45

Gly Leu Gly Leu Tyr Thr His Arg Ala Leu Ala Pro Arg Ala Leu Ala
 50                  55                  60

Pro Arg Pro Arg Gly Leu Asn Leu Tyr Ser Leu Tyr Ser Leu Glu Ser
 65                  70                  75                  80

Glu Arg Cys Tyr Ser Gly Leu Asn Cys Tyr Ser His Ile Ser His Ile
             85                  90                  95

Ser His Ile Ser Cys Tyr Ser Pro Arg Gly Leu Ala Ser Pro Ser Glu
            100                 105                 110

Arg Val Ala Leu Ala Ser Asn Ser Glu Arg Thr His Arg Cys Tyr Ser
            115                 120                 125

Ser Glu Arg Thr His Arg Ala Ser Pro Gly Leu Tyr Thr Tyr Arg Cys
        130                 135                 140

Tyr Ser Pro His Glu Thr His Arg Ile Leu Glu Ile Leu Glu Gly Leu
145                 150                 155                 160

Gly Leu Ala Ser Pro Ala Ser Pro Ser Glu Arg Gly Leu Tyr Gly Leu
                165                 170                 175

Tyr His Ile Ser Leu Glu Val Ala Leu Thr His Arg Leu Tyr Ser Gly
            180                 185                 190

Leu Tyr Cys Tyr Ser Leu Glu Gly Leu Tyr Leu Glu Gly Leu Gly Leu
        195                 200                 205

Tyr Ser Glu Arg Ala Ser Pro Pro His Glu Gly Leu Asn Cys Tyr Ser
210                 215                 220

Ala Arg Gly Ala Ser Pro Thr His Arg Pro Arg Ile Leu Glu Pro Arg
225                 230                 235                 240

His Ile Ser Gly Leu Asn Ala Arg Gly Ala Arg Gly Ser Glu Arg Ile
                245                 250                 255

Leu Glu Gly Leu Cys Tyr Ser Cys Tyr Ser Thr His Arg Gly Leu Tyr
            260                 265                 270

Gly Leu Asn Ala Ser Pro Thr Tyr Arg Cys Tyr Ser Ala Ser Asn Leu
        275                 280                 285

Tyr Ser His Ile Ser Leu Glu His Ile Ser Pro Arg Thr His Arg Leu
    290                 295                 300

Glu Pro Arg Pro Arg Leu Glu Leu Tyr Ser Ala Ser Asn Ala Arg Gly
305                 310                 315                 320

Ala Ser Pro Pro His Glu Ala Leu Ala Gly Leu Gly Leu Tyr Ala Ser
```

-continued

```
                    325                 330                 335
Asn Ile Leu Glu His Ile Ser His Ile Ser Leu Tyr Ser Ala Leu Ala
                340                 345                 350
Leu Glu Leu Glu Ile Leu Glu Ser Glu Arg Val Ala Leu Thr His Arg
                355                 360                 365
Val Ala Leu Cys Tyr Ser Ser Glu Arg Ile Leu Glu Leu Glu Leu Glu
370                 375                 380
Val Ala Leu Leu Glu Ile Leu Glu Ile Leu Glu Ile Leu Glu Pro His
385                 390                 395                 400
Glu Cys Tyr Ser Thr Tyr Arg Pro His Glu Ala Arg Gly Thr Tyr Arg
                405                 410                 415
Leu Tyr Ser Ala Arg Gly Gly Leu Asn Gly Leu Ala Leu Ala Ala Arg
                420                 425                 430
Gly Pro Arg Ala Arg Gly Thr Tyr Arg Ser Glu Arg Ile Leu Glu Gly
                435                 440                 445
Leu Tyr Leu Glu Gly Leu Gly Leu Asn Ala Ser Pro Gly Leu Thr His
                450                 455                 460
Arg Thr Tyr Arg Ile Leu Glu Pro Arg Pro Arg Gly Leu Tyr Gly Leu
465                 470                 475                 480
Ser Glu Arg Leu Glu Leu Tyr Ser Ala Ser Pro Leu Glu Ile Leu Glu
                485                 490                 495
Gly Leu Gly Leu Asn Ser Glu Arg Gly Leu Asn Ser Glu Arg Ser Glu
                500                 505                 510
Arg Gly Leu Tyr Ser Glu Arg Gly Leu Tyr Ser Glu Arg Gly Leu Tyr
                515                 520                 525
Leu Glu Pro Arg Leu Glu Leu Glu Val Ala Leu Gly Leu Asn Ala Arg
                530                 535                 540
Gly Thr His Arg Ile Leu Glu Ala Leu Ala Leu Tyr Ser Gly Leu Asn
545                 550                 555                 560
Ile Leu Glu Gly Leu Asn Met Glu Thr Val Ala Leu Leu Tyr Ser Gly
                565                 570                 575
Leu Asn Ile Leu Glu Gly Leu Tyr Leu Tyr Ser Gly Leu Tyr Ala Arg
                580                 585                 590
Gly Thr Tyr Arg Gly Leu Tyr Gly Leu Val Ala Leu Thr Arg Pro Met
                595                 600                 605
Glu Thr Gly Leu Tyr Leu Tyr Ser Thr Arg Pro Ala Arg Gly Gly Leu
                610                 615                 620
Tyr Gly Leu Leu Tyr Ser Val Ala Leu Ala Leu Ala Val Ala Leu Leu
625                 630                 635                 640
Tyr Ser Val Ala Leu Pro His Glu Pro His Glu Thr His Arg Thr His
                645                 650                 655
Arg Gly Leu Gly Leu Ala Leu Ala Ser Glu Arg Thr Arg Pro Pro His
                660                 665                 670
Glu Ala Arg Gly Gly Leu Thr His Arg Gly Leu Ile Leu Glu Thr Tyr
                675                 680                 685
Arg Gly Leu Asn Thr His Arg Val Ala Leu Leu Glu Met Glu Thr Ala
                690                 695                 700
Arg Gly His Ile Ser Gly Leu Ala Ser Asn Ile Leu Glu Leu Glu Gly
705                 710                 715                 720
Leu Tyr Pro His Glu Ile Leu Glu Ala Leu Ala Ala Leu Ala Ala Ser
                725                 730                 735
Pro Ile Leu Glu Leu Tyr Ser Gly Leu Tyr Thr His Arg Gly Leu Tyr
                740                 745                 750
```

-continued

```
Ser Glu Arg Thr Arg Pro Thr His Arg Gly Leu Asn Leu Glu Thr Tyr
            755                 760                 765
Arg Leu Glu Ile Leu Glu Thr His Arg Ala Ser Pro Thr Tyr Arg His
770                 775                 780
Ile Ser Gly Leu Ala Ser Asn Gly Leu Tyr Ser Glu Arg Leu Glu Thr
785                 790                 795                 800
Tyr Arg Ala Ser Pro Thr Tyr Arg Leu Glu Leu Tyr Ser Ser Glu Arg
                805                 810                 815
Thr His Arg Thr His Arg Leu Glu Ala Ser Pro Thr His Arg Leu Tyr
            820                 825                 830
Ser Gly Leu Tyr Met Glu Thr Leu Glu Leu Tyr Ser Leu Glu Ala Leu
            835                 840                 845
Ala Thr Tyr Arg Ser Glu Arg Ser Glu Arg Val Ala Leu Ser Glu Arg
850                 855                 860
Gly Leu Tyr Leu Glu Cys Tyr Ser His Ile Ser Leu Glu His Ile Ser
865                 870                 875                 880
Thr His Arg Gly Leu Tyr Ile Leu Glu Pro His Glu Ser Glu Arg Thr
            885                 890                 895
His Arg Gly Leu Asn Gly Leu Tyr Leu Tyr Ser Pro Arg Ala Leu Ala
            900                 905                 910
Ile Leu Glu Ala Leu Ala His Ile Ser Ala Arg Gly Ala Ser Pro Leu
            915                 920                 925
Glu Leu Tyr Ser Ser Glu Arg Leu Tyr Ser Ala Ser Asn Ile Leu Glu
            930                 935                 940
Leu Glu Val Ala Leu Leu Tyr Ser Leu Tyr Ser Ala Ser Asn Gly Leu
945                 950                 955                 960
Tyr Thr His Arg Cys Tyr Ser Cys Tyr Ser Ile Leu Glu Ala Leu Ala
                965                 970                 975
Ala Ser Pro Leu Glu Gly Leu Tyr Leu Glu Ala Leu Ala Val Ala Leu
                980                 985                 990
Leu Tyr Ser Pro His Glu Ile Leu Glu Ser Glu Arg Ala Ser Pro Thr
            995                 1000                1005
His Arg Ala Ser Asn Gly Leu Val Ala Leu Ala Ser Pro Ile Leu Glu
    1010                1015                1020
Pro Arg Pro Arg Ala Ser Asn Thr His Arg Ala Arg Gly Val Ala Leu
1025                1030                1035                1040
Gly Leu Tyr Thr His Arg Leu Tyr Ser Ala Arg Gly Thr Tyr Arg Met
                1045                1050                1055
Glu Thr Pro Arg Pro Arg Gly Leu Val Ala Leu Leu Glu Ala Ser Pro
            1060                1065                1070
Gly Leu Ser Glu Arg Leu Glu Ala Ser Asn Ala Arg Gly Ala Ser Asn
            1075                1080                1085
His Ile Ser Pro His Glu Gly Leu Asn Ser Glu Arg Thr Tyr Arg Ile
    1090                1095                1100
Leu Glu Met Glu Thr Ala Leu Ala Ala Ser Pro Met Glu Thr Thr Tyr
1105                1110                1115                1120
Arg Ser Glu Arg Pro His Glu Gly Leu Tyr Leu Glu Ile Leu Glu Leu
                1125                1130                1135
Glu Thr Arg Pro Gly Leu Ile Leu Glu Ala Leu Ala Ala Arg Gly Ala
            1140                1145                1150
Arg Gly Cys Tyr Ser Val Ala Leu Ser Glu Arg Gly Leu Tyr Gly Leu
            1155                1160                1165
```

```
Tyr Ile Leu Glu Val Ala Leu Gly Leu Gly Leu Thr Tyr Arg Gly Leu
    1170                1175                1180

Asn Leu Glu Pro Arg Thr Tyr Arg His Ile Ser Ala Ser Pro Leu Glu
1185                1190                1195                1200

Val Ala Leu Pro Arg Ser Glu Arg Ala Ser Pro Arg Ser Glu Arg
                1205                1210                1215

Thr Tyr Arg Gly Leu Ala Ser Pro Met Glu Thr Ala Arg Gly Gly Leu
                1220                1225                1230

Ile Leu Glu Val Ala Leu Cys Tyr Ser Ile Leu Glu Leu Tyr Ser Ala
                1235                1240                1245

Arg Gly Leu Glu Ala Arg Gly Pro Arg Ser Glu Arg Pro His Glu Pro
    1250                1255                1260

Arg Ala Ser Asn Ala Arg Gly Thr Arg Pro Ser Glu Arg Ser Glu Arg
1265                1270                1275                1280

Ala Ser Pro Gly Leu Cys Tyr Ser Leu Glu Ala Arg Gly Gly Leu Asn
                1285                1290                1295

Met Glu Thr Gly Leu Tyr Leu Tyr Ser Leu Glu Met Glu Thr Met Glu
                1300                1305                1310

Thr Gly Leu Cys Tyr Ser Thr Arg Pro Ala Leu Ala His Ile Ser Ala
        1315                1320                1325

Ser Asn Pro Arg Ala Leu Ala Ser Glu Arg Ala Arg Gly Leu Glu Thr
    1330                1335                1340

His Arg Ala Leu Ala Leu Glu Ala Arg Gly Val Ala Leu Leu Tyr Ser
1345                1350                1355                1360

Leu Tyr Ser Thr His Arg Leu Glu Ala Leu Ala Leu Tyr Ser Met Glu
                1365                1370                1375

Thr Ser Glu Arg Gly Leu Ser Glu Arg Gly Leu Asn Ala Ser Pro Ile
                1380                1385                1390

Leu Glu Leu Tyr Ser Leu Glu
        1395

(2) INFORMATION FOR SEQ ID NO:15:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GAATCAGACA ATGACTCAGC TATACACTTA CATCAGATTA CTGGGAGCCT GTCTGTTCAT      60

CATTTCTCAT GTTCAAGGGC AGAATCTAGA TAGTATGCTC CATGGCACTG GTATGAAATC     120

AGACTTGGAC CAGAAGAAGC CAGAAAATGG AGTGACTTTA GCACCAGAGG ATACCTTGCC     180

TTTCTTAAAG TGCTATTGCT CAGGACACTG CCCAGATGAT GCTATTAATA ACACATGCAT     240

AACTAATGGC CATTGCTTTG CCATTATAGA AGAAGATGAT CAGGGAGAAA CCACATTAAC     300

TTCTGGGTGT ATGAAGTATG AAGGCTCTGA TTTTCAATGC AAGGATTCAC CGAAAGCCCA     360

GCTACGCAGG ACAATAGAAT GTTGTCGGAC CAATTTGTGC AACCAGTATT TGCAGCCTAC     420

ACTGCCCCCT GTTGTTATAG GTCCGTTCTT TGATGGCAGC ATCCGATGA                 469

(2) INFORMATION FOR SEQ ID NO:16:

(i) SEQUENCE CHARACTERISTICS:
        (A) LENGTH: 425 amino acids
```

```
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:16:

Met Glu Thr Thr His Arg Gly Leu Asn Leu Glu Thr Tyr Arg Thr His
  1               5                  10                  15

Arg Thr Tyr Arg Ile Leu Glu Ala Arg Gly Leu Glu Leu Glu Gly Leu
             20                  25                  30

Tyr Ala Leu Ala Cys Tyr Ser Leu Glu Pro His Glu Ile Leu Glu Ile
             35                  40                  45

Leu Glu Ser Glu Arg His Ile Ser Val Ala Leu Gly Leu Asn Gly Leu
 50                  55                  60

Tyr Gly Leu Asn Ala Ser Asn Leu Glu Ala Ser Pro Ser Glu Arg Met
 65                  70                  75                  80

Glu Thr Leu Glu His Ile Ser Gly Leu Tyr Thr His Arg Gly Leu Tyr
                 85                  90                  95

Met Glu Thr Leu Tyr Ser Ser Glu Arg Ala Ser Pro Leu Glu Ala Ser
             100                 105                 110

Pro Gly Leu Asn Leu Tyr Ser Leu Tyr Ser Pro Arg Gly Leu Ala Ser
             115                 120                 125

Asn Gly Leu Tyr Val Ala Leu Thr His Arg Leu Glu Ala Leu Ala Pro
130                 135                 140

Arg Gly Leu Ala Ser Pro Thr His Arg Leu Glu Pro Arg Pro His Glu
145                 150                 155                 160

Leu Glu Leu Tyr Ser Cys Tyr Ser Thr Tyr Arg Cys Tyr Ser Ser Glu
                 165                 170                 175

Arg Gly Leu Tyr His Ile Ser Cys Tyr Ser Pro Arg Ala Ser Pro Ala
             180                 185                 190

Ser Pro Ala Leu Ala Ile Leu Glu Ala Ser Asn Ala Ser Asn Thr His
             195                 200                 205

Arg Cys Tyr Ser Ile Leu Glu Thr His Arg Ala Ser Asn Gly Leu Tyr
210                 215                 220

His Ile Ser Cys Tyr Ser Pro His Glu Ala Leu Ala Ile Leu Glu Ile
225                 230                 235                 240

Leu Glu Gly Leu Gly Leu Ala Ser Pro Ala Ser Pro Gly Leu Asn Gly
                 245                 250                 255

Leu Tyr Gly Leu Thr His Arg Thr His Arg Leu Glu Thr His Arg Ser
             260                 265                 270

Glu Arg Gly Leu Tyr Cys Tyr Ser Met Glu Thr Leu Tyr Ser Thr Tyr
             275                 280                 285

Arg Gly Leu Gly Leu Tyr Ser Glu Arg Ala Ser Pro His Glu Gly
290                 295                 300

Leu Asn Cys Tyr Ser Leu Tyr Ser Ala Ser Pro Ser Glu Arg Pro Arg
305                 310                 315                 320

Leu Tyr Ser Ala Leu Ala Gly Leu Asn Leu Glu Ala Arg Gly Ala Arg
                 325                 330                 335

Gly Thr His Arg Ile Leu Glu Gly Leu Cys Tyr Ser Cys Tyr Ser Ala
             340                 345                 350

Arg Gly Thr His Arg Ala Ser Asn Leu Glu Cys Tyr Ser Ala Ser Asn
             355                 360                 365

Gly Leu Asn Thr Tyr Arg Leu Glu Gly Leu Asn Pro Arg Thr His Arg
370                 375                 380
```

```
Leu Glu Pro Arg Pro Arg Val Ala Leu Val Ala Leu Ile Leu Glu Gly
385                 390                 395                 400

Leu Tyr Pro Arg Pro His Glu Pro His Glu Ala Ser Pro Gly Leu Tyr
            405                 410                 415

Ser Glu Arg Ile Leu Glu Ala Arg Gly
            420                 425
```

(2) INFORMATION FOR SEQ ID NO:17:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
TCTGGACAAG ATGCCCTTGC TTAGCTCCAG CAAGTTGAGC ATGGAGAGCA GAAAAGAAGA      60

TAGTGAGGGC ACAGCACCTG CCCCTCCACA GAAGAAGCTG TCATGTCAGT GCCACCACCA     120

TTGTCCTGAG GACTCAGTCA ACAGCACCTG CAGCACTGAT GGCTACTGCT TCACCATAAT     180

AGAAGAAGAT GATTCTGGTG ACATTTGGT CACCAAAGGA TGTCTAGGAT TAGAGGGCTC      240

GGACTTCCAG TGTCGGGACA CTCCTATTCC ACACCAAAGA AGATCTATTG AATGCTGCAC     300

AGGCCAAGAT TACTGTAACA AACATCTTCA CCCAACGCTG CCACCACTGA AAAATCGAGA     360

CTTTGCTGAA GGAAACATTC ACCATAAGTG A                                    391
```

(2) INFORMATION FOR SEQ ID NO:18:

(i) SEQUENCE CHARACTERISTICS:
        (A) LENGTH: 349 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:18:

```
Met Glu Thr Pro Arg Leu Glu Leu Glu Ser Glu Arg Ser Glu Arg Ser
1               5                   10                  15

Glu Arg Leu Tyr Ser Leu Glu Ser Glu Arg Met Glu Thr Gly Leu Ser
            20                  25                  30

Glu Arg Ala Arg Gly Leu Tyr Ser Gly Leu Ala Ser Pro Ser Glu Arg
            35                  40                  45

Gly Leu Gly Leu Tyr Thr His Arg Ala Leu Ala Pro Arg Ala Leu Ala
    50                  55                  60

Pro Arg Pro Arg Gly Leu Asn Leu Tyr Ser Leu Tyr Ser Leu Glu Ser
65                  70                  75                  80

Glu Arg Cys Tyr Ser Gly Leu Asn Cys Tyr Ser His Ile Ser His Ile
            85                  90                  95

Ser His Ile Ser Cys Tyr Ser Pro Arg Gly Leu Ala Ser Pro Ser Glu
            100                 105                 110

Arg Val Ala Leu Ala Ser Asn Ser Glu Arg Thr His Arg Cys Tyr Ser
            115                 120                 125

Ser Glu Arg Thr His Arg Ala Ser Pro Gly Leu Tyr Thr Tyr Arg Cys
            130                 135                 140

Tyr Ser Pro His Glu Thr His Arg Ile Leu Glu Ile Leu Glu Gly Leu
145                 150                 155                 160
```

```
Gly Leu Ala Ser Pro Ala Ser Pro Ser Glu Arg Gly Leu Tyr Gly Leu
                165                 170                 175

Tyr His Ile Ser Leu Glu Val Ala Leu Thr His Arg Leu Tyr Ser Gly
            180                 185                 190

Leu Tyr Cys Tyr Ser Leu Glu Gly Leu Tyr Leu Glu Gly Leu Gly Leu
        195                 200                 205

Tyr Ser Glu Arg Ala Ser Pro Pro His Glu Gly Leu Asn Cys Tyr Ser
    210                 215                 220

Ala Arg Gly Ala Ser Pro Thr His Arg Pro Arg Ile Leu Glu Pro Arg
225                 230                 235                 240

His Ile Ser Gly Leu Asn Ala Arg Gly Ala Arg Gly Ser Glu Arg Ile
                245                 250                 255

Leu Glu Gly Leu Cys Tyr Ser Cys Tyr Ser Thr His Arg Gly Leu Tyr
                260                 265                 270

Gly Leu Asn Ala Ser Pro Thr Tyr Arg Cys Tyr Ser Ala Ser Asn Leu
                275                 280                 285

Tyr Ser His Ile Ser Leu Glu His Ile Ser Pro Arg Thr His Arg Leu
            290                 295                 300

Glu Pro Arg Pro Arg Leu Glu Leu Tyr Ser Ala Ser Asn Ala Arg Gly
305                 310                 315                 320

Ala Ser Pro Pro His Glu Ala Leu Ala Gly Leu Gly Leu Tyr Ala Ser
                325                 330                 335

Asn Ile Leu Glu His Ile Ser His Ile Ser Leu Tyr Ser
                340                 345

(2) INFORMATION FOR SEQ ID NO:19:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GAATCAGACA ATGACTCAGC TATACACTTA CATCAGATTA CTGGGAGCCT GTCTGTTCAT      60

CATTTCTCAT GTTCAAGGGC AGAATCTAGA TAGTATGCTC CATGGCACTG GTATGAAATC     120

AGACTTGGAC CAGAAGAAGC CAGAAAATGG AGTGACTTTA GCACCAGAGG ATACCTTGCC     180

TTTCTTAAAG TGCTATTGCT CAGGACACTG CCCAGATGAT GCTATTAATA ACACATGCAT     240

AACTAATGGC CATTGCTTTG CCATTATAGA AGAAGATGAT CAGGGAGAAA CCACATTAAC     300

TTCTGGGTGT ATGAAGTATG AAGGCTCTGA TTTTCAATGC AAGGATTCAC CGAAAGCCCA     360

GCTACGCAGG ACAATAGAAT GTTGTCGGAC CAATTTGTGC AACCAGTATT TGCAGCCTAC     420

ACTGCCCCCT GTTGTTATAG GTCCGTTCTT TGATGGCAGC ATCCGATGGC TGGTTGTGCT     480

CATTTCCATG GCTGTCTGTA TAGTTGCTAT GATCATCTTC TCCAGCTGCT TTGCTATAA      540

GCATTATTGT AAGAGTATCT CAAGCAGGGG TCGTTACAAC CGTGATTTGG AACAGGATGA     600

AGCATTTATT CCAGTAGGAG AATCATTGAA AGACCTGATT GACCAGTCCC AAAGCTCTGG     660

GAGTGGATCT GGATTGCCTT TATTGGTTCA GCGAACTATT GCCTGA                   706

(2) INFORMATION FOR SEQ ID NO:20:

(i) SEQUENCE CHARACTERISTICS:
        (A) LENGTH: 649 amino acids
```

```
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:20:

Met Glu Thr Thr His Arg Gly Leu Asn Leu Glu Thr Tyr Arg Thr His
  1               5                  10                  15

Arg Thr Tyr Arg Ile Leu Glu Ala Arg Gly Leu Glu Leu Glu Gly Leu
             20                  25                  30

Tyr Ala Leu Ala Cys Tyr Ser Leu Glu Pro His Glu Ile Leu Glu Ile
             35                  40                  45

Leu Glu Ser Glu Arg His Ile Ser Val Ala Leu Gly Leu Asn Gly Leu
 50                  55                  60

Tyr Gly Leu Asn Ala Ser Asn Leu Glu Ala Ser Pro Ser Glu Arg Met
 65                  70                  75                  80

Glu Thr Leu Glu His Ile Ser Gly Leu Tyr Thr His Arg Gly Leu Tyr
                 85                  90                  95

Met Glu Thr Leu Tyr Ser Ser Glu Arg Ala Ser Pro Leu Glu Ala Ser
            100                 105                 110

Pro Gly Leu Asn Leu Tyr Ser Leu Tyr Ser Pro Arg Gly Leu Ala Ser
            115                 120                 125

Asn Gly Leu Tyr Val Ala Leu Thr His Arg Leu Glu Ala Leu Ala Pro
130                 135                 140

Arg Gly Leu Ala Ser Pro Thr His Arg Leu Glu Pro Arg Pro His Glu
145                 150                 155                 160

Leu Glu Leu Tyr Ser Cys Tyr Ser Thr Tyr Arg Cys Tyr Ser Ser Glu
                165                 170                 175

Arg Gly Leu Tyr His Ile Ser Cys Tyr Ser Pro Arg Ala Ser Pro Ala
                180                 185                 190

Ser Pro Ala Leu Ala Ile Leu Glu Ala Ser Asn Ala Ser Asn Thr His
            195                 200                 205

Arg Cys Tyr Ser Ile Leu Glu Thr His Arg Ala Ser Asn Gly Leu Tyr
210                 215                 220

His Ile Ser Cys Tyr Ser Pro His Glu Ala Leu Ala Ile Leu Glu Ile
225                 230                 235                 240

Leu Glu Gly Leu Gly Leu Ala Ser Pro Ala Ser Pro Gly Leu Asn Gly
                245                 250                 255

Leu Tyr Gly Leu Thr His Arg Thr His Arg Leu Glu Thr His Arg Ser
                260                 265                 270

Glu Arg Gly Leu Tyr Cys Tyr Ser Met Glu Thr Leu Tyr Ser Thr Tyr
            275                 280                 285

Arg Gly Leu Gly Leu Tyr Ser Glu Arg Ala Ser Pro Pro His Glu Gly
290                 295                 300

Leu Asn Cys Tyr Ser Leu Tyr Ser Ala Ser Pro Ser Glu Arg Pro Arg
305                 310                 315                 320

Leu Tyr Ser Ala Leu Ala Gly Leu Asn Leu Glu Ala Arg Gly Ala Arg
                325                 330                 335

Gly Thr His Arg Ile Leu Glu Gly Leu Cys Tyr Ser Cys Tyr Ser Ala
            340                 345                 350

Arg Gly Thr His Arg Ala Ser Asn Leu Glu Cys Tyr Ser Ala Ser Asn
            355                 360                 365

Gly Leu Asn Thr Tyr Arg Leu Glu Gly Leu Asn Pro Arg Thr His Arg
370                 375                 380
```

```
Leu Glu Pro Arg Pro Arg Val Ala Leu Val Ala Leu Ile Leu Glu Gly
385                 390                 395                 400

Leu Tyr Pro Arg Pro His Glu Pro His Glu Ala Ser Pro Gly Leu Tyr
            405                 410                 415

Ser Glu Arg Ile Leu Glu Ala Arg Gly Thr Arg Pro Leu Glu Val Ala
            420                 425             430

Leu Val Ala Leu Leu Glu Ile Leu Glu Ser Glu Arg Met Glu Thr Ala
        435             440                 445

Leu Ala Val Ala Leu Cys Tyr Ser Ile Leu Glu Val Ala Leu Ala Leu
    450                 455                 460

Ala Met Glu Thr Ile Leu Glu Ile Leu Glu Pro His Glu Ser Glu Arg
465                 470                 475                 480

Ser Glu Arg Cys Tyr Ser Pro His Glu Cys Tyr Ser Thr Tyr Arg Leu
            485                 490                 495

Tyr Ser His Ile Ser Thr Tyr Arg Cys Tyr Ser Leu Tyr Ser Ser Glu
                500                 505                 510

Arg Ile Leu Glu Ser Glu Arg Ser Glu Arg Ala Arg Gly Gly Leu Tyr
            515                 520                 525

Ala Arg Gly Thr Tyr Arg Ala Ser Asn Ala Arg Gly Ala Ser Pro Leu
530                 535                 540

Glu Gly Leu Gly Leu Asn Ala Ser Pro Gly Leu Ala Leu Ala Pro His
545                 550                 555                 560

Glu Ile Leu Glu Pro Arg Val Ala Leu Gly Leu Tyr Gly Leu Ser Glu
                565                 570                 575

Arg Leu Glu Leu Tyr Ser Ala Ser Pro Leu Glu Ile Leu Glu Ala Ser
            580                 585                 590

Pro Gly Leu Asn Ser Glu Arg Gly Leu Asn Ser Glu Arg Ser Glu Arg
            595                 600                 605

Gly Leu Tyr Ser Glu Arg Gly Leu Tyr Ser Glu Arg Gly Leu Tyr Leu
            610                 615                 620

Glu Pro Arg Leu Glu Leu Glu Val Ala Leu Gly Leu Asn Ala Arg Gly
625                 630                 635                 640

Thr His Arg Ile Leu Glu Ala Leu Ala
                645
```

(2) INFORMATION FOR SEQ ID NO:21:

(i) SEQUENCE CHARACTERISTICS:
        (A) LENGTH: 616 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
TCTGGACAAG ATGCCCTTGC TTAGCTCCAG CAAGTTGAGC ATGGAGAGCA GAAAAGAAGA      60

TAGTGAGGGC ACAGCACCTG CCCCTCCACA GAAGAAGCTG TCATGTCAGT GCCACCACCA     120

TTGTCCTGAG GACTCAGTCA ACAGCACCTG CAGCACTGAT GGCTACTGCT TCACCATAAT     180

AGAAGAAGAT GATTCTGGTG GACATTTGGT CACCAAAGGA TGTCTAGGAT TAGAGGGCTC     240

GGACTTCCAG TGTCGGGACA CTCCTATTCC ACACCAAAGA AGATCTATTG AATGCTGCAC     300

AGGCCAAGAT TACTGTAACA AACATCTTCA CCCAACGCTG CCACCACTGA AAAATCGAGA     360

CTTTGCTGAA GGAAACATTC ACCATAAGGC CCTGCTGATC TCGGTGACTG TCTGTAGTAT     420
```

-continued

```
ACTACTGGTG CTTATCATCA TATTCTGCTA CTTCAGGTAC AAGCGGCAAG AAGCCAGGCC      480

CCGCTACAGC ATCGGGCTGG AGCAGGACGA GACCTACATT CCCCCTGGAG AATCCCTGAA      540

GGATCTGATC GAGCAGTCCC AGAGCTCAGG CAGCGGCTCC GGGCTCCCTC TCCTGGTTCA      600

AAGGACCATA GCATGA                                                      616
```

(2) INFORMATION FOR SEQ ID NO:22:

(i) SEQUENCE CHARACTERISTICS:
        (A) LENGTH: 554 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:22:

```
Met Glu Thr Pro Arg Leu Glu Leu Glu Ser Glu Arg Ser Glu Arg Ser
1               5                   10                  15

Glu Arg Leu Tyr Ser Leu Glu Ser Glu Arg Met Glu Thr Gly Leu Ser
            20                  25                  30

Glu Arg Ala Arg Gly Leu Tyr Ser Gly Leu Ala Ser Pro Ser Glu Arg
        35                  40                  45

Gly Leu Gly Leu Tyr Thr His Arg Ala Leu Ala Pro Arg Ala Leu Ala
    50                  55                  60

Pro Arg Pro Arg Gly Leu Asn Leu Tyr Ser Leu Tyr Ser Leu Glu Ser
65                  70                  75                  80

Glu Arg Cys Tyr Ser Gly Leu Asn Cys Tyr Ser His Ile Ser His Ile
                85                  90                  95

Ser His Ile Ser Cys Tyr Ser Pro Arg Gly Leu Ala Ser Pro Ser Glu
            100                 105                 110

Arg Val Ala Leu Ala Ser Asn Ser Glu Arg Thr His Arg Cys Tyr Ser
        115                 120                 125

Ser Glu Arg Thr His Arg Ala Ser Pro Gly Leu Tyr Thr Tyr Arg Cys
    130                 135                 140

Tyr Ser Pro His Glu Thr His Arg Ile Leu Glu Ile Leu Glu Gly Leu
145                 150                 155                 160

Gly Leu Ala Ser Pro Ala Ser Pro Ser Glu Arg Gly Leu Tyr Gly Leu
                165                 170                 175

Tyr His Ile Ser Leu Glu Val Ala Leu Thr His Arg Leu Tyr Ser Gly
            180                 185                 190

Leu Tyr Cys Tyr Ser Leu Glu Gly Leu Tyr Leu Glu Gly Leu Gly Leu
        195                 200                 205

Tyr Ser Glu Arg Ala Ser Pro Pro His Glu Gly Leu Asn Cys Tyr Ser
    210                 215                 220

Ala Arg Gly Ala Ser Pro Thr His Arg Pro Arg Ile Leu Glu Pro Arg
225                 230                 235                 240

His Ile Ser Gly Leu Asn Ala Arg Gly Ala Arg Gly Ser Glu Arg Ile
                245                 250                 255

Leu Glu Gly Leu Cys Tyr Ser Cys Tyr Ser Thr His Arg Gly Leu Tyr
            260                 265                 270

Gly Leu Asn Ala Ser Pro Thr Tyr Arg Cys Tyr Ser Ala Ser Asn Leu
        275                 280                 285

Tyr Ser His Ile Ser Leu Glu His Ile Ser Pro Arg Thr His Arg Leu
    290                 295                 300

Glu Pro Arg Pro Arg Leu Glu Leu Tyr Ser Ala Ser Asn Ala Arg Gly
```

```
                305                 310                 315                 320
Ala Ser Pro Pro His Glu Ala Leu Ala Gly Leu Gly Leu Tyr Ala Ser
                    325                 330                 335

Asn Ile Leu Glu His Ile Ser His Ile Ser Leu Tyr Ser Ala Leu Ala
                340                 345                 350

Leu Glu Leu Glu Ile Leu Glu Ser Glu Arg Val Ala Leu Thr His Arg
            355                 360                 365

Val Ala Leu Cys Tyr Ser Ser Glu Arg Ile Leu Glu Leu Glu Leu Glu
        370                 375                 380

Val Ala Leu Leu Glu Ile Leu Glu Ile Leu Glu Ile Leu Glu Pro His
385                 390                 395                 400

Glu Cys Tyr Ser Thr Tyr Arg Pro His Glu Ala Arg Gly Thr Tyr Arg
                405                 410                 415

Leu Tyr Ser Ala Arg Gly Gly Leu Asn Gly Leu Ala Leu Ala Ala Arg
            420                 425                 430

Gly Pro Arg Ala Arg Gly Thr Tyr Arg Ser Glu Arg Ile Leu Glu Gly
        435                 440                 445

Leu Tyr Leu Glu Gly Leu Gly Leu Asn Ala Ser Pro Gly Leu Thr His
    450                 455                 460

Arg Thr Tyr Arg Ile Leu Glu Pro Arg Pro Arg Gly Leu Tyr Gly Leu
465                 470                 475                 480

Ser Glu Arg Leu Glu Leu Tyr Ser Ala Ser Pro Leu Glu Ile Leu Glu
                485                 490                 495

Gly Leu Gly Leu Asn Ser Glu Arg Gly Leu Asn Ser Glu Arg Ser Glu
                500                 505                 510

Arg Gly Leu Tyr Ser Glu Arg Gly Leu Tyr Ser Glu Arg Gly Leu Tyr
            515                 520                 525

Leu Glu Pro Arg Leu Glu Leu Glu Val Ala Leu Gly Leu Asn Ala Arg
        530                 535                 540

Gly Thr His Arg Ile Leu Glu Ala Leu Ala
545                 550
```

(2) INFORMATION FOR SEQ ID NO:23:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
TGGCCCAGGG ATGACTTCCT CGCTGCAGCG GCCCTGGCGG GTGCCCTGGC TACCATGGAC     60

CATCCTGCTG GTCAGCACTG CGGCTGCTTC GCAGAATCAA GAACGGCTAT GTGCGTTTAA    120

AGATCCGTAT CAGCAAGACC TTGGGATAGG TGAGAGTAGA ATCTCTCATG AAAATGGGAC    180

AATATTATGC TCGAAAGGTA GCACCTGCTA TGGCCTTTGG GAGAAATCAA AAGGGGACAT    240

AAATCTTGTA AAACAAGGAT GTTGGTCTCA CATTGGAGAT CCCCAAGAGT GTCACTATGA    300

AGAATGTGTA GTAACTACCA CTCCTCCCTC AATTCAGAAT GGAACATACC GTTTCTGCTG    360

TTGTAGCACA GATTATGTA ATGTCAACTT TACTGAGAAT TTTCCACCTC CTGACACAAC     420

ACCACTCAGT CCACCTCATT CATTTAACCG AGATGAGACA ATAATCATTG CTTTGGCATC    480

AGTCTCTGTA TTAGCTGTTT TGATAGTTGC CTTATGCTTT GGATACAGAA TGTTGACAGG    540

AGACCGTAAA CAAGGTCTTC ACAGTATGAA CATGATGGAG GCAGCAGCAT CCGAACCCTC    600
```

```
TCTTGATCTA TGA                                                613
```

(2) INFORMATION FOR SEQ ID NO:24:

(i) SEQUENCE CHARACTERISTICS:
        (A) LENGTH: 556 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:24:

```
Met Glu Thr Thr His Arg Ser Glu Arg Ser Glu Arg Leu Gly Leu
1               5                   10                  15

Asn Ala Arg Gly Pro Arg Thr Arg Pro Ala Arg Gly Val Ala Leu Pro
                20                  25                  30

Arg Thr Arg Pro Leu Glu Pro Arg Thr Arg Pro Thr His Arg Ile Leu
            35                  40                  45

Glu Leu Glu Leu Glu Val Ala Leu Ser Glu Arg Thr His Arg Ala Leu
        50                  55                  60

Ala Ala Leu Ala Ala Leu Ala Ser Glu Arg Gly Leu Asn Ala Ser Asn
65                  70                  75                  80

Gly Leu Asn Gly Leu Ala Arg Gly Leu Glu Cys Tyr Ser Ala Leu Ala
                85                  90                  95

Pro His Glu Leu Tyr Ser Ala Ser Pro Pro Arg Thr Tyr Arg Gly Leu
            100                 105                 110

Asn Gly Leu Asn Ala Ser Pro Leu Glu Gly Leu Tyr Ile Leu Glu Gly
        115                 120                 125

Leu Tyr Gly Leu Ser Glu Arg Ala Arg Gly Ile Leu Glu Ser Glu Arg
130                 135                 140

His Ile Ser Gly Leu Ala Ser Asn Gly Leu Tyr Thr His Arg Ile Leu
145                 150                 155                 160

Glu Leu Glu Cys Tyr Ser Ser Glu Arg Leu Tyr Ser Gly Leu Tyr Ser
                165                 170                 175

Glu Arg Thr His Arg Cys Tyr Ser Thr Tyr Arg Gly Leu Tyr Leu Glu
            180                 185                 190

Thr Arg Pro Gly Leu Leu Tyr Ser Ser Glu Arg Leu Tyr Ser Gly Leu
        195                 200                 205

Tyr Ala Ser Pro Ile Leu Glu Ala Ser Asn Leu Glu Val Ala Leu Leu
        210                 215                 220

Tyr Ser Gly Leu Asn Gly Leu Tyr Cys Tyr Ser Thr Arg Pro Ser Glu
225                 230                 235                 240

Arg His Ile Ser Ile Leu Glu Gly Leu Tyr Ala Ser Pro Pro Arg Gly
                245                 250                 255

Leu Asn Gly Leu Cys Tyr Ser His Ile Ser Thr Tyr Arg Gly Leu Gly
            260                 265                 270

Leu Cys Tyr Ser Val Ala Leu Val Ala Leu Thr His Arg Thr His Arg
        275                 280                 285

Thr His Arg Pro Arg Pro Arg Ser Glu Arg Ile Leu Glu Gly Leu Asn
        290                 295                 300

Ala Ser Asn Gly Leu Tyr Thr His Arg Thr Tyr Arg Ala Arg Gly Pro
305                 310                 315                 320

His Glu Cys Tyr Ser Cys Tyr Ser Cys Tyr Ser Ser Glu Arg Thr His
                325                 330                 335
```

```
Arg Ala Ser Pro Leu Glu Cys Tyr Ser Ala Ser Asn Val Ala Leu Ala
            340                 345                 350

Ser Asn Pro His Glu Thr His Arg Gly Leu Ala Ser Asn Pro His Glu
            355                 360                 365

Pro Arg Pro Arg Pro Arg Ala Ser Pro Thr His Arg Thr His Arg Pro
            370                 375                 380

Arg Leu Glu Ser Glu Arg Pro Arg Pro Arg His Ile Ser Ser Glu Arg
385                 390                 395                 400

Pro His Glu Ala Ser Asn Ala Arg Gly Ala Ser Pro Gly Leu Thr His
                405                 410                 415

Arg Ile Leu Glu Ile Leu Glu Ile Leu Glu Ala Leu Ala Leu Glu Ala
            420                 425                 430

Leu Ala Ser Glu Arg Val Ala Leu Ser Glu Arg Val Ala Leu Leu Glu
            435                 440                 445

Ala Leu Ala Val Ala Leu Leu Glu Ile Leu Glu Val Ala Leu Ala Leu
450                 455                 460

Ala Leu Glu Cys Tyr Ser Pro His Glu Gly Leu Tyr Thr Tyr Arg Ala
465                 470                 475                 480

Arg Gly Met Glu Thr Leu Glu Thr His Arg Gly Leu Tyr Ala Ser Pro
            485                 490                 495

Ala Arg Gly Leu Tyr Ser Gly Leu Asn Gly Leu Tyr Leu Glu His Ile
            500                 505                 510

Ser Ser Glu Arg Met Glu Thr Ala Ser Asn Met Glu Thr Met Glu Thr
            515                 520                 525

Gly Leu Ala Leu Ala Ala Leu Ala Ala Leu Ala Ser Glu Arg Gly Leu
            530                 535                 540

Pro Arg Ser Glu Arg Leu Glu Ala Ser Pro Leu Glu
545                 550                 555

(2) INFORMATION FOR SEQ ID NO:25:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGGCCCAGGG ATGACTTCCT CGCTGCATCG GCCCTTTCGG GTGCCCTGGC TGCTATGGGC      60

CGTCCTGCTG GTCAGCACTA CGGCTGCTTC TCAGAATCAA GAACGGCTGT GTGCATTTAA    120

AGATCCATAT CAACAAGATC TTGGGATAGG TGAGAGTCGA ATCTCTCATG AAAATGGGAC    180

AATATTATGT TCCAAAGGGA GCACGTGTTA TGGTCTGTGG GAGAAATCAA AAGGGGACAT    240

CAATCTTGTG AAACAAGGAT GTTGGTCTCA CATCGGTGAT CCCCAAGAGT GCCACTATGA    300

AGAGTGTGTA GTAACTACCA CCCCACCCTC AATTCAGAAT GGAACGTACC GCTTTTGCTG    360

CTGTAGTACA GATTTATGTA ATGTCAACTT TACTGAGAAC TTTCCACCCC CTGACACAAC    420

ACCACTCAGT CCACCTCATT CATTTAATCG AGATGAAACG ATAATCATTG CTTTGGCATC    480

AGTTTCTGTG TTAGCTGTTT TGATAGTCGC CTTATGTTTT GGATACAGAA TGTTGACAGG    540

AGACCGGAAA CAGGGTCTTC ACAGCATGAA CATGATGGAG GCGGCAGCAG CAGAGCCCTC    600

CCTTGACCTG TGA                                                      613

(2) INFORMATION FOR SEQ ID NO:26:
```

(i) SEQUENCE CHARACTERISTICS:
    (A) LENGTH: 556 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:26:

```
Met Glu Thr Thr His Arg Ser Glu Arg Ser Glu Arg Leu Glu His Ile
1               5                   10                  15

Ser Ala Arg Gly Pro Arg Pro His Glu Ala Arg Gly Val Ala Leu Pro
            20                  25                  30

Arg Thr Arg Pro Leu Glu Leu Glu Thr Arg Pro Ala Leu Ala Val Ala
        35                  40                  45

Leu Leu Glu Leu Glu Val Ala Leu Ser Glu Arg Thr His Arg Thr His
    50                  55                  60

Arg Ala Leu Ala Ala Leu Ala Ser Glu Arg Gly Leu Asn Ala Ser Asn
65                  70                  75                  80

Gly Leu Asn Gly Leu Ala Arg Gly Leu Glu Cys Tyr Ser Ala Leu Ala
                85                  90                  95

Pro His Glu Leu Tyr Ser Ala Ser Pro Pro Arg Thr Tyr Arg Gly Leu
            100                 105                 110

Asn Gly Leu Asn Ala Ser Pro Leu Glu Gly Leu Tyr Ile Leu Glu Gly
        115                 120                 125

Leu Tyr Gly Leu Ser Glu Arg Ala Arg Gly Ile Leu Glu Ser Glu Arg
    130                 135                 140

His Ile Ser Gly Leu Ala Ser Asn Gly Leu Tyr Thr His Arg Ile Leu
145                 150                 155                 160

Glu Leu Glu Cys Tyr Ser Ser Glu Arg Leu Tyr Ser Gly Leu Tyr Ser
                165                 170                 175

Glu Arg Thr His Arg Cys Tyr Ser Thr Tyr Arg Gly Leu Tyr Leu Glu
            180                 185                 190

Thr Arg Pro Gly Leu Leu Tyr Ser Ser Glu Arg Leu Tyr Ser Gly Leu
        195                 200                 205

Tyr Ala Ser Pro Ile Leu Glu Ala Ser Asn Leu Glu Val Ala Leu Leu
210                 215                 220

Tyr Ser Gly Leu Asn Gly Leu Tyr Cys Tyr Ser Thr Arg Pro Ser Glu
225                 230                 235                 240

Arg His Ile Ser Ile Leu Glu Gly Leu Tyr Ala Ser Pro Arg Gly
                245                 250                 255

Leu Asn Gly Leu Cys Tyr Ser His Ile Ser Thr Tyr Arg Gly Leu Gly
            260                 265                 270

Leu Cys Tyr Ser Val Ala Leu Val Ala Leu Thr His Arg Thr His Arg
        275                 280                 285

Thr His Arg Pro Arg Pro Arg Ser Glu Arg Ile Leu Glu Gly Leu Asn
    290                 295                 300

Ala Ser Asn Gly Leu Tyr Thr His Arg Thr Tyr Arg Ala Arg Gly Pro
305                 310                 315                 320

His Glu Cys Tyr Ser Cys Tyr Ser Cys Tyr Ser Ser Glu Arg Thr His
                325                 330                 335

Arg Ala Ser Pro Leu Glu Cys Tyr Ser Ala Ser Asn Val Ala Leu Ala
            340                 345                 350

Ser Asn Pro His Glu Thr His Arg Gly Leu Ala Ser Asn Pro His Glu
        355                 360                 365
```

```
Pro Arg Pro Arg Pro Arg Ala Ser Pro Thr His Arg Thr His Arg Pro
    370                 375                 380
Arg Leu Glu Ser Glu Arg Pro Arg Pro Arg His Ile Ser Ser Glu Arg
385                 390                 395                 400
Pro His Glu Ala Ser Asn Ala Arg Gly Ala Ser Pro Gly Leu Thr His
                405                 410                 415
Arg Ile Leu Glu Ile Leu Glu Ile Leu Glu Ala Leu Ala Leu Glu Ala
                420                 425                 430
Leu Ala Ser Glu Arg Val Ala Leu Ser Glu Arg Val Ala Leu Leu Glu
            435                 440                 445
Ala Leu Ala Val Ala Leu Leu Glu Ile Leu Glu Val Ala Leu Ala Leu
    450                 455                 460
Ala Leu Glu Cys Tyr Ser Pro His Glu Gly Leu Tyr Thr Tyr Arg Ala
465                 470                 475                 480
Arg Gly Met Glu Thr Leu Glu Thr His Arg Gly Leu Tyr Ala Ser Pro
                485                 490                 495
Ala Arg Gly Leu Tyr Ser Gly Leu Asn Gly Leu Tyr Leu Glu His Ile
                500                 505                 510
Ser Ser Glu Arg Met Glu Thr Ala Ser Asn Met Glu Thr Met Glu Thr
            515                 520                 525
Gly Leu Ala Leu Ala Ala Leu Ala Ala Leu Ala Ala Leu Ala Gly Leu
            530                 535                 540
Pro Arg Ser Glu Arg Leu Glu Ala Ser Pro Leu Glu
545                 550                 555

(2) INFORMATION FOR SEQ ID NO:27:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:27:

Leu Asn Thr Arg Val Gly Thr Lys Arg Tyr Met Ala Pro Glu Val Leu
1               5                   10                  15
Asp Glu Ser Leu Asn Lys Asn Cys
            20

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTGTGTGAAG ATAAGCCAGT C                                        21

(2) INFORMATION FOR SEQ ID NO:29:

(i) SEQUENCE CHARACTERISTICS:
        (A) LENGTH: 12 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:29:

CUACUACUAC UA                                                              12

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGCCACGCGT CGACTAGTAC G                                                    21

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGNNGGGNNG GGNNG                                                           15

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CAAGAGCTTA CCCAATCACT TG                                                   22

(2) INFORMATION FOR SEQ ID NO:33:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CACACGCGTC GACCATGACT TCCTCGCTGC ATCG                                      34

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
AACAGCTATG ACCATG                                                      16

(2) INFORMATION FOR SEQ ID NO:35:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:35:

CCTGTCACAT AATAGGCGTG TGCC                                             24

(2) INFORMATION FOR SEQ ID NO:36:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:36:

CGCGGATCCA TCATACTGAC AGCATCG                                          27

(2) INFORMATION FOR SEQ ID NO:37:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:37:

GCTGGGTAGT CCCCACCTTT                                                  20

(2) INFORMATION FOR SEQ ID NO:38:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:38:

GAGCAAGTTC AGCCTGGT                                                    18

(2) INFORMATION FOR SEQ ID NO:39:

(i) SEQUENCE CHARACTERISTICS:
         (A) LENGTH: 19 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:39:
```

-continued

```
Ala Arg Pro Arg Tyr Ser Ile Gly Leu Glu Gln Asp Glu Thr Tyr Ile
1               5                   10                  15
Pro Pro Cys
```